US011339404B2

(12) United States Patent
Sung et al.

(10) Patent No.: US 11,339,404 B2
(45) Date of Patent: May 24, 2022

(54) PROTOPORPHYRINOGEN OXIDASE VARIANTS AND METHODS AND COMPOSITIONS FOR CONFERRING AND/OR ENHANCING HERBICIDE TOLERANCE USING THE SAME

(71) Applicant: FarmHannong Co., Ltd., Seoul (KR)

(72) Inventors: Soon-Kee Sung, Daejeon (KR); Joonseon Yoon, Daejeon (KR); Young Ock Ahn, Daejeon (KR); Yunjung Han, Daejeon (KR); Myoung-Ki Hong, Daejeon (KR); Joonghyuk Park, Daejeon (KR)

(73) Assignee: FARMHANNONG CO., LTD., Seoul (KR)

( * ) Notice: Subject to any disclaimer, the term of this patent is extended or adjusted under 35 U.S.C. 154(b) by 243 days.

(21) Appl. No.: 16/307,660

(22) PCT Filed: Jun. 15, 2017

(86) PCT No.: PCT/KR2017/006276
§ 371 (c)(1),
(2) Date: Dec. 6, 2018

(87) PCT Pub. No.: WO2017/217794
PCT Pub. Date: Dec. 21, 2017

(65) Prior Publication Data
US 2019/0330650 A1    Oct. 31, 2019

(30) Foreign Application Priority Data

Jun. 16, 2016  (KR) .................. 10-2016-0075357

(51) Int. Cl.
*C12N 15/82* (2006.01)

(52) U.S. Cl.
CPC .. *C12N 15/8274* (2013.01); *C12Y 103/03004* (2013.01)

(58) Field of Classification Search
CPC ............................................... C12N 15/8274
See application file for complete search history.

(56) References Cited

U.S. PATENT DOCUMENTS

| 6,308,458 | B1 | 10/2001 | Volrath et al. |
| 6,808,904 | B2 | 10/2004 | Ward et al. |
| 7,563,950 | B2 | 7/2009 | Matsushima et al. |
| 7,842,856 | B2 | 11/2010 | Tranel et al. |
| 2015/0252379 | A1 | 9/2015 | Hutzler et al. |

FOREIGN PATENT DOCUMENTS

| JP | 2010-526535 | 8/2010 |
| JP | 2014-504855 | 2/2014 |
| JP | 2015-519913 | 7/2015 |
| JP | 2017-533480 | 11/2017 |
| KR | 10-2007-0114338 | 12/2007 |
| KR | 10-2014-0033330 | 3/2014 |
| WO | 2011-085221 | 7/2011 |
| WO | 2013-189984 | 12/2013 |
| WO | 2015-022636 | 2/2015 |
| WO | 2015-092706 | 6/2015 |
| WO | WO 2015/092706 | * 6/2015 ......... C12N 15/8274 |
| WO | 2016-099153 | 6/2016 |

OTHER PUBLICATIONS

GenBank Accession No. AFZ07847 published Jul. 22, 2013 (Year: 2013).*
NCBI Reference Sequence WP_015224927.1 Protoporphyrinogen Oxidase [*Halothece* sp. PCC 7418] Published May 19, 2013 (Year: 2013).*
F5UKM3_9CYAN Protoporphyrinogen oxidase dated Jan. 7, 2020; uniprot.org/uniprot/F5UKM3.txt?version=20.
X. Li et al., "Development of Protoporphyrinogen Oxidase as an Efficient Selection Marker for Agrobacterium tumefaciens-Mediated Transformation of Maize", Plant physiology, vol. 133, pp. 736-747, 2003.
U. B. Nandihalli et al., "Relationships between molecular properties and biological activities of O-phenyl pyrrolidino- and piperidinocarbamate herbicides", J. Agric. Food Chem., vol. 40, No. 10, pp. 1993-2000, 1992.
N. Watanabe et al., "Dual targeting of spinach protoporphyrinogen oxidase II to mitochondria and chloroplasts by alternative use of two in-frame inhibition codons"; The Journal of Biological Chemistry, vol. 276, No. 23, pp. 20474-20481, 2001, JBC 20474-20481.
F.-S. Che et al., "Molecular Characterization and Subcellular Localization of Protoporphyrinogen Oxidase in Spinach Chloroplasts", Plant Physiology, vol. 124, 2000.
NCBI, Reference Sequence No. WP_015177110.1, protoporphyrinogen oxidase [Oscillatoria nigro-viridis], 2017. 7. 10.
NCBI, Reference Sequence No. WP_009787090.1, protoporphyrinogen oxidase [*Lyngbya* sp. PCC 8106], 2017. 7. 10.
NCBI, Reference Sequence No. WP_015224927.1, protoporphyrinogen oxidase [*Halothece* sp. PCC 7418], 2017. 7. 10.
G.-F. Hao et al., "Understanding Resistance Mechanism of Protoporphyrinogen Oxidase-Inhibiting Herbicides: Insights from Computational Mutation Scanning and Site-Directed Mutagenesis", Journal of Agricultural and Food Chemistry, vol. 62, pp. 7209-7215, 2014.
EPO, Extended European Search Report of the corresponding European Patent Application No. 17813617.2 dated Nov. 11, 2019.
Database UniParc [Online] uniprot; XP002795131, accession No. UPI0002A05DE4, Dec. 2012.
Database UniParc [Online] uniprot; XP002795132, accession No. UPI0000EAA8F1, Jan. 2007.
Database UniParc [Online] uniprot; XP002795196, accession No. UPI0002A04F9A, Dec. 2012.
NCBI, Reference Sequence No. WP_006634434.1, protoporphyrinogen oxidase [Microcoleus vaginatus], 2019. 10. 8.

(Continued)

*Primary Examiner* — David H Kruse
(74) *Attorney, Agent, or Firm* — Lex IP Meister, PLLC

(57) ABSTRACT

Provided is technology for conferring enhanced tolerance and/or enhancing tolerance to herbicide of a plant and/or algae using amino acid variants of protoporphyrinogen oxidase derived from prokaryotes.

14 Claims, 49 Drawing Sheets
(42 of 49 Drawing Sheet(s) Filed in Color)
Specification includes a Sequence Listing.

(56) References Cited

OTHER PUBLICATIONS

NCBI, Reference Sequence No. WP_023067908.1, protoporphyrinogen oxidase [Lyngbya aestuarii], 2019. 10. 8.
Hee Jae Lee et al., "Transgenic Rice Plants Expressing a Bacillus subtilis Protoporphyrinogen Oxidase Gene Are Resistant to Diphenyl Ether Herbicide Oxyfluorfen", Plant Cell Physiol. 41(6): 743-749 (2000).
Inna Lermontova et al., "Overexpression of Plastidic Protoporphyrinogen IX Oxidase Leads to Resistance to the Diphenyl-Ether Herbicide Acifluorfen", Plant Physiology, Jan. 2000, vol. 122, pp. 75-83.
CIPO, Office Action of CA 3,025,630 dated Nov. 4, 2021.

\* cited by examiner

[Fig. 1]
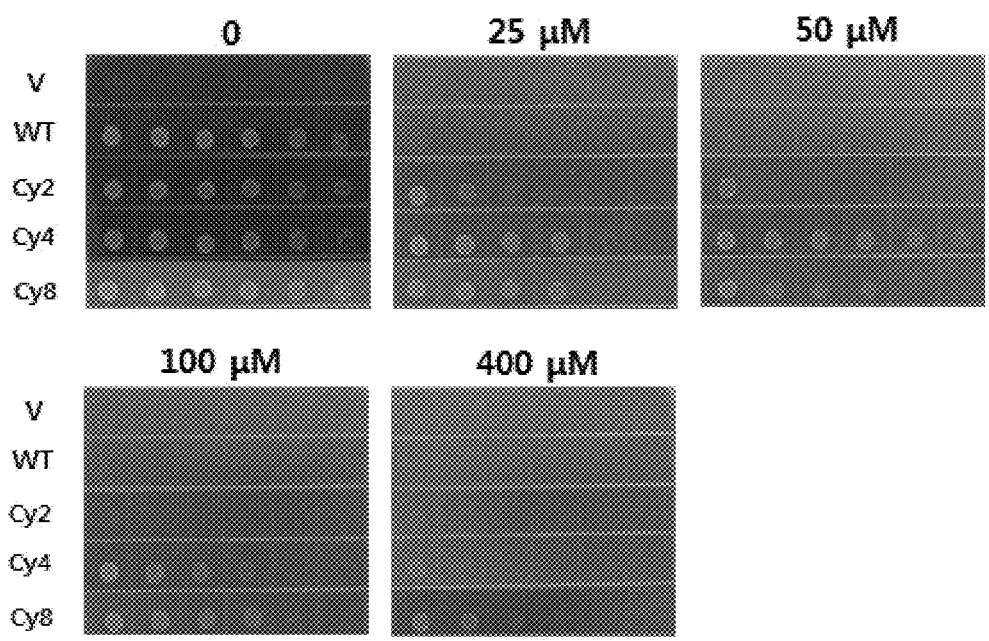

[Fig. 2]
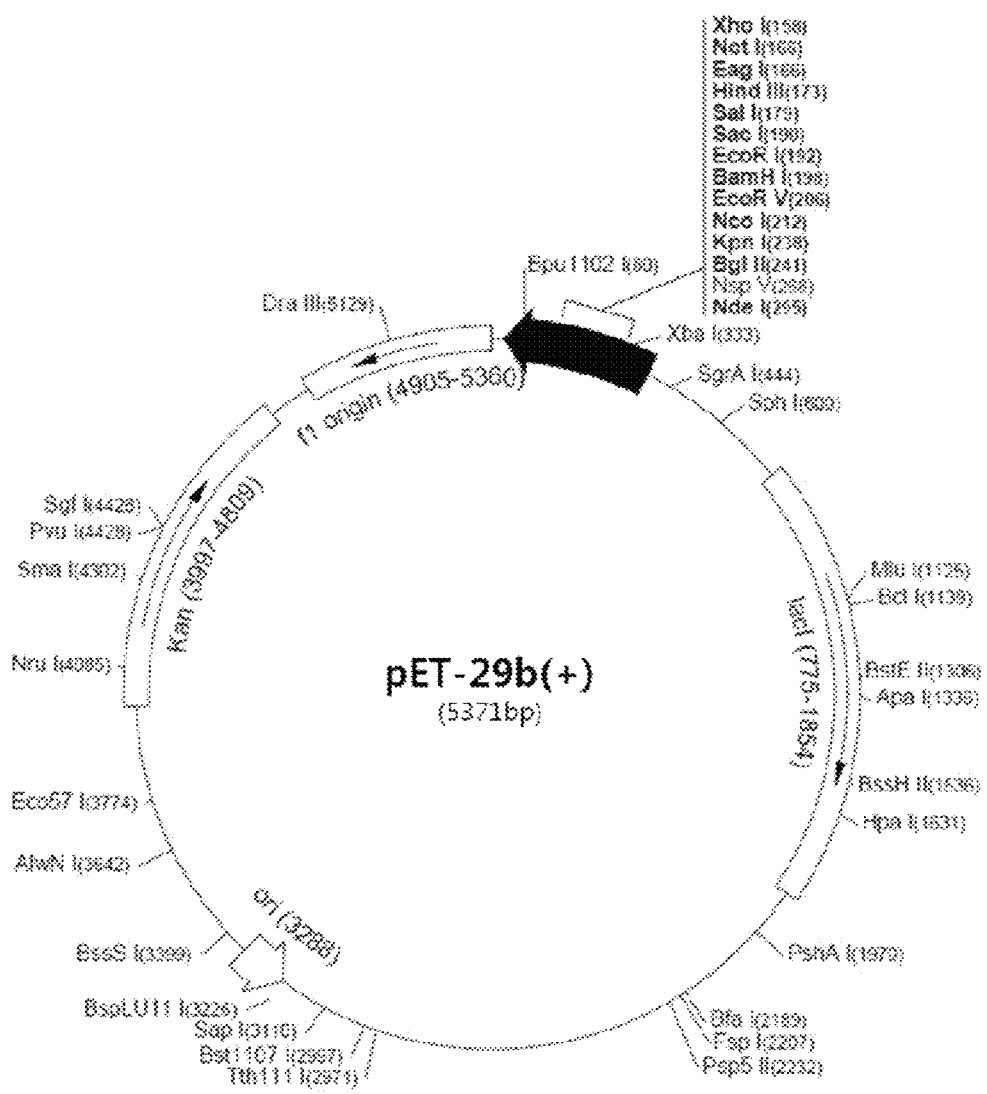

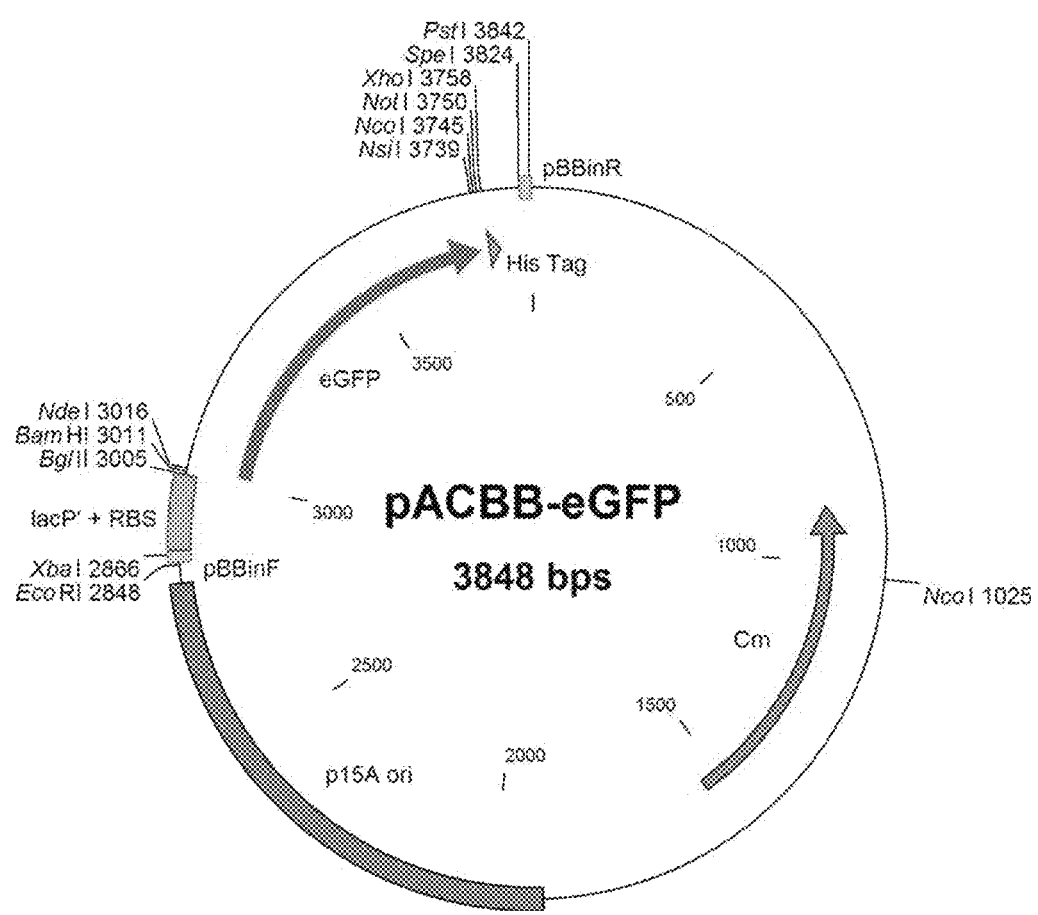
[Fig. 3]

[Fig. 4]
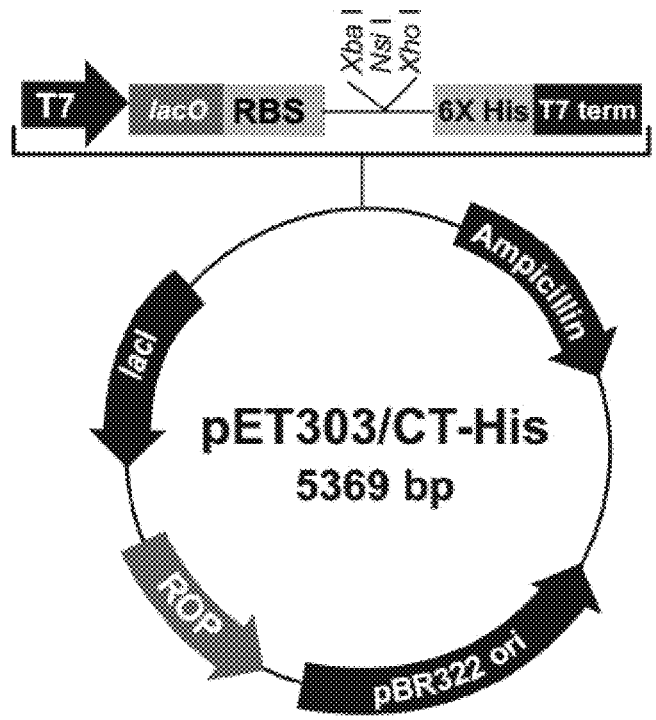

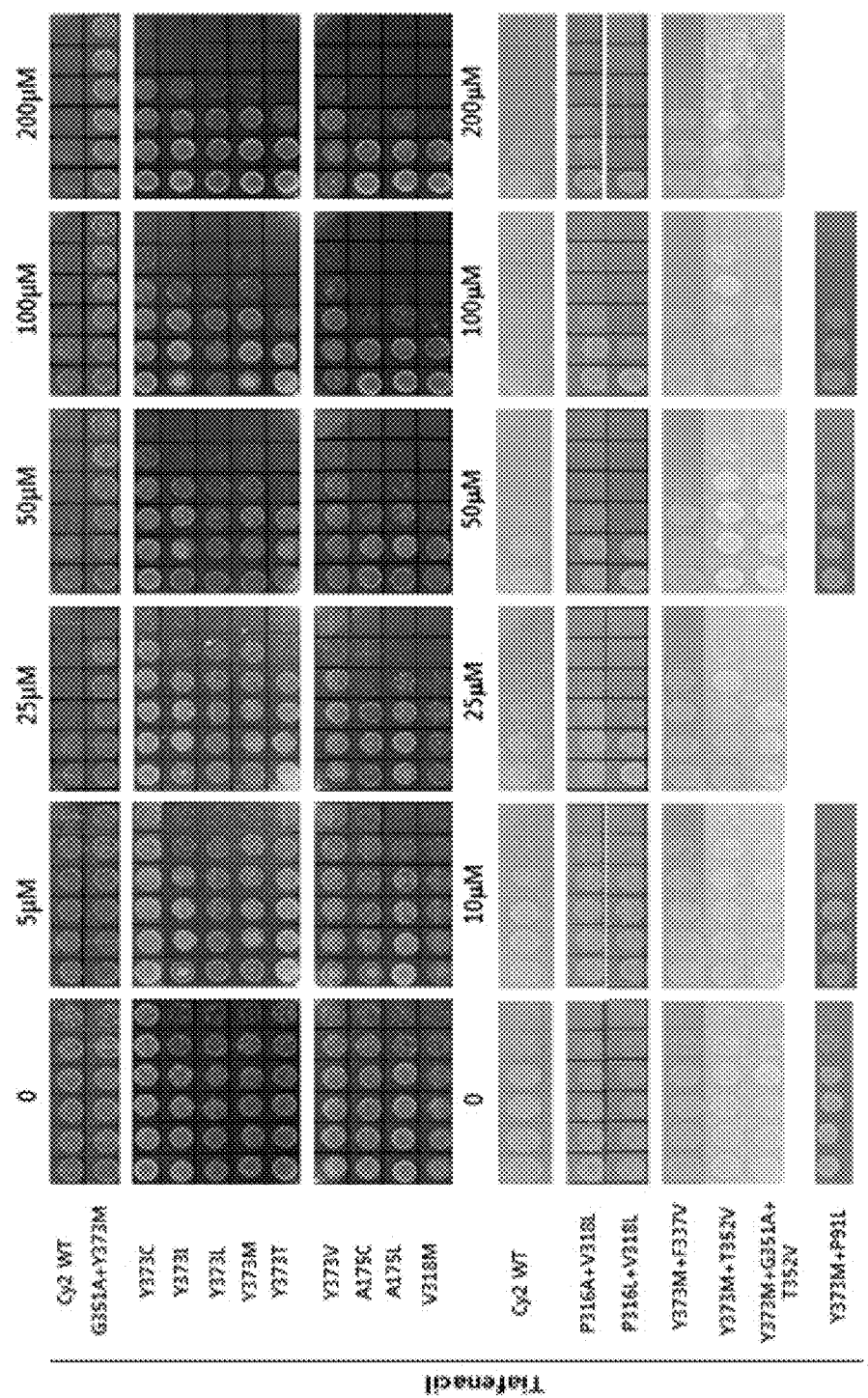
[Fig. 5]

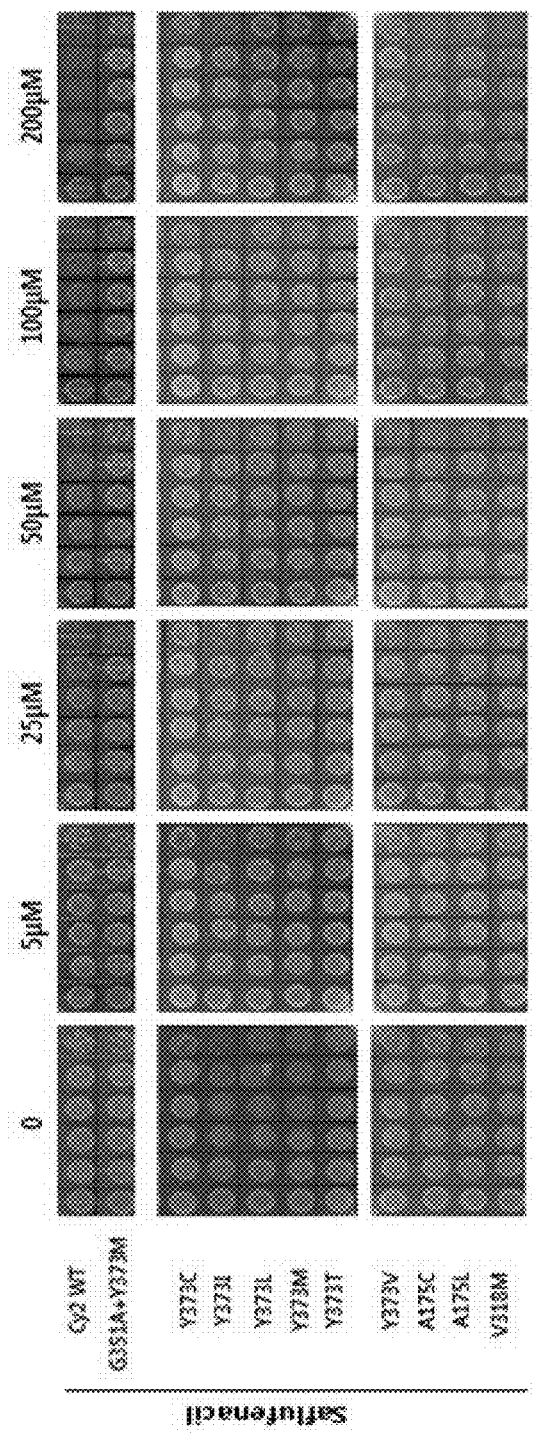
[Fig. 6]

[Fig. 7]
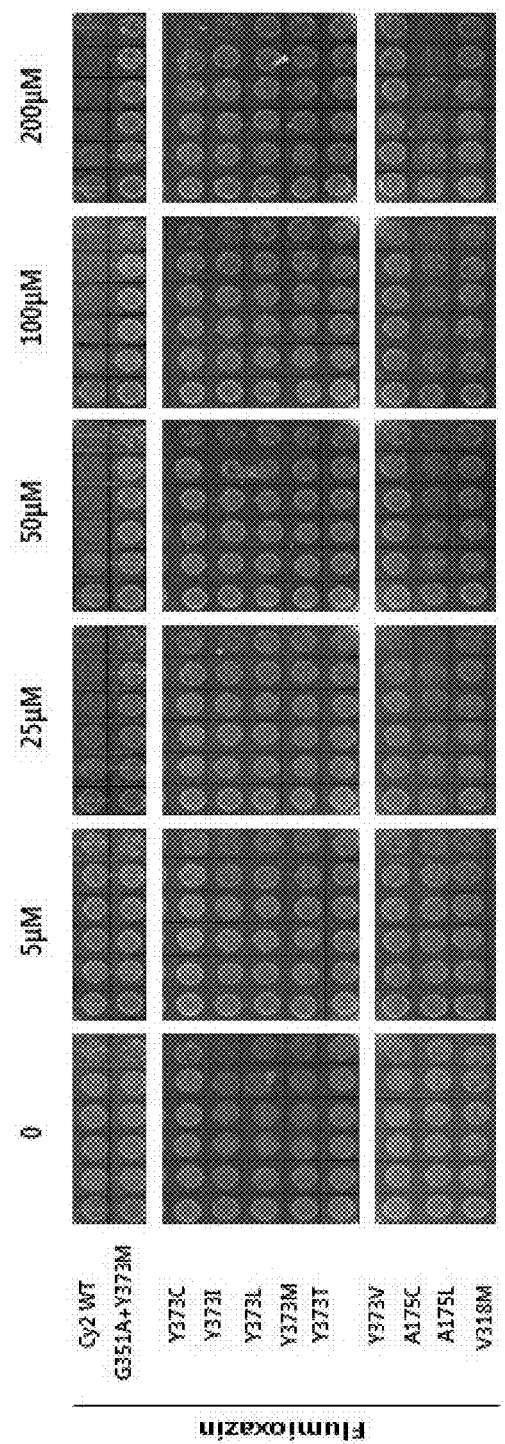

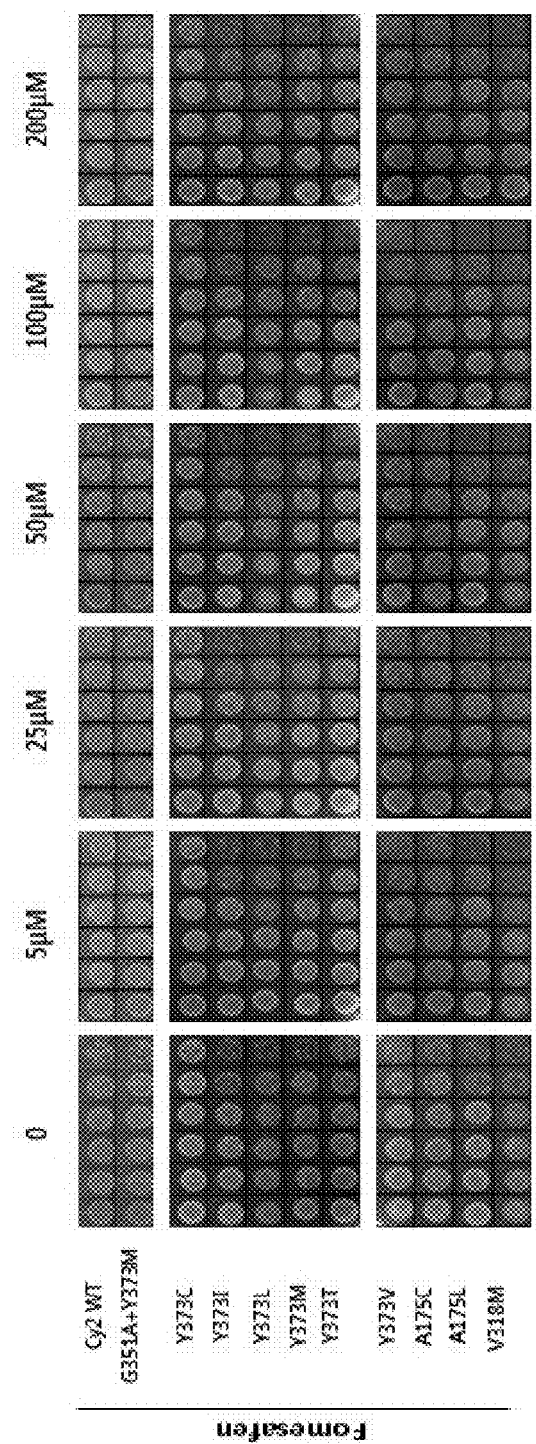
[Fig. 8]

[Fig. 9]
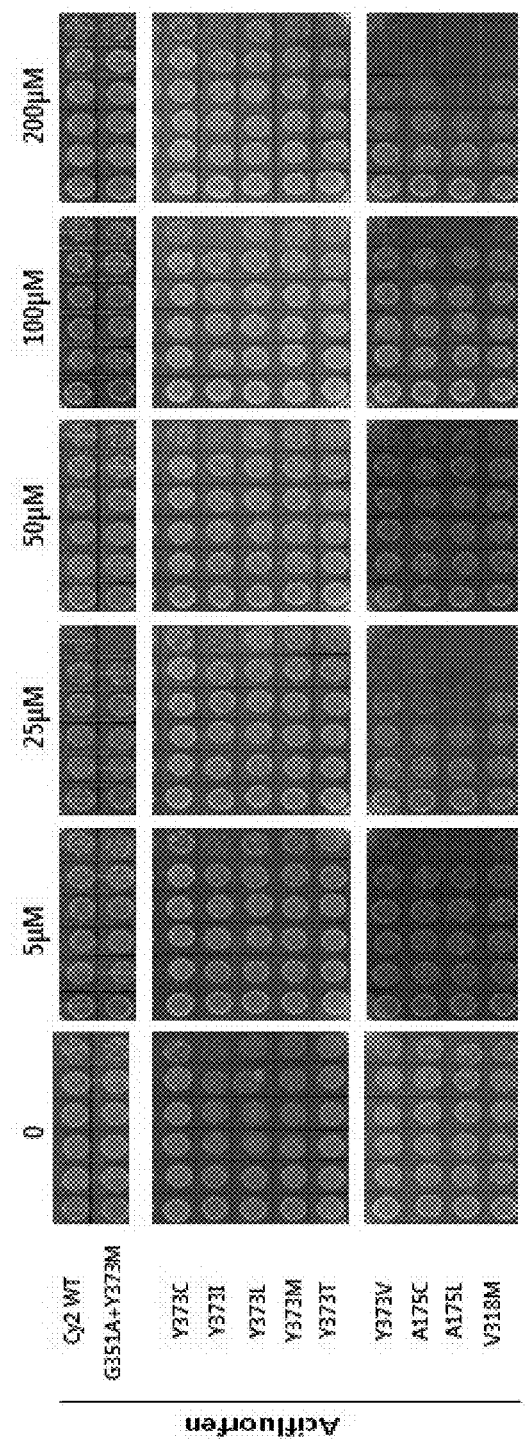

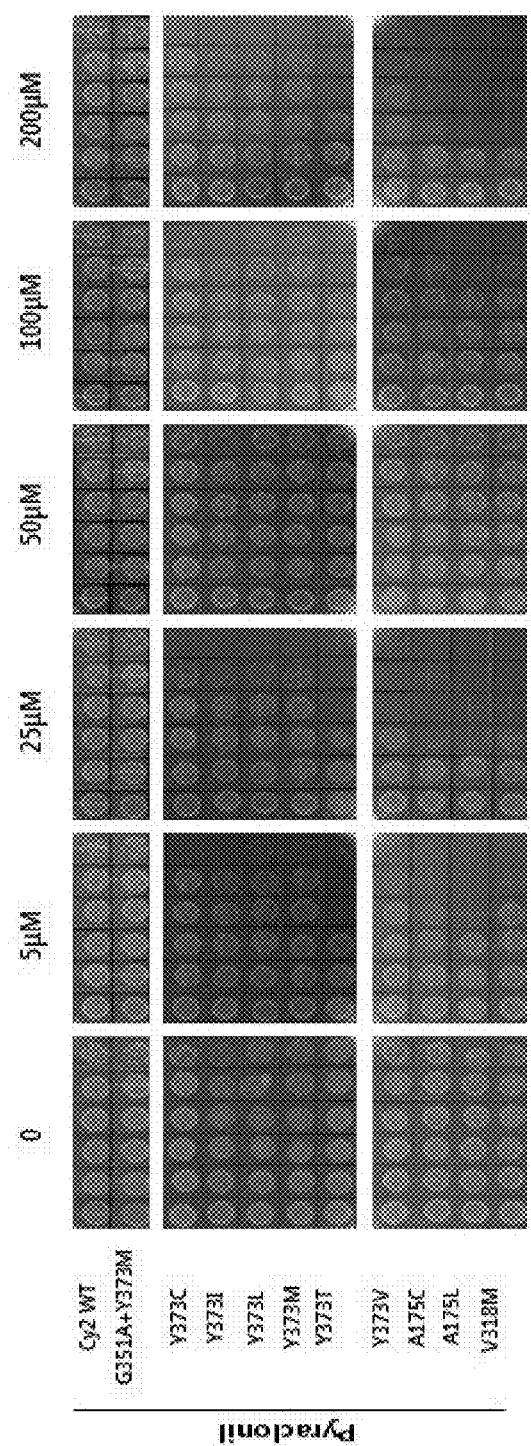
[Fig. 10]

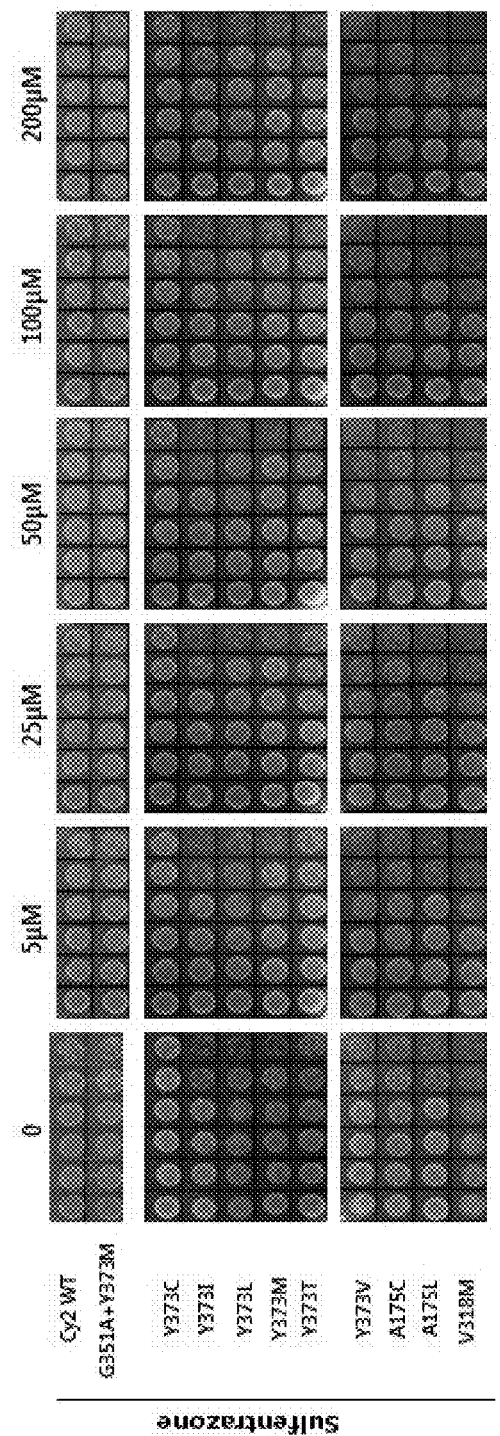
[Fig. 11]

[Fig. 12]
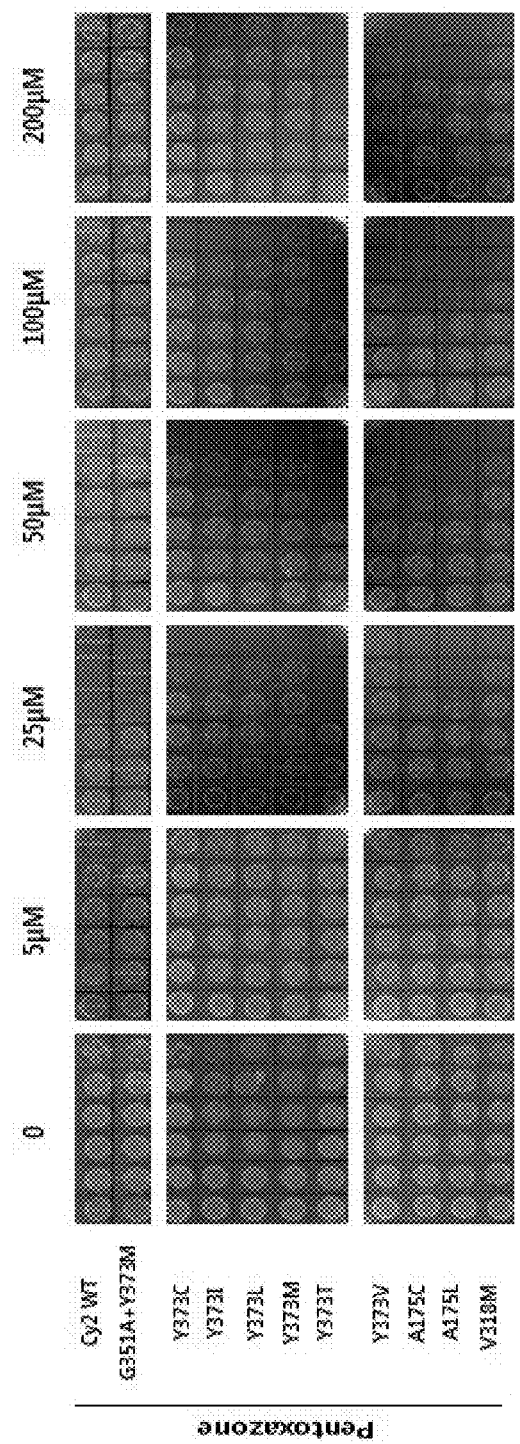

[Fig. 13]
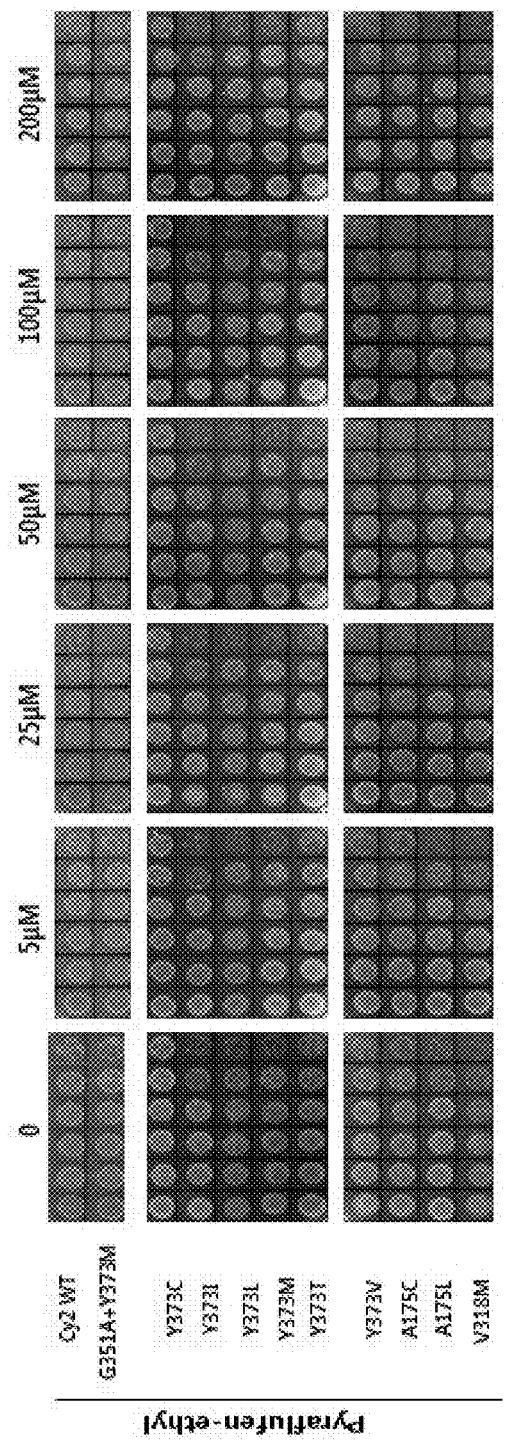

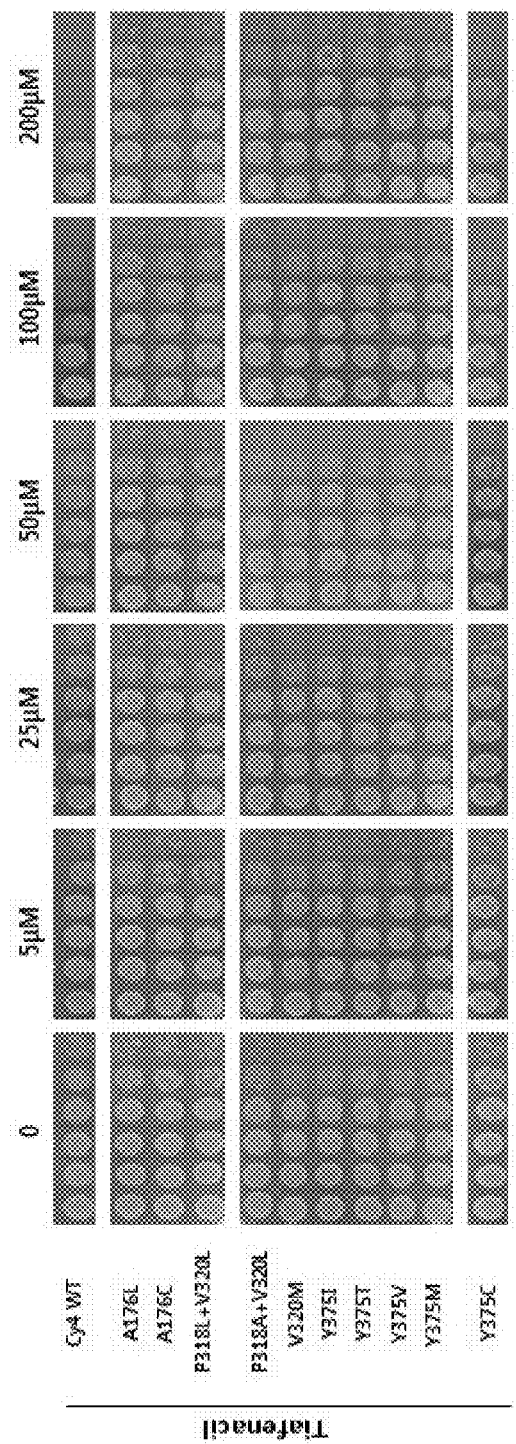
[Fig. 14]

[Fig. 15]
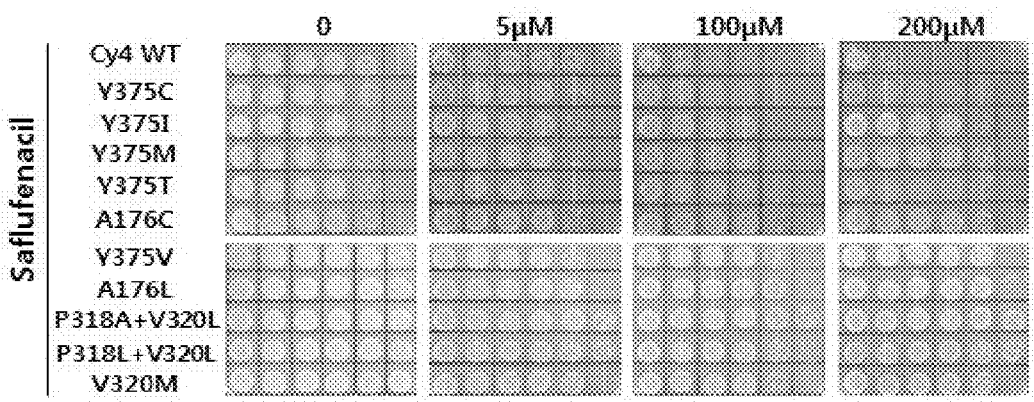
[Fig. 16]
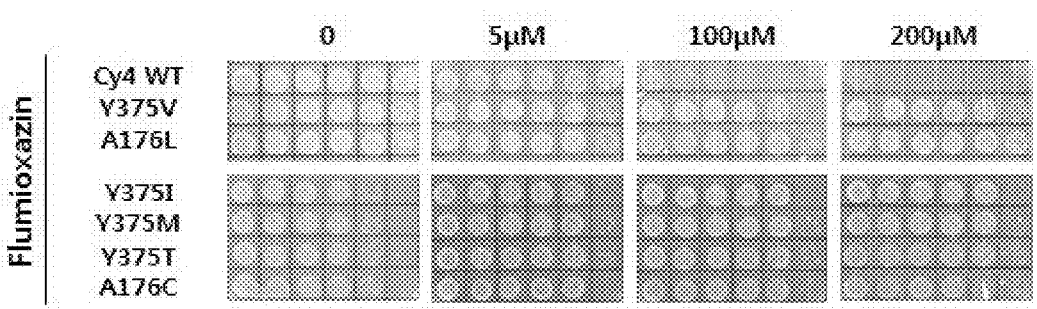

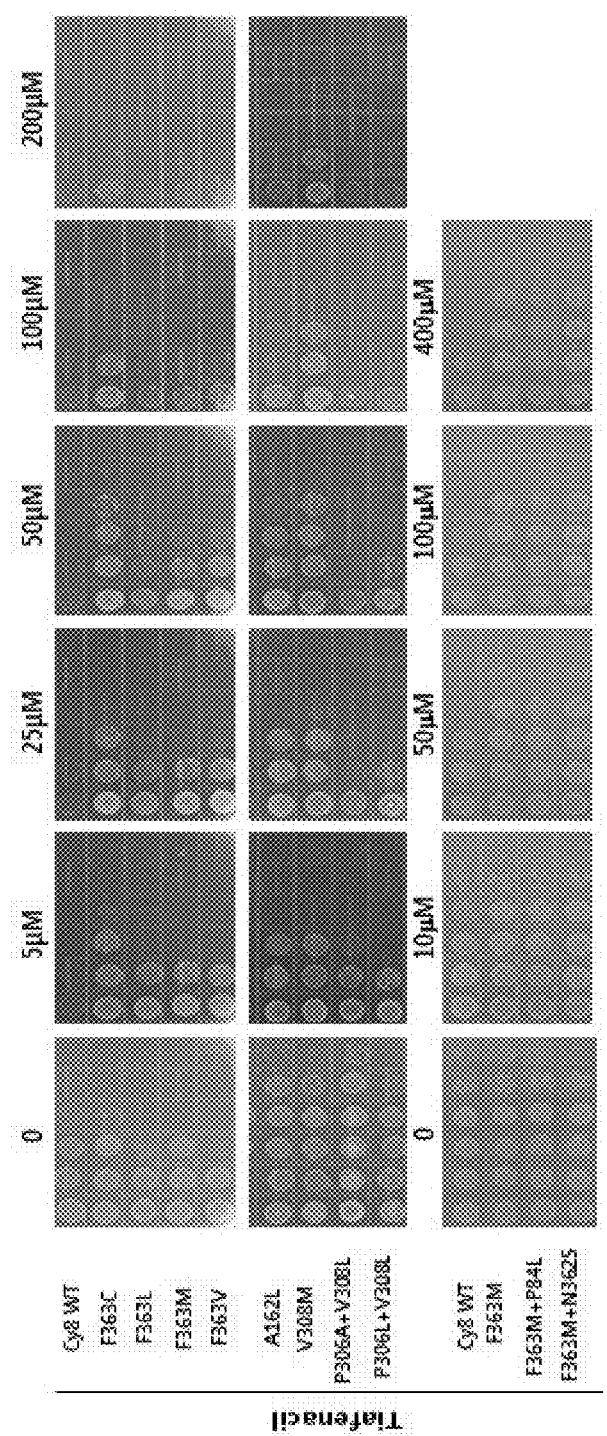
[Fig. 17]

[Fig. 18]
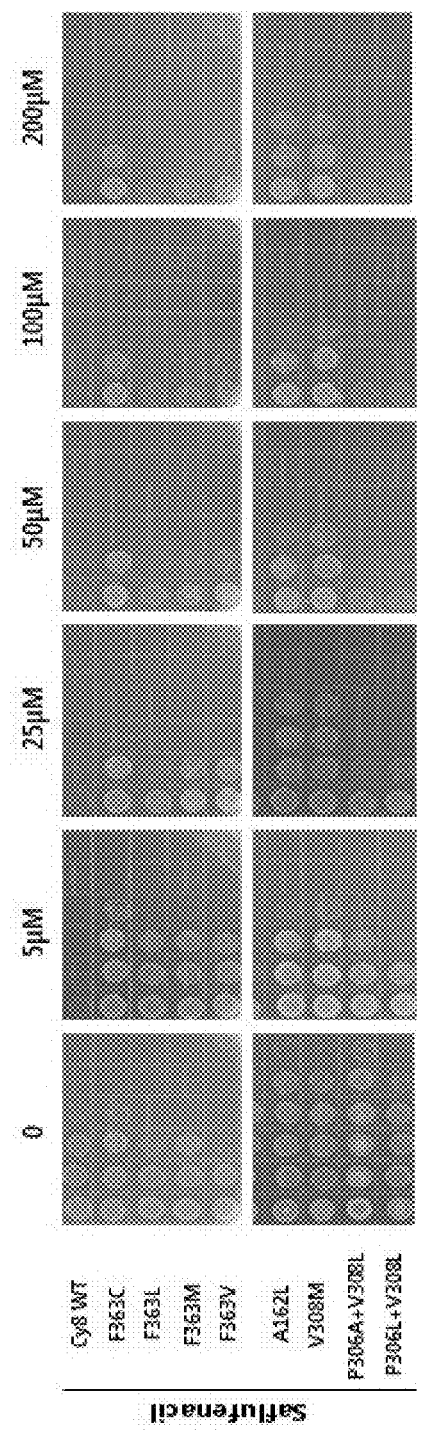

[Fig. 19]
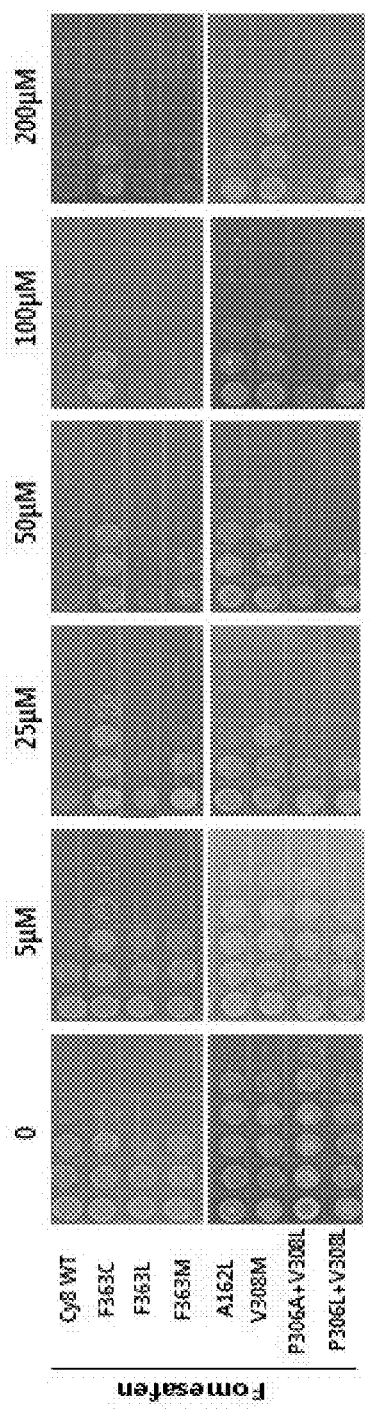

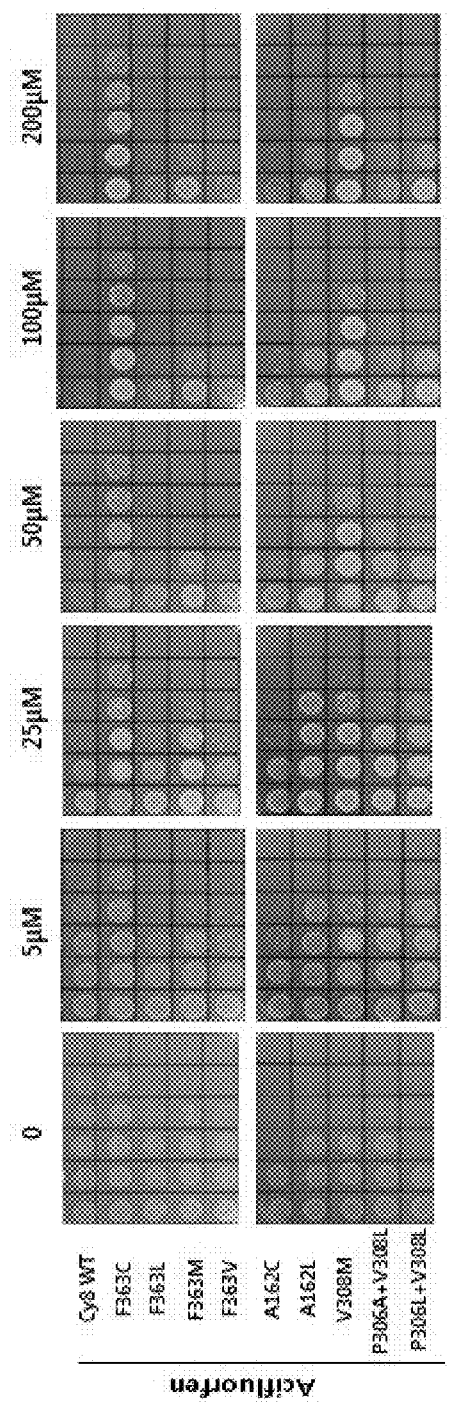
[Fig. 20]

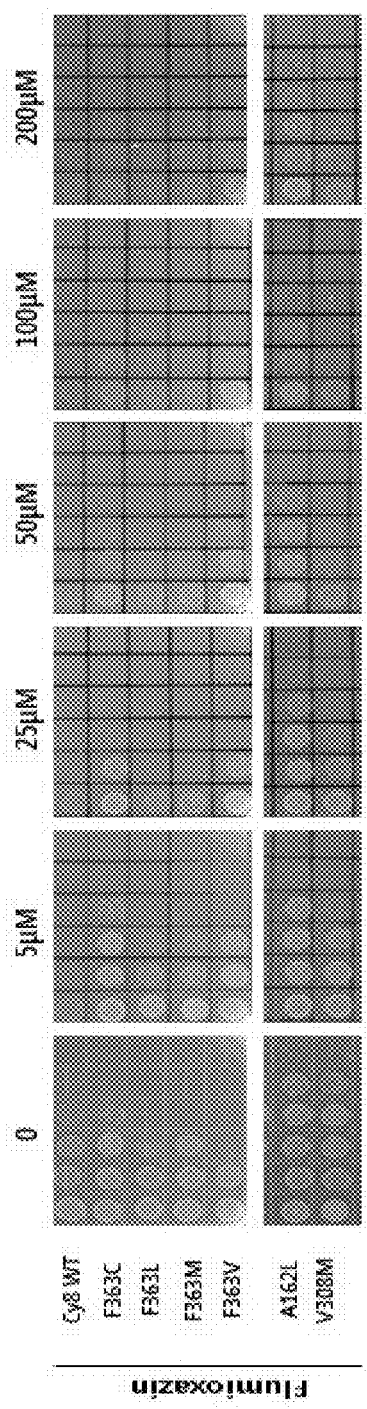
[Fig. 21]

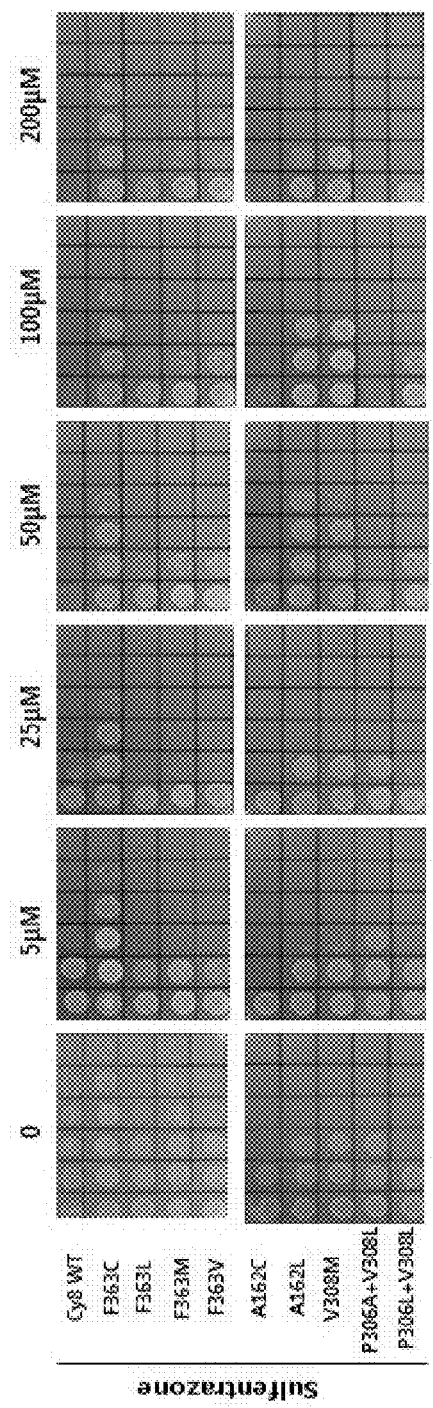
[Fig. 22]

[Fig. 23]
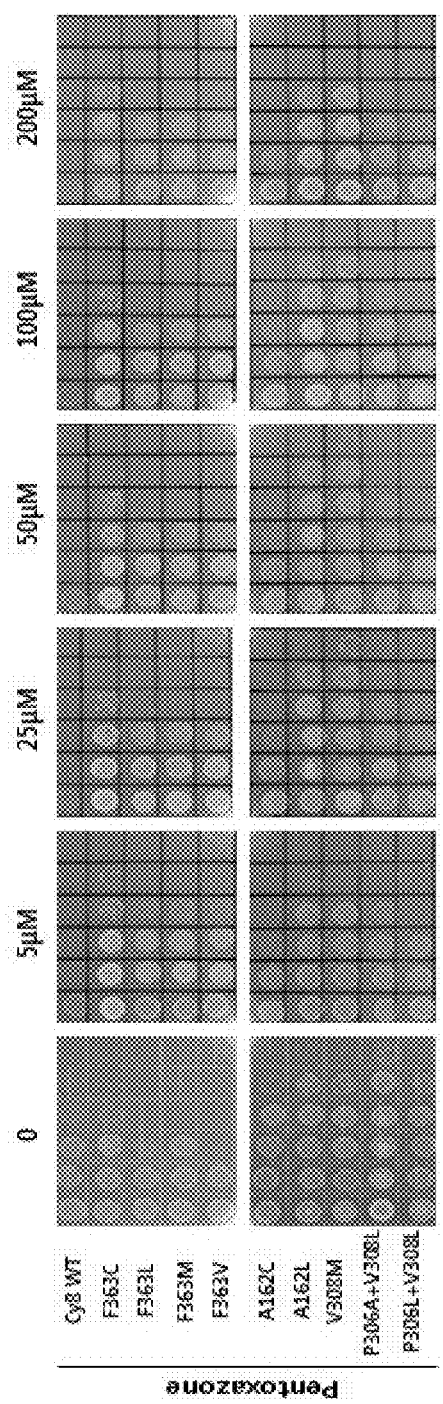

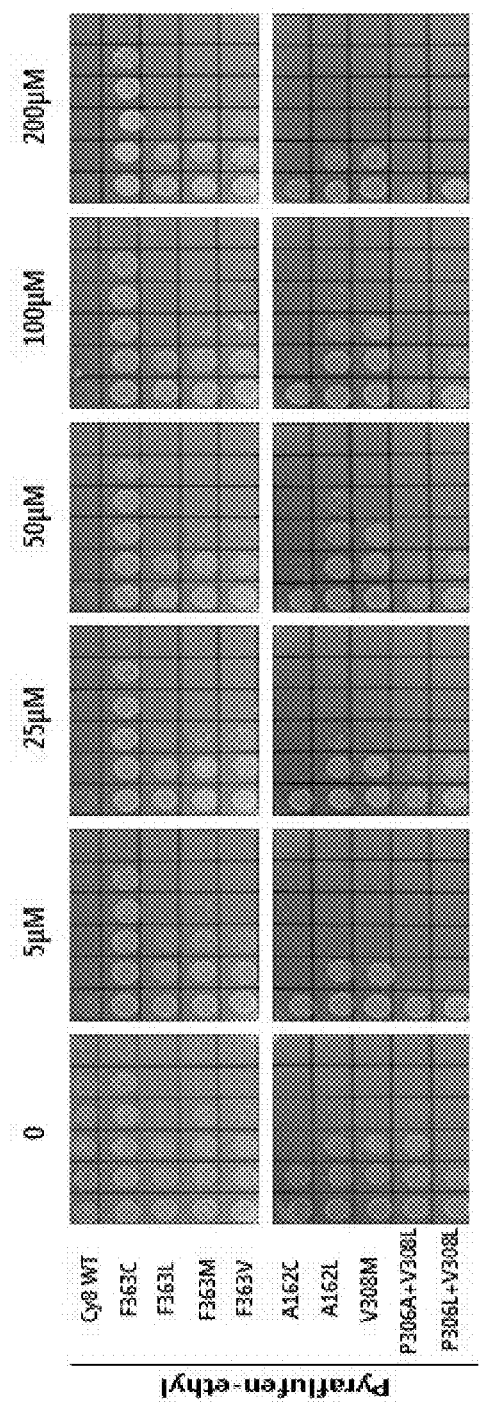
[Fig. 24]

[Fig. 25]
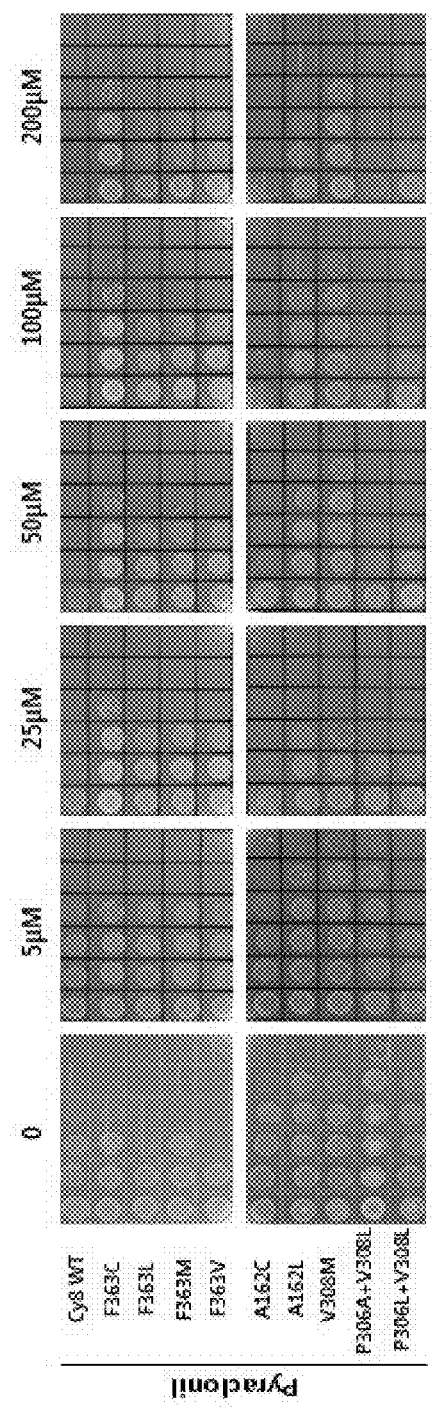

[Fig. 26]
Vector for Fusion Protein of PPO and MBP(Maltose binding protein)
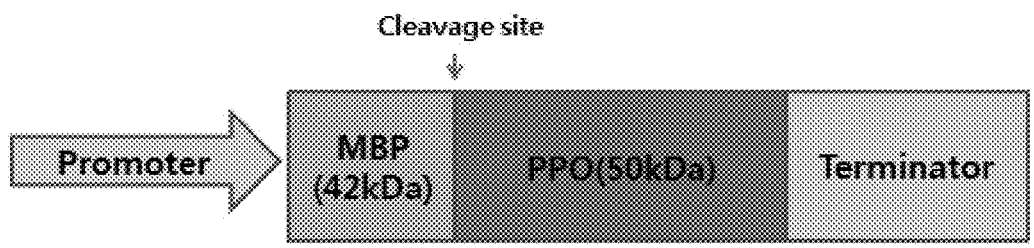
[Fig. 27]
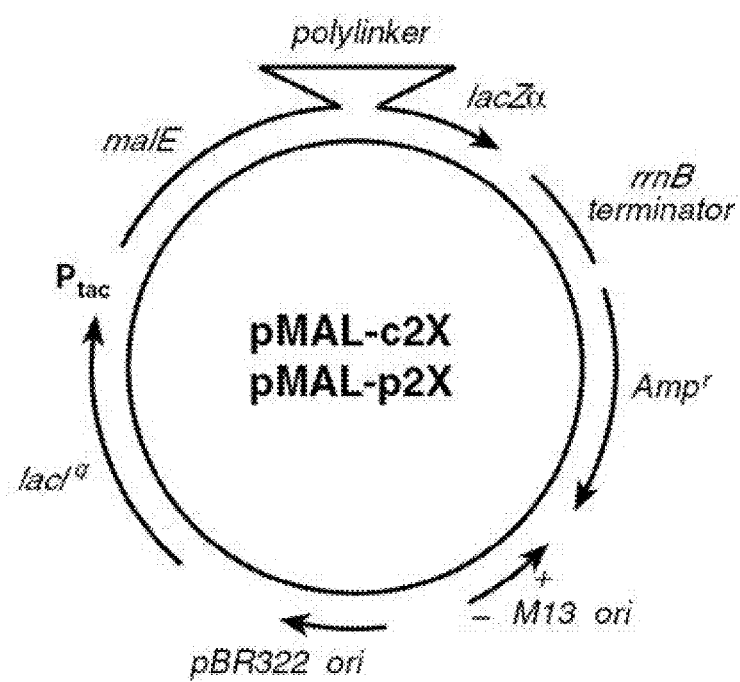

[Fig. 28]
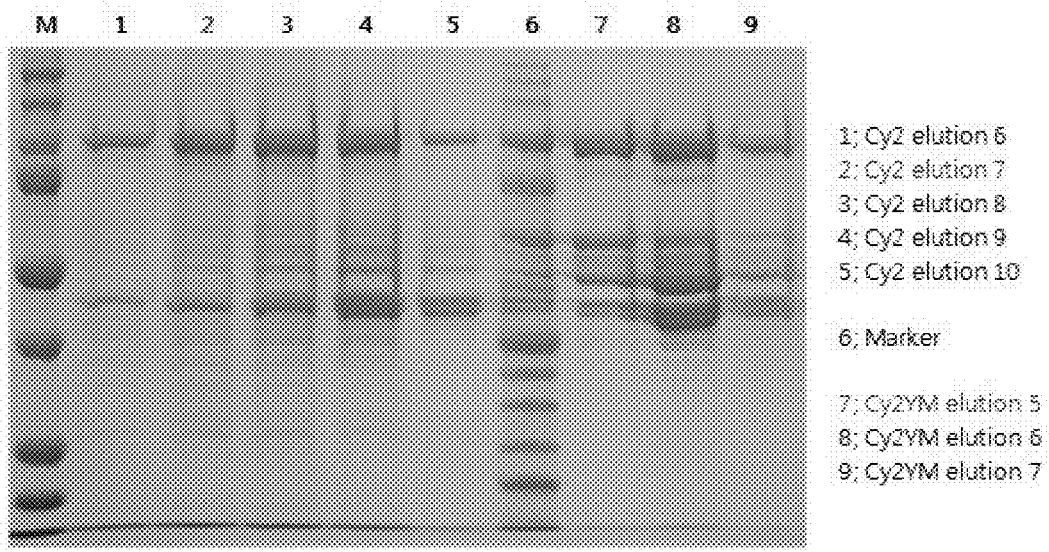
[Fig. 29]
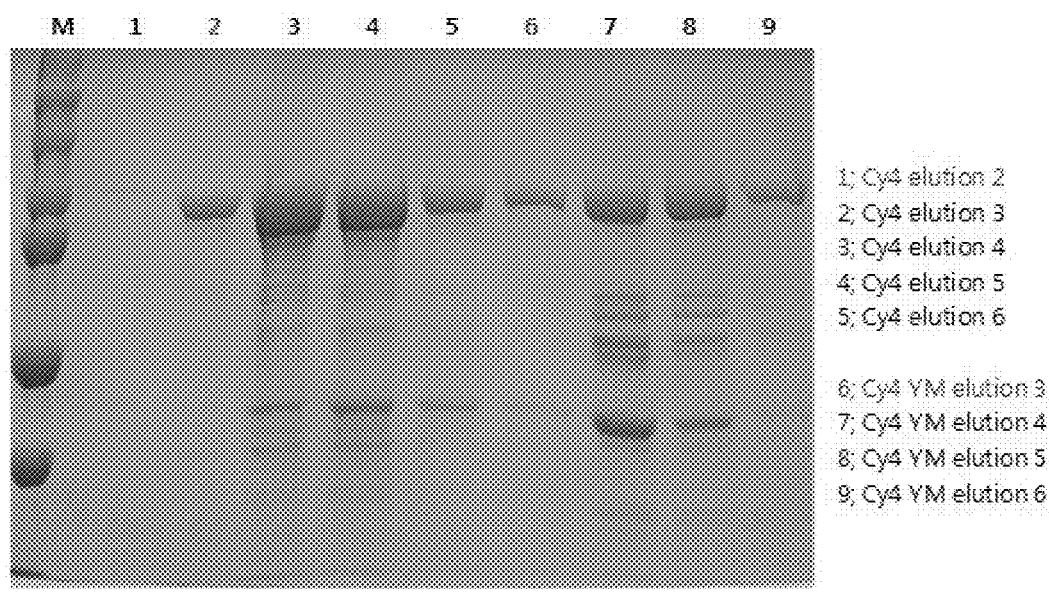

[Fig. 30]
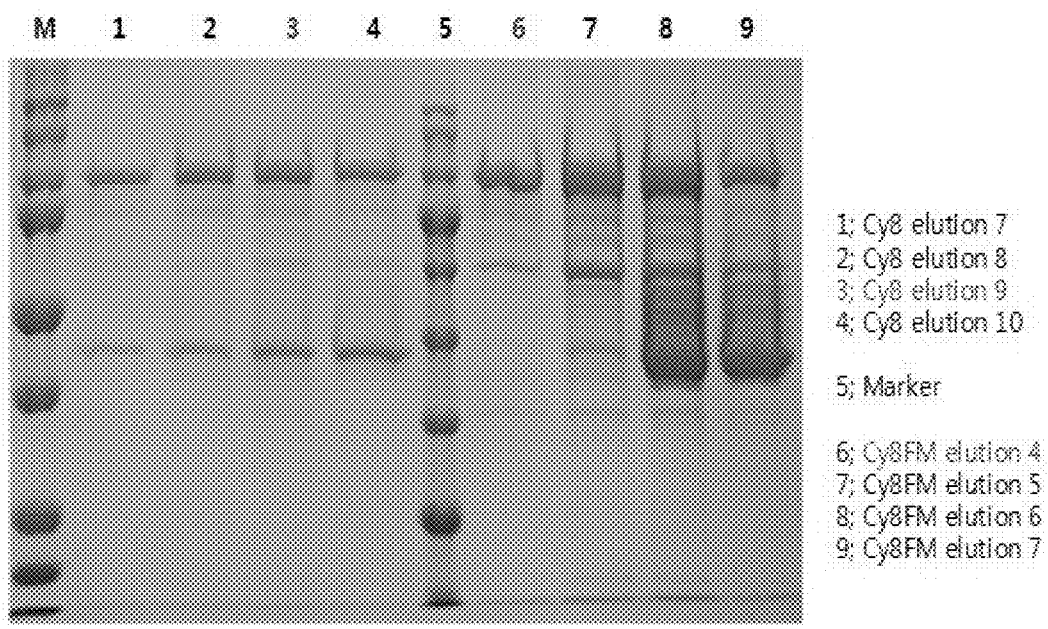

[Fig. 31]
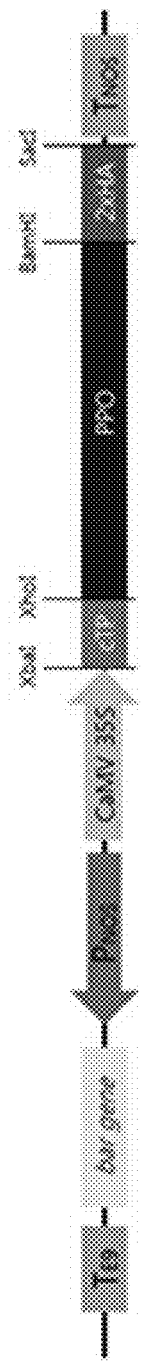

[Fig. 32]
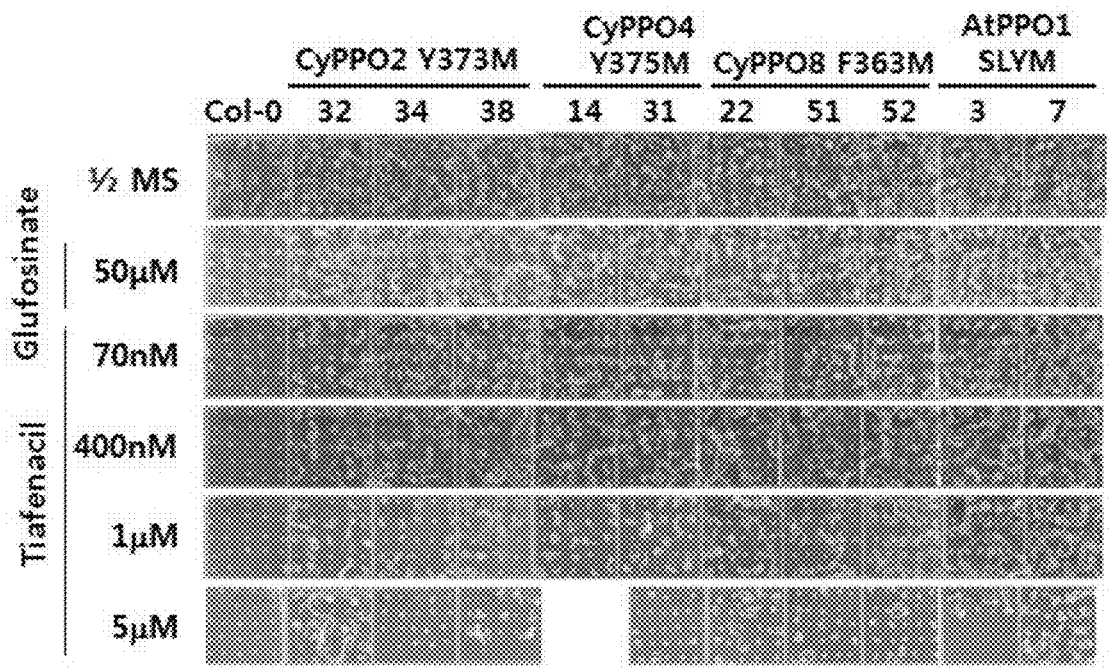
[Fig. 33]
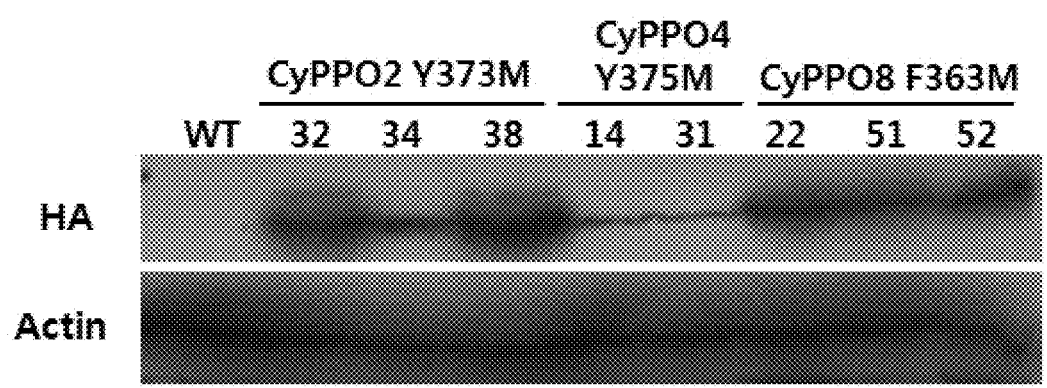

[Fig. 34]
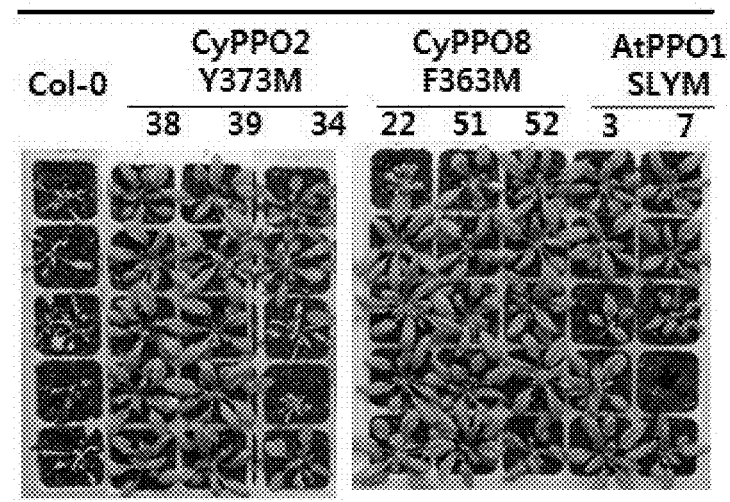
[Fig. 35]
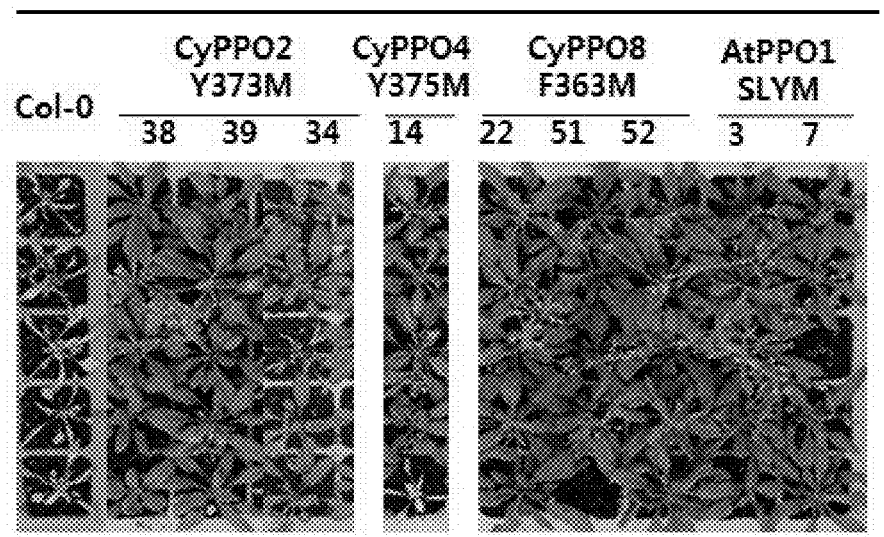

[Fig. 36]
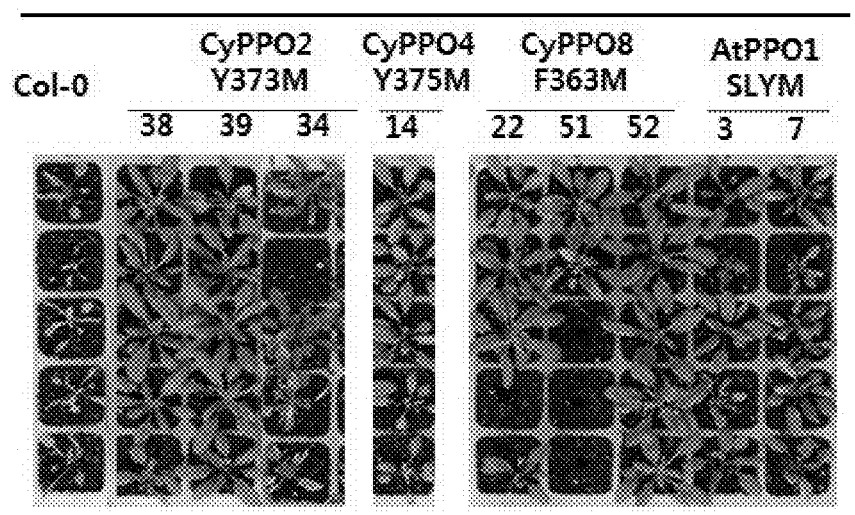

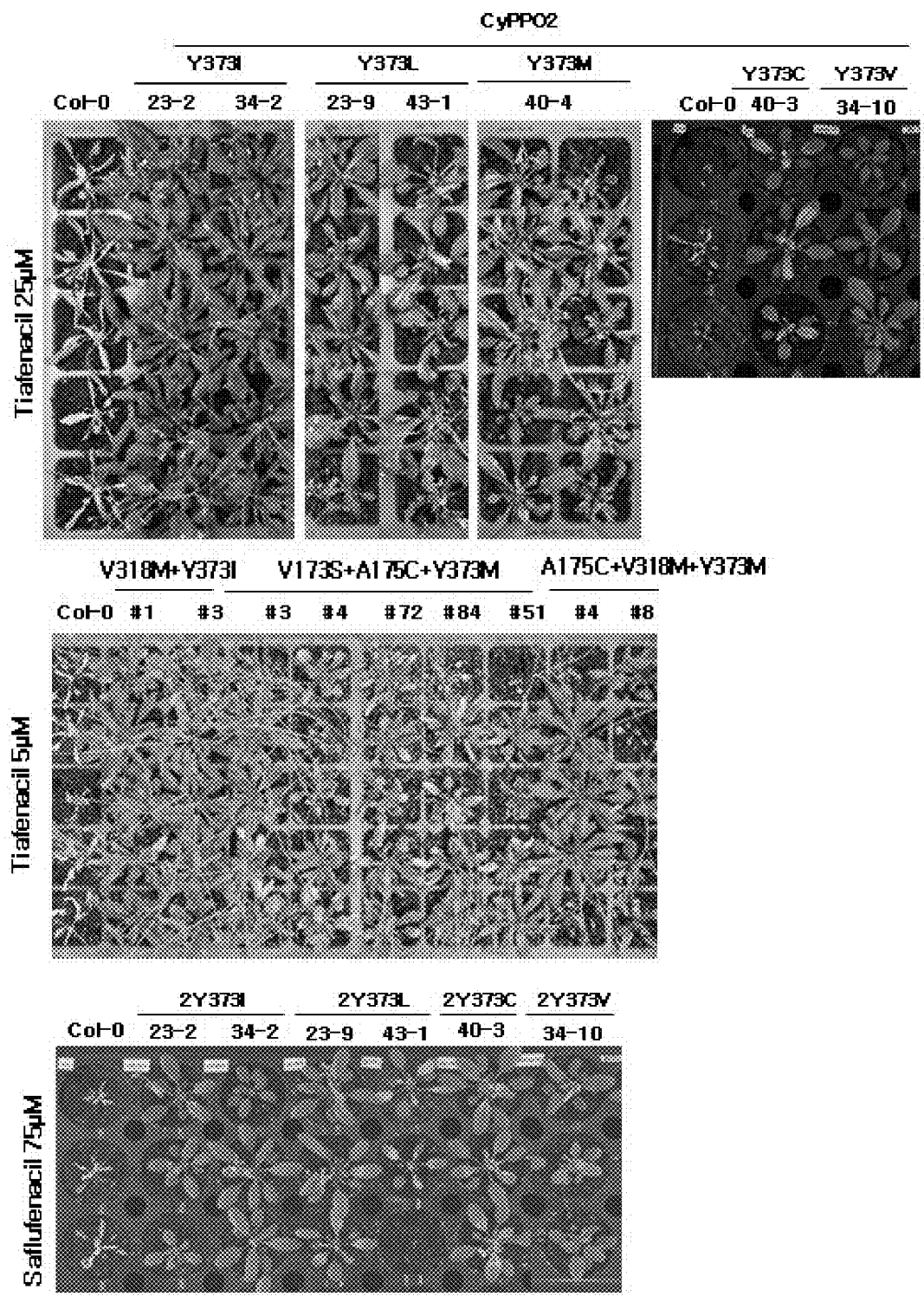
[Fig. 37]

[Fig. 38]
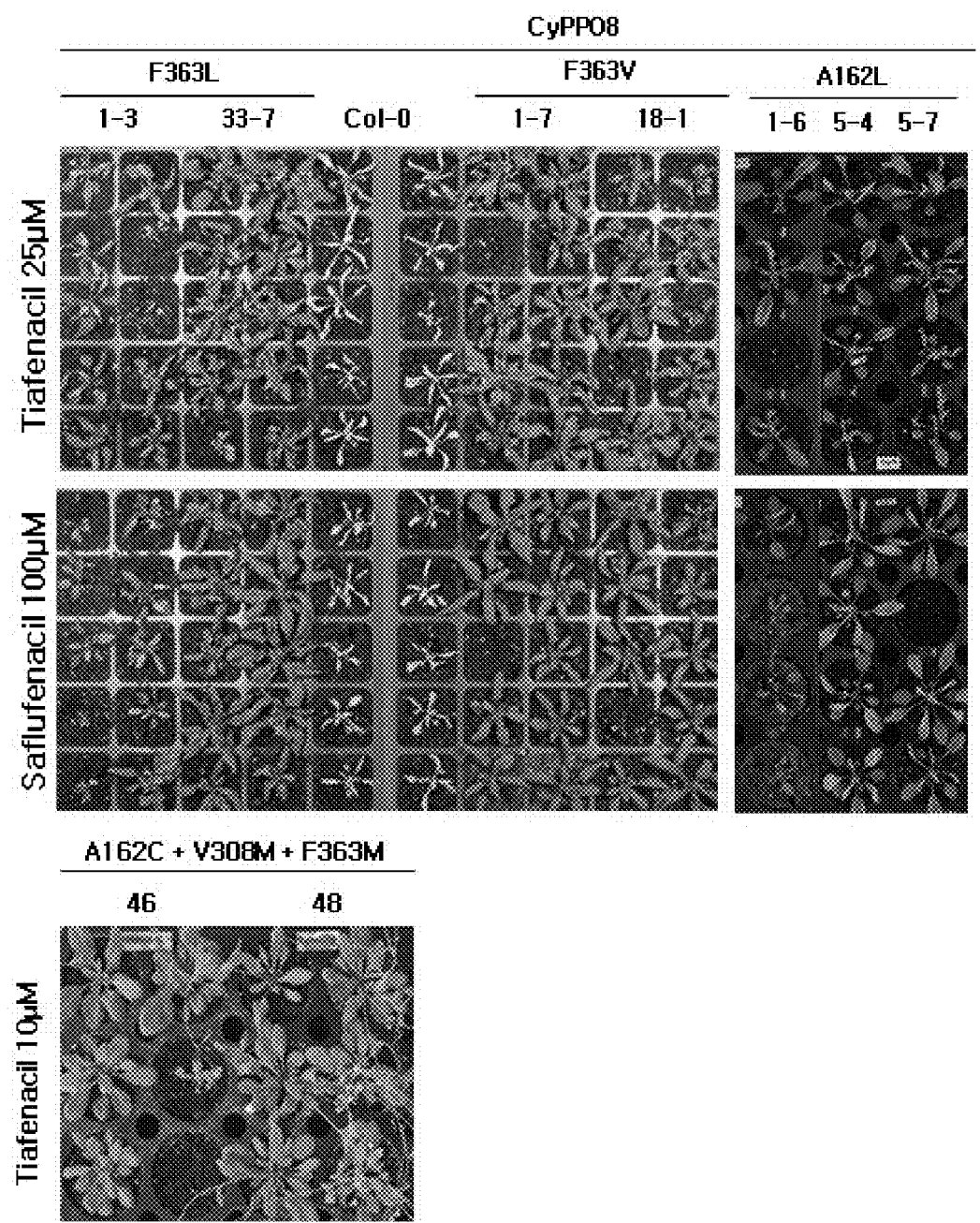

[Fig. 39]
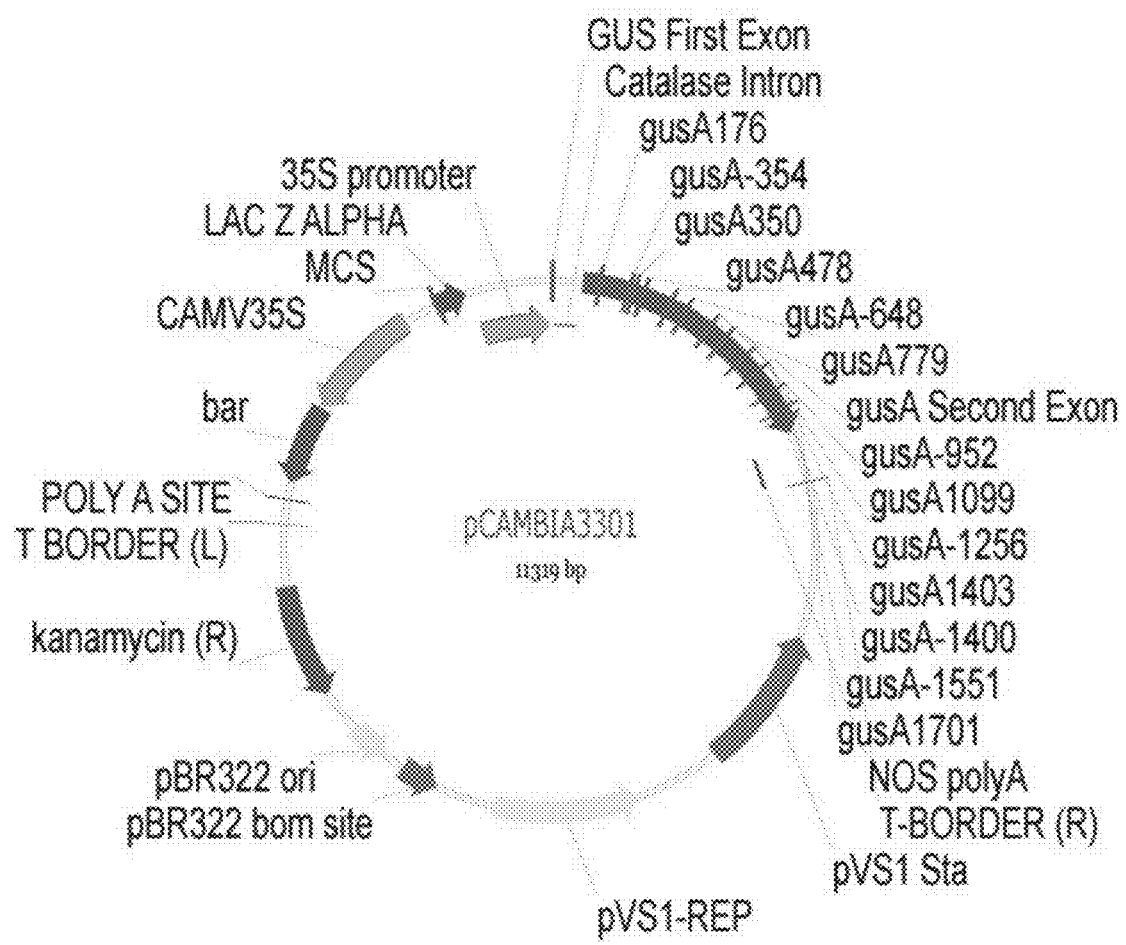

[Fig. 40]
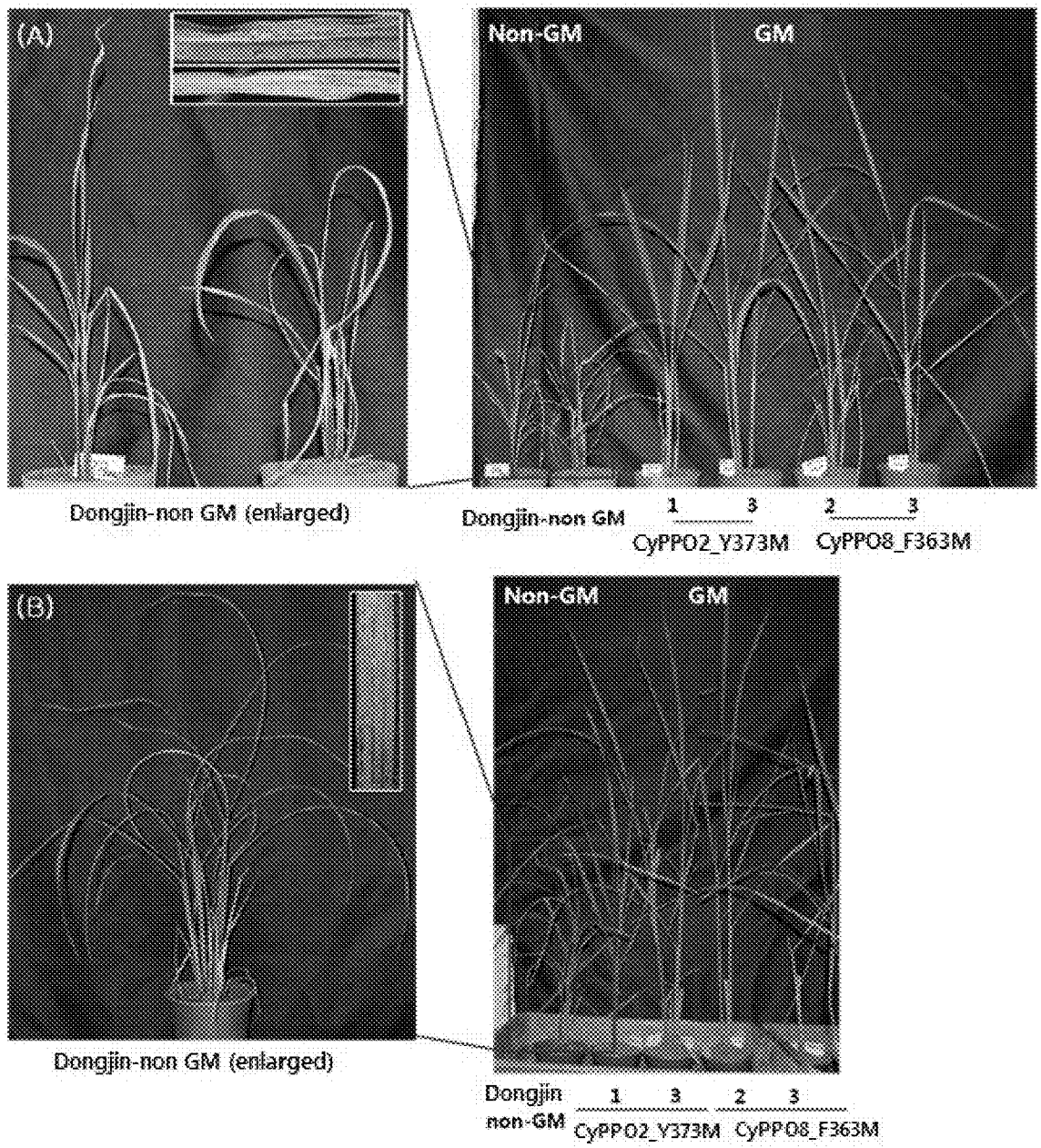

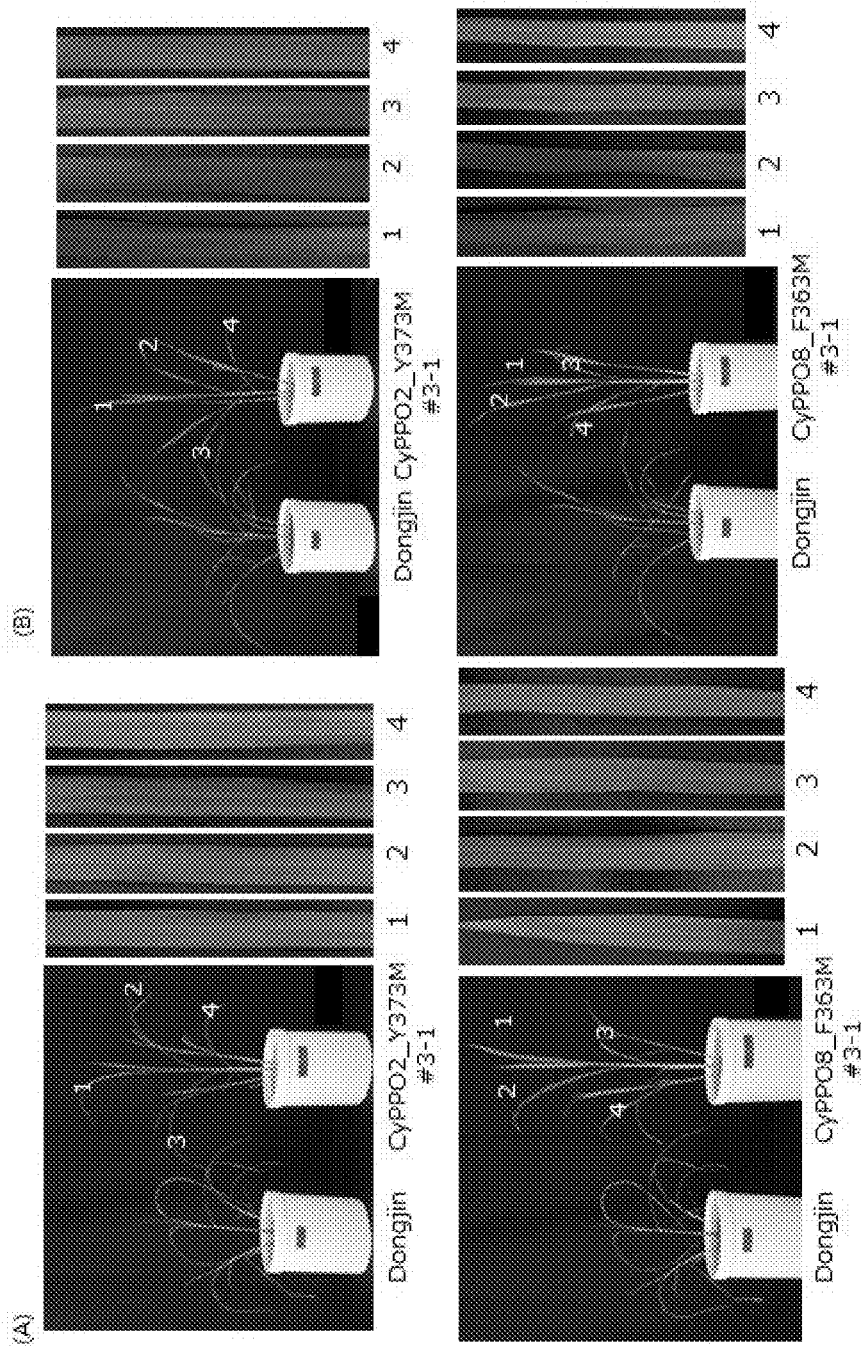
[Fig. 41]

[Fig. 42]
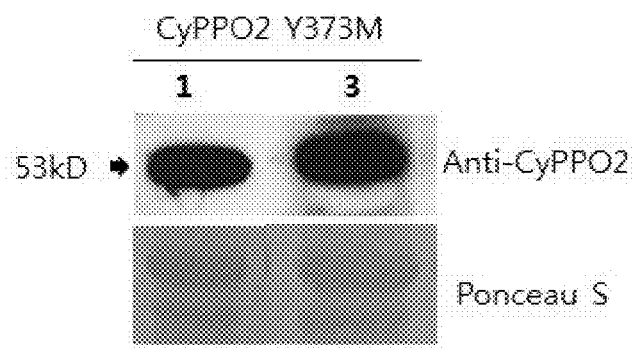
[Fig. 43]
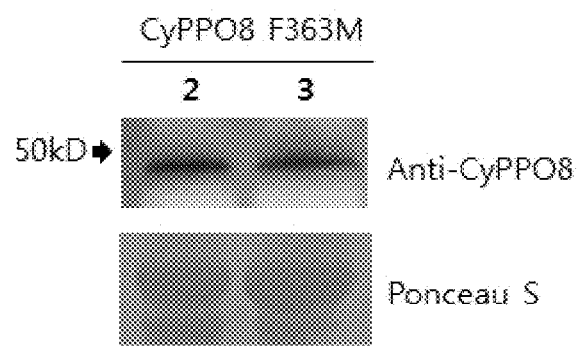

[Fig. 44]
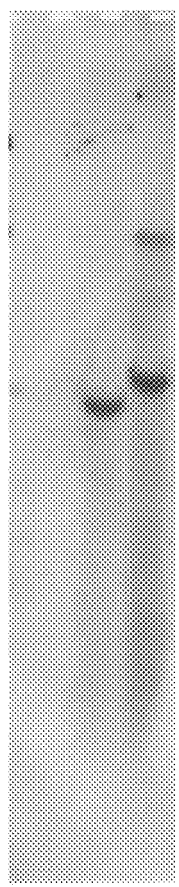

[Fig. 45]
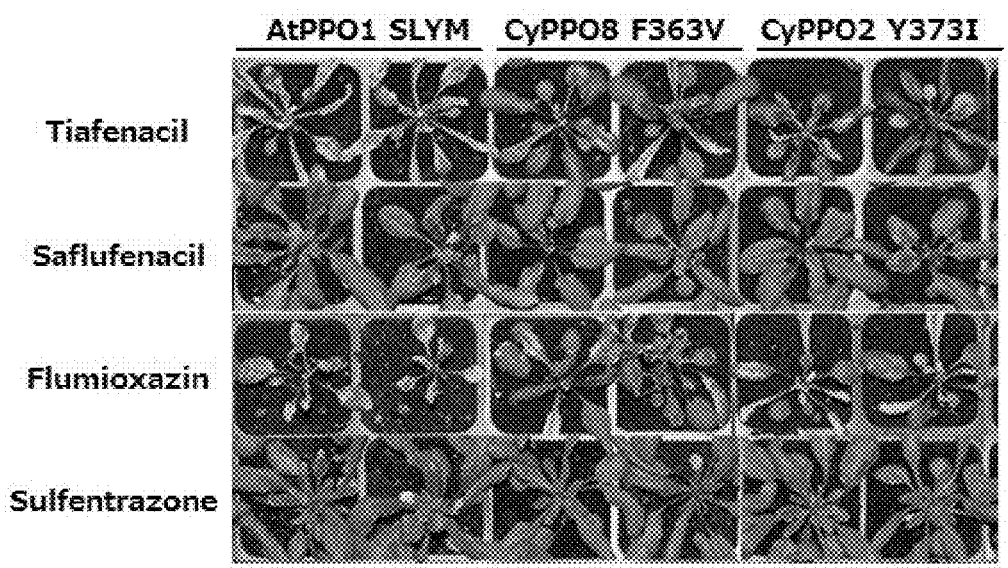

[Fig. 46]

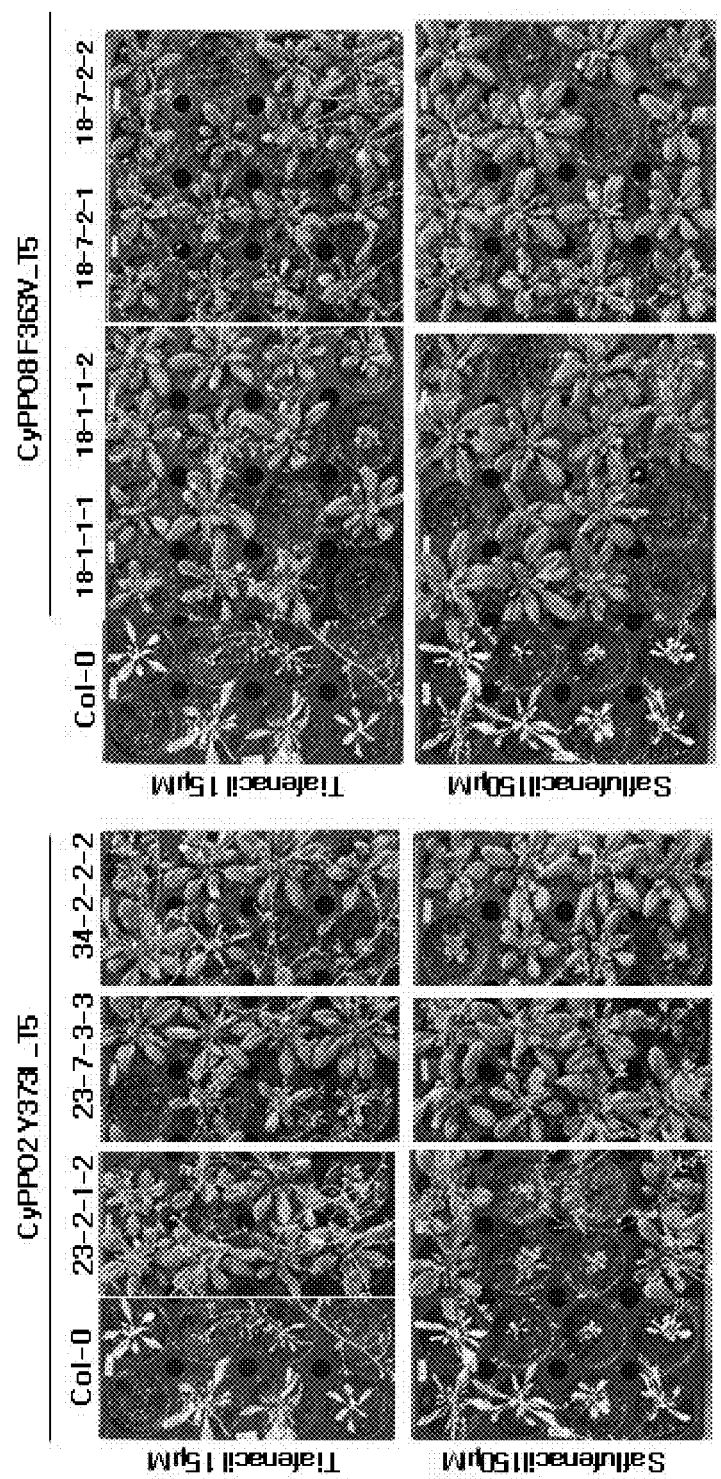
[Fig. 47]

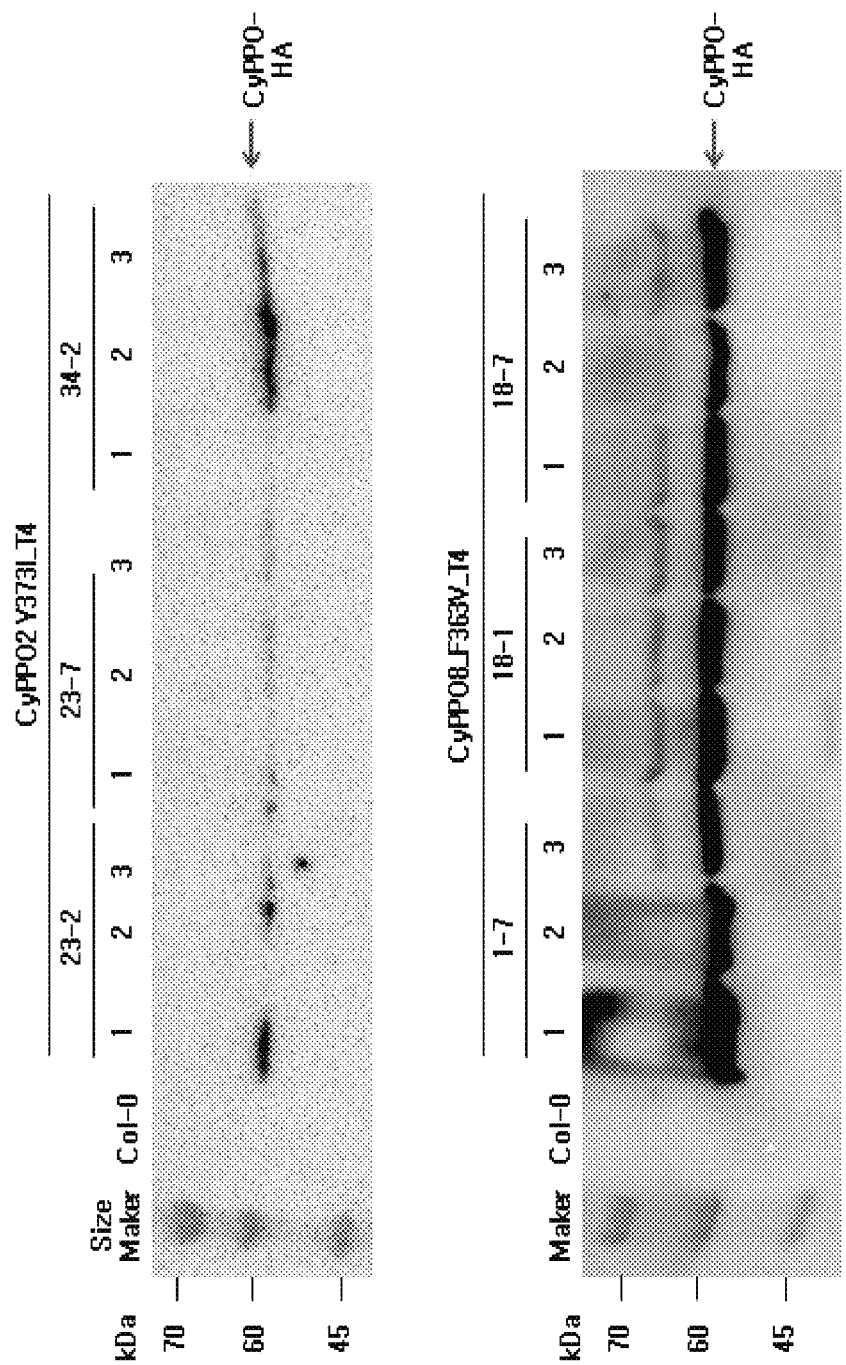
[Fig. 48]

[Fig. 49]
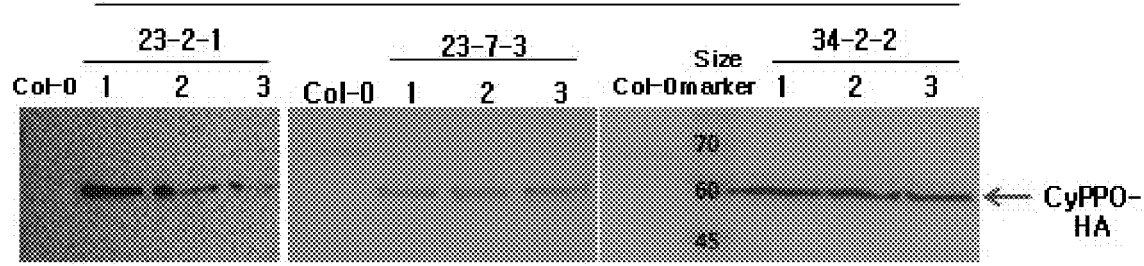
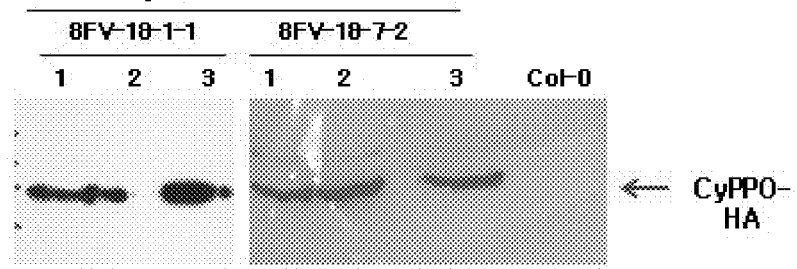

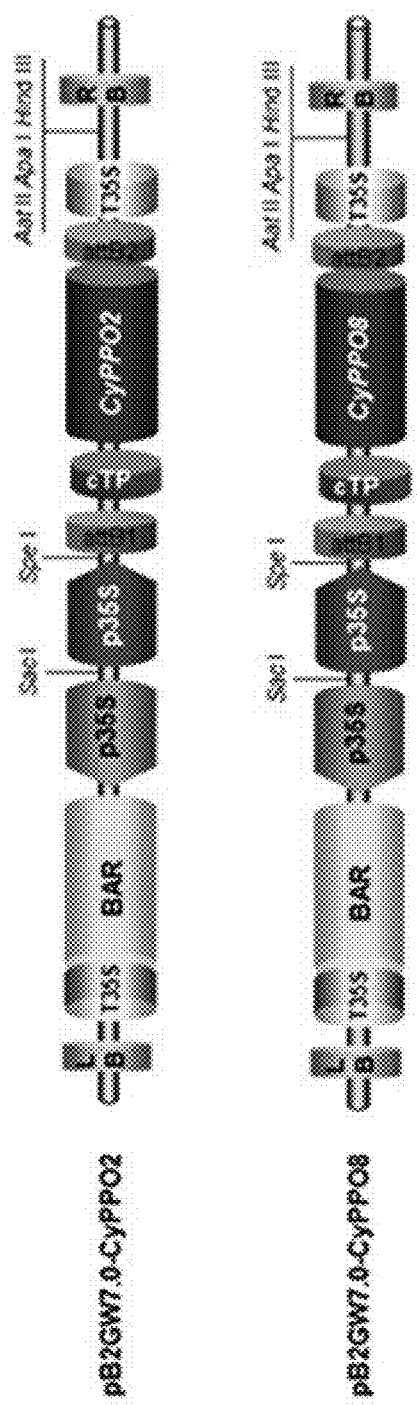
[Fig. 50]

[Fig. 51]
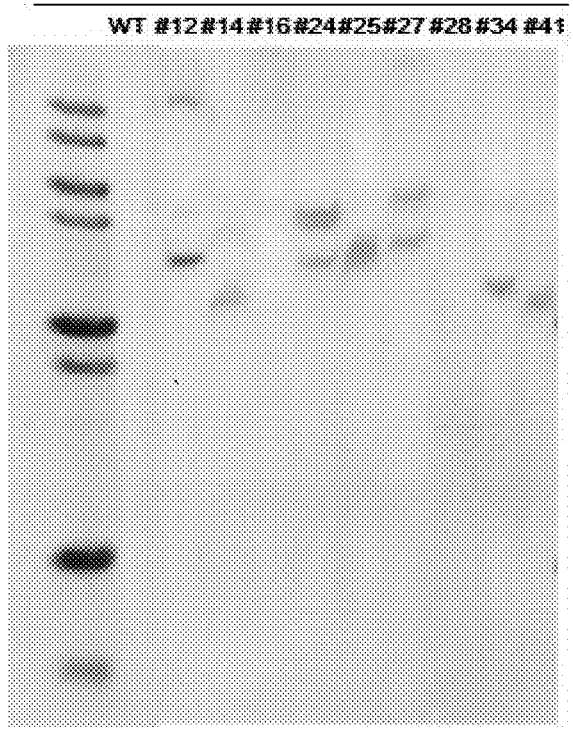
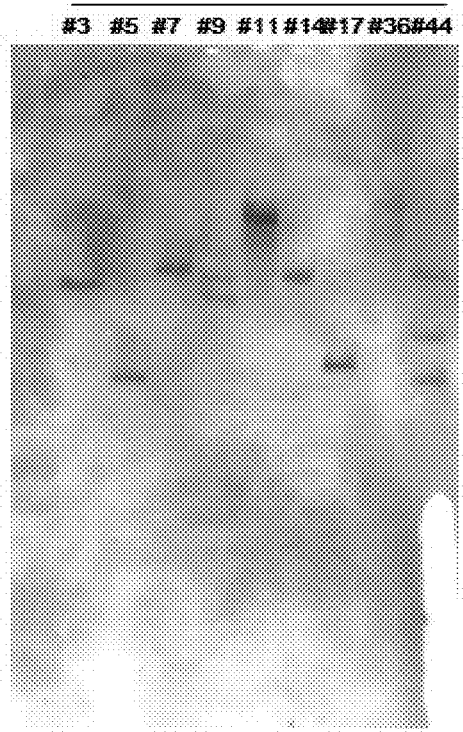

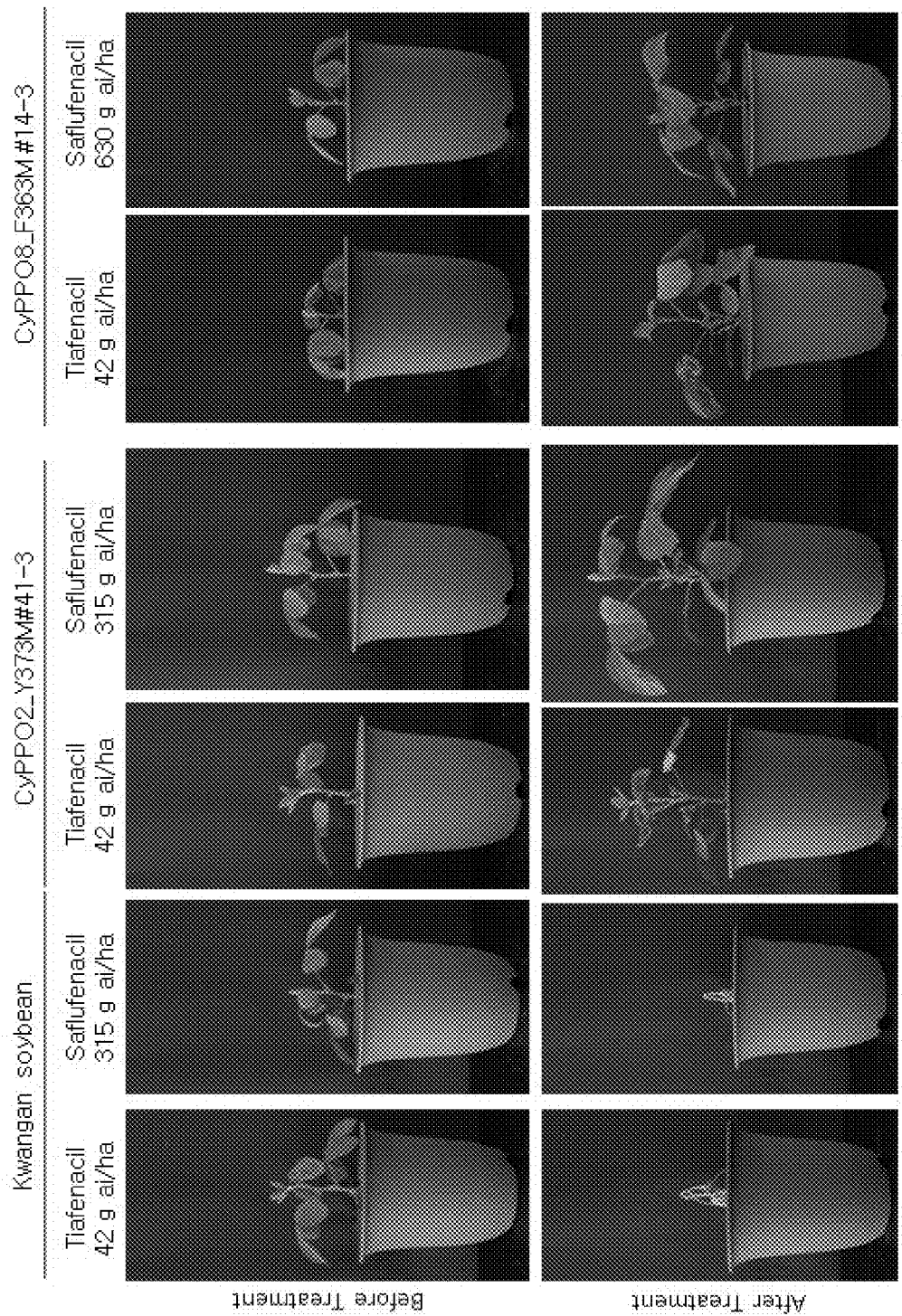
[Fig. 52]

[Fig. 53]
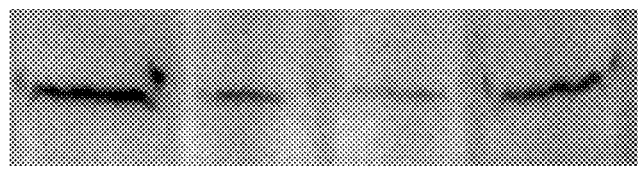
Anti-CyPPO2
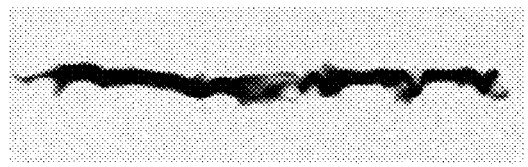
Anti-CyPPO8

[Fig. 54]
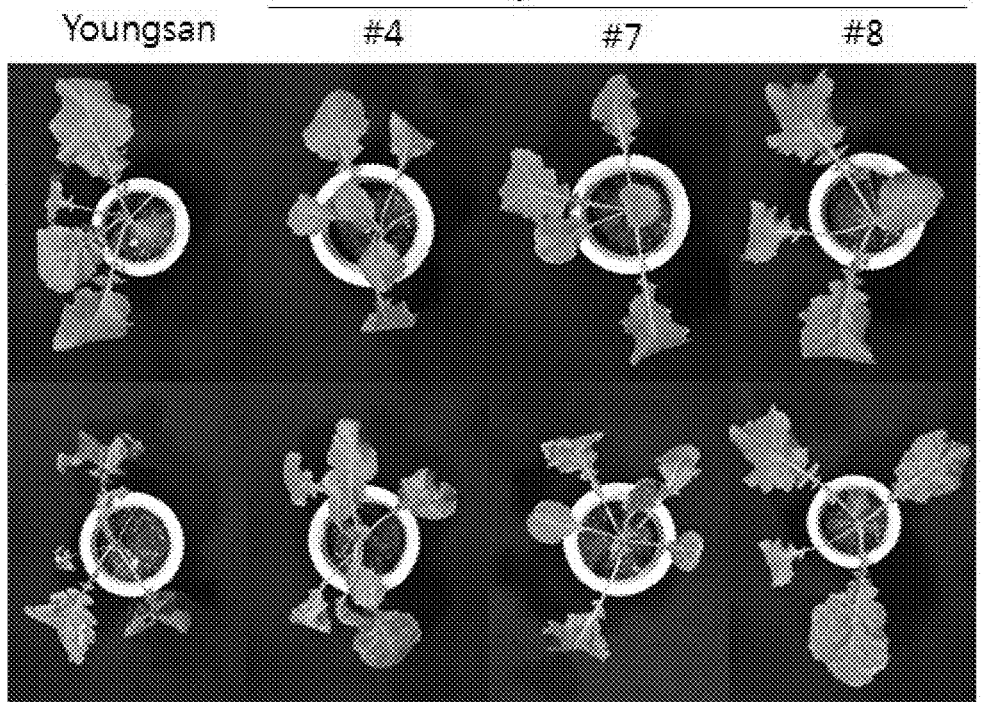

[Fig. 55]
before 10 μM Saflufenacil treatment
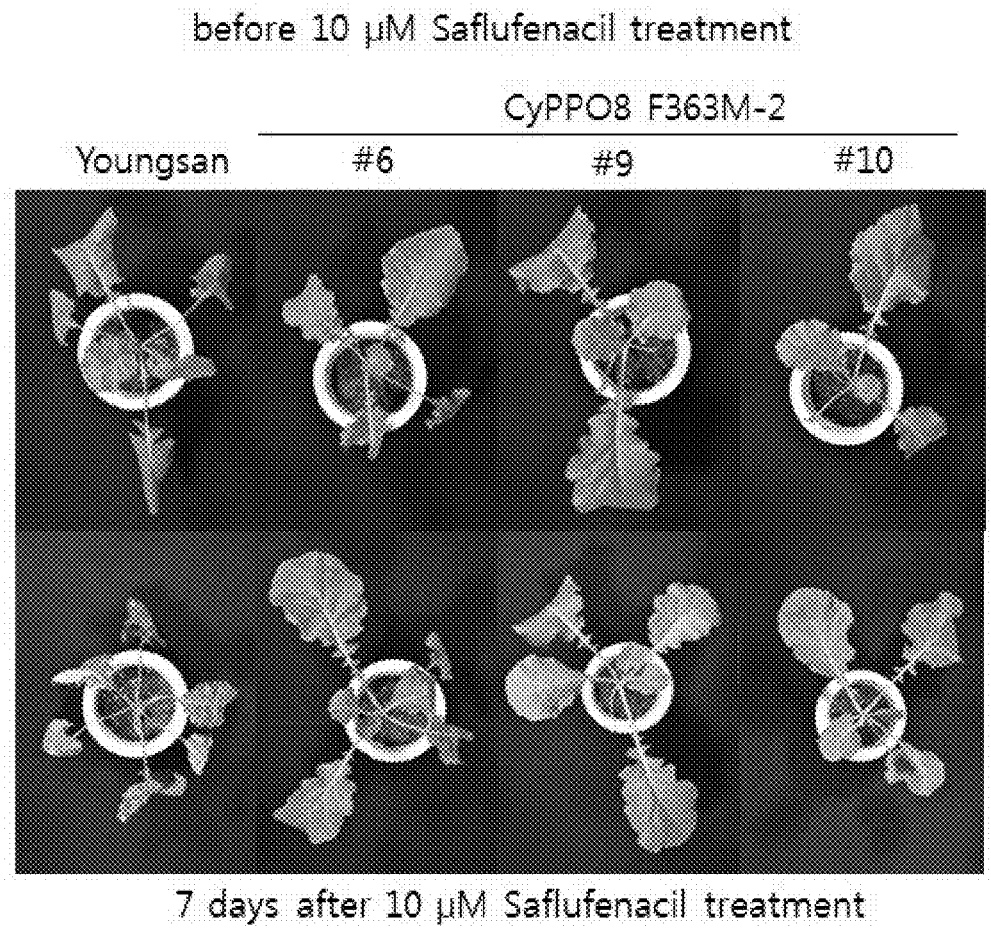
7 days after 10 μM Saflufenacil treatment
[Fig. 56]
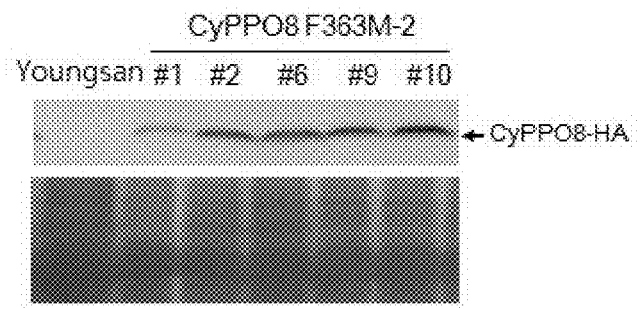

SEQUENCE LISTING

<160> NUMBER OF SEQ ID NOS: 164

<210> SEQ ID NO 1
<211> LENGTH: 486
<212> TYPE: PRT
<213> ORGANISM: Artificial Sequence
<220> FEATURE:
<223> OTHER INFORMATION: Synthetic: PPO from Oscillatoria nigroviridis
      PCC 7112, CyPPO2

<400> SEQUENCE: 1

```
Met Glu Leu Leu Asp Thr Leu Ile Val Gly Ala Gly Ile Ser Gly Leu
1               5                   10                  15

Ser Leu Ala His Ala Leu His Lys Glu Ala Thr Ser Ala Ser Pro Leu
            20                  25                  30

Lys Ile Leu Val Ala Glu Ser Gln Gly Arg Val Gly Asn Ile Thr
        35                  40                  45

Thr Val Thr Ala Glu Gly Phe Leu Trp Glu Gly Pro Asn Ser Phe
    50                  55                  60

Ser Pro Thr Pro Glu Leu Met Lys Leu Ala Val Asp Val Gly Leu Lys
65                  70                  75                  80

Gln Glu Leu Ile Phe Ala Asp Arg Lys Leu Pro Arg Phe Val Tyr Trp
            85                  90                  95

Glu Asn Lys Leu Gln Pro Val Pro Met Thr Pro Pro Ala Met Ile Gln
            100                 105                 110

Ser Gln Leu Leu Ser Phe Pro Gly Lys Leu Arg Ala Leu Phe Gly Ala
            115                 120                 125

Leu Gly Phe Val Ala Pro Ala Met Gly Asp Arg Leu Ser Gln Gln Gly
        130                 135                 140

Asn Glu Glu Thr Val Ser Gln Phe Phe Arg Arg His Leu Gly Thr Glu
145                 150                 155                 160

Val Met Gln Arg Leu Val Glu Pro Phe Val Ser Gly Val Tyr Ala Gly
            165                 170                 175

Asp Pro Gln Gln Leu Ser Ala Ala Ala Ala Phe Gly Arg Val Ala Lys
            180                 185                 190

Met Ala Asp Val Gly Gly Gly Leu Val Ala Gly Ala Leu Leu Ser Ala
        195                 200                 205

Lys Asn Arg Pro Lys Lys Met Pro Ala Asp Pro Asn Val Pro Lys Thr
210                 215                 220

Lys Pro Gly Glu Leu Gly Ser Phe Lys Gln Gly Leu Lys Ala Leu Pro
225                 230                 235                 240

Glu Ala Ile Ala Ala Lys Leu Gly Asp Arg Val Lys Leu Asn Trp His
            245                 250                 255

Leu Thr Arg Leu Gln Arg Thr Glu Arg Glu Thr Tyr Ile Ala Glu Phe
            260                 265                 270

Ser Thr Pro Asp Gly Gln Gln Glu Val Glu Ala Arg Thr Val Val Leu
            275                 280                 285

Thr Thr Pro Ala Tyr Val Thr Ala Asp Leu Leu Gln Pro Leu Glu Pro
        290                 295                 300

Gln Val Ser Ser Ala Leu Gln Ala Phe Thr Tyr Pro Thr Val Ala Ser
305                 310                 315                 320

Val Val Leu Ala Tyr Pro Gln Ser Asp Val Lys Gly Lys Leu Val Gly
            325                 330                 335

Phe Gly Asn Leu Ile Pro Arg Gly Gln Gly Ile Arg Cys Leu Gly Thr
            340                 345                 350
```

```
Ile Trp Thr Ser Ser Leu Phe Pro Asp Arg Ala Pro Ala Gly Trp Gln
            355                 360                 365

Thr Leu Thr Ser Tyr Ile Gly Gly Ala Thr Asp Ser Glu Ile Gly Asn
    370                 375                 380

Leu Asp Ser Glu Gln Ile Val Arg Glu Val His Arg Asp Leu Ser Arg
385                 390                 395                 400

Ile Leu Leu Lys Pro Asp Val Pro Gln Pro Lys Val Leu Thr Val Lys
                405                 410                 415

Leu Trp Lys Arg Ala Ile Pro Gln Tyr Asn Leu Gly His Phe Asp Arg
            420                 425                 430

Leu Gln Gln Ile Asp Glu Gly Leu Lys Ser Leu Pro Gly Val Tyr Leu
        435                 440                 445

Cys Ser Asn Tyr Val Gly Gly Val Ala Leu Gly Asp Cys Val Arg Arg
    450                 455                 460

Gly Phe Asp Arg Ala Arg Glu Val Gly Glu Tyr Leu Gln Lys Lys Gln
465                 470                 475                 480

Ser Asp Thr Arg Ser Ile
            485
```

<210> SEQ ID NO 2
<211> LENGTH: 1461
<212> TYPE: DNA
<213> ORGANISM: Artificial Sequence
<220> FEATURE:
<223> OTHER INFORMATION: Synthetic: CyPPO2 coding gene

<400> SEQUENCE: 2

| | | | | | |
|---|---|---|---|---|---|
| atggaactat | tagataccct | gattgtgggt | gcgggtatta | gcggtttgag | tttggcgcac | 60 |
| gcacttcaca | aggaagcaac | gagtgcatcg | ccgctgaaga | ttttagtcgc | tgagagtcag | 120 |
| ggacgtgtgg | gcgggaacat | cacgactgtg | acagcagagg | ggtttctctg | gaggagggc | 180 |
| ccgaacagtt | tttcgccgac | gccgaaattg | atgaagttgg | ctgtggatgt | gggattgaag | 240 |
| caggagttga | tttttgccga | tcgcaaattg | cctcgttttg | tgtattggga | aaataagctg | 300 |
| caaccggtgc | cgatgactcc | accggcgatg | attcagtctc | agttgctgag | ttttccgggg | 360 |
| aaactgcggg | cgttgttcgg | ggctttgggg | tttgtcgcgc | cggcaatggg | cgatcgactt | 420 |
| tcgcagcagg | gtaacgagga | aacagttcct | cattttttcc | gccgtcatct | cggtacggaa | 480 |
| gtgatgcagc | ggttggtgga | accttttgtt | tctgggggttt | atgccggcga | tccgcaacaa | 540 |
| cttagcgcgg | cggcggcttt | tggccgggta | gccaagatgg | ctgatgtggg | tggcgggctg | 600 |
| gtggcggggg | cgctgctttc | tgctaaaaac | agaccgaaga | aaatgcctgc | agacccgaat | 660 |
| gttcctaaaa | ctaagccggg | ggagttgggt | tcgttcaagc | aggggttgaa | ggctttgcca | 720 |
| gaggcgatcg | ctgctaagtt | gggcgatcga | gtgaaactca | actggcactt | gactcgcctc | 780 |
| cagcgcacag | aacgcgaaac | ttacattgct | gaattctcga | cgcccgacgg | acagcaggaa | 840 |
| gttgaggcgc | gcaccgtggt | tttgacaacg | cccgcttacg | ttacagccga | tttgttgcaa | 900 |
| cctctggaac | cgcaagttag | cagcgcttta | caagctttta | cttatcctac | ggttgcctcc | 960 |
| gttgtcttag | cataccccgca | gtcggatgtc | aagggtaaat | tagtggggttt | tggaaattta | 1020 |
| attccgaggg | ggcagggaat | tcgctgtctc | ggacgattt | ggacatcgag | tttatttccc | 1080 |
| gatcgcgcgc | ctgcagggtg | gcaaactctc | accagttaca | tcggcggggc | aacagactcg | 1140 |
| gaaattggca | atctcgactc | agaacaaatc | gttcggagg | tacaccgaga | tttgtctcgg | 1200 |
| attttgctga | aaccagatgt | gccacagcca | aagtttttaa | cggtgaagct | gtggaaacgg | 1260 |

-continued

```
gcgattcctc agtacaattt ggggcatttc gatcgcctgc aacaaatcga tgagggctta    1320
aaatctttgc ctggagtgta tttgtgcagc aactacgttg gcggagtggc tttgggagat    1380
tgcgtgcgaa ggggtttcga tcgtgcgcga gaagtgggcg agtatttgca aagaaacaa     1440 tcagatactc gatcgatctg a                                              1461
```

<210> SEQ ID NO 3
<211> LENGTH: 479
<212> TYPE: PRT
<213> ORGANISM: Artificial Sequence
<220> FEATURE:
<223> OTHER INFORMATION: Synthetic: PPO from Lyngbya sp. PCC 8106, CyPPO4

<400> SEQUENCE: 3

```
Met Thr His Val Leu Asp Ser Leu Ile Val Gly Ala Gly Ile Ser Gly
1               5                   10                  15

Leu Ala Leu Ala His Ala Leu His Gln Asn Gln Asp His Gln Leu Pro
            20                  25                  30

Leu Asn Ile Leu Val Ser Glu His Gln Gly Arg Val Gly Gly Asn Ile
        35                  40                  45

Thr Thr Val Ser Glu Gly Glu Phe Leu Trp Glu Gly Pro Asn Ser
    50                  55                  60

Phe Ser Pro Thr Pro Glu Leu Leu Lys Leu Ala Val Glu Val Gly Leu
65                  70                  75                  80

Lys Pro Glu Leu Val Phe Ala Asp Arg Lys Leu Pro Arg Tyr Val Tyr
                85                  90                  95

Trp Asn Gly Gln Leu Met Pro Val Pro Met Ser Pro Ala Leu Leu
            100                 105                 110

Ser Thr Lys Leu Leu Ser Pro Gly Gly Lys Leu Arg Ala Leu Thr Gly
        115                 120                 125

Ala Leu Gly Phe Val Gln Pro Ala Met Gly Glu Ser Leu Ser Gln Gln
    130                 135                 140

Asn Gly Glu Glu Thr Ile Ser Gln Phe Phe Glu Arg His Leu Gly Ser
145                 150                 155                 160

Glu Val Leu Lys Arg Leu Val Glu Pro Phe Val Ser Gly Val Tyr Ala
                165                 170                 175

Gly Asp Pro Gln Gln Leu Glu Ile Ser Ser Ala Phe Ala Arg Val Ala
            180                 185                 190

Arg Met Ala Tyr Ser Gly Gly Leu Val Ala Gly Ala Val Leu Ser
        195                 200                 205

Arg Arg Gln Asn Lys Ser Pro Arg Ser Pro Ala Asp Pro Ser Ile Pro
    210                 215                 220

Gln Thr Lys Arg Gly Glu Leu Gly Ser Phe Arg Gln Gly Ile Gly Ala
225                 230                 235                 240

Leu Pro Asn Ala Ile Ala Lys Gln Leu Gly Asp Gln Leu Lys Leu Asn
                245                 250                 255

Trp Gln Leu Thr Arg Leu Glu Arg Thr Glu Asn Gln Thr Tyr Arg Ala
            260                 265                 270

Glu Phe Ser Thr Pro Glu Gly Val Gln Gln Val Glu Thr Arg Thr Val
        275                 280                 285

Val Leu Thr Thr Pro Ala Tyr Val Thr Ala Glu Ile Leu Lys Pro Leu
    290                 295                 300

Gln Leu Gln Val Ser Gln Thr Leu Thr Glu Ile Pro Tyr Pro Pro Val
305                 310                 315                 320
```

```
Ala Cys Val Val Leu Ala Tyr Pro Val Ser Ala Leu Lys Gln Lys Leu
            325                 330                 335

Thr Gly Phe Gly Asn Leu Val Pro Arg Gly Gln Gly Ile Arg Thr Leu
        340                 345                 350

Gly Thr Ile Trp Thr Ser Ser Leu Phe Pro Gly Arg Ala Pro Gln Gly
            355                 360                 365

Trp Gln Val Leu Thr Ser Tyr Ile Gly Gly Ala Thr Asp Pro Glu Ile
    370                 375                 380

Gly Glu Leu Glu Asp Asp Gln Ile Val Glu Ala Val His Gln Asp Leu
385                 390                 395                 400

Arg His Ile Leu Leu Lys Glu Asp Ile Ser Pro Lys Val Leu Ala Val
                405                 410                 415

His Leu Trp Lys Arg Ala Ile Pro Gln Tyr Asn Leu Gly His Gln Gln
            420                 425                 430

Arg Leu Gln His Val Asn Glu Gly Leu Glu Ala Met Pro Gly Leu Tyr
        435                 440                 445

Leu Cys Ser Asn Tyr Ile Asp Gly Val Ala Leu Gly Asp Cys Val Arg
    450                 455                 460

Arg Ser Ile Gly Gln Ala Asn Glu Ile Leu Ser Phe Leu Gly Gln
465                 470                 475

<210> SEQ ID NO 4
<211> LENGTH: 1440
<212> TYPE: DNA
<213> ORGANISM: Artificial Sequence
<220> FEATURE:
<223> OTHER INFORMATION: Synthetic: CyPPO4 coding gene

<400> SEQUENCE: 4
atgactcacg tactcgatag tttaatcgtc ggtgcaggca ttagcggcct ggcgttagct      60
catgctctcc atcagaacca agatcatcaa ttgcctctca acattcttgt cagcgagcat     120
caaggacggg taggaggaaa atataaccac agtatccgaag gagaatttct ttgggaagaa    180
ggccccaata gttttctctc caaccccgag ttactgaagt tagcggtaga agtaggtctt     240
aagcctgagc tagtctttgc cgatcgcaag ttacctcggt acgtttactg gaatggtcaa     300
ctcatgcctg tgccgatgag tcctccggct ttgttgagta caaaactctt aagtcctgga     360
ggtaaacttc gagcattaac gggggcattg gggtttgtac aacccgcgat gggagaatcg     420
ttaagtcaac aaaatgggga agaaacgatc tcgcagtttt ttgagcgtca tttgggttca     480
gaagttctca gcgactggt tgaacccttt gtttctggtg tttatgcagg cgatccccag     540
caactcgaaa ttagctcggc ttttgcccga gtcgcacgta tggcttacag tggcggtgga     600
ttggttgctg agcggttttt atcgcgtcgt cagaacaaat ctccgcgatc gcctgccgac     660
ccgtctattc cccaaactaa acggggagag ttggggtctt ttcgtcaggg gattggagcc     720
ttacccaatg cgatcgccaa acagttaggc gatcaactca attaaactg gcaactcacc     780 cgtctcgaac ggactgaaaa ccaaacctat cgggctgaat tttcgactcc agaagggggtt   840 caacaggtag aaactcgaac ggtggtgttg acgactccgg cctatgtcac agcagaaatt     900
ctcaaaccgt gcaactcca agtcagtcaa acgttaactg aaattcccta tccccggtg      960 gcttgcgtcg ttttagccta tccgtttca gctttaaagc agaaattaac cggatttggc    1020
aatttagttc cccgaggaca agggattcgg acgttaggca cgatttggac atcgagttta   1080
tttcctggtc gcgccccca aggctggcaa gtcctcacca gttatattgg cggagcgacg    1140
gatccagaaa ttggagagtt agaagatgat caaattgttg aggcggttca tcaagatttg    1200
```

```
cgtcacattt tactcaaaga agatatctct cccaaagtgc tagccgtgca tctgtggaaa    1260
cgtgctatcc ctcaatacaa tctcggacac caacaacggt tacaacacgt taatgagggt    1320
ctagaggcaa tgccggggtt atatctgtgt agcaactata tcgacggtgt agcgttggga    1380
gattgtgtgc gtcgttctat cggacaagct aacgaaattc tcagtttttt gggtcaatag    1440
```

<210> SEQ ID NO 5
<211> LENGTH: 466
<212> TYPE: PRT
<213> ORGANISM: Artificial Sequence
<220> FEATURE:
<223> OTHER INFORMATION: Synthetic: PPO from Halothece sp. PCC 7418, CyPPO8

<400> SEQUENCE: 5

```
Met Ile Asp Thr Leu Ile Val Gly Ala Gly Ile Ser Gly Leu Ser Ala
1               5                   10                  15

Ala Tyr Arg Leu Asp Glu Lys Gln Arg Gln Val Leu Val Ala Glu Lys
            20                  25                  30

Arg Asp Arg Ala Gly Gly Asn Ile Thr Ser Gln Gln Ser Gly Asp Phe
        35                  40                  45

Leu Trp Glu Glu Gly Pro Asn Ser Phe Ser Pro Thr Pro Glu Leu Leu
    50                  55                  60

Lys Leu Ala Val Asp Ala Gly Leu Arg Asn Glu Leu Ile Phe Ala Asp
65                  70                  75                  80

Arg Gly Leu Pro Arg Tyr Val Tyr Trp Glu Gly Lys Leu Arg Pro Val
                85                  90                  95

Pro Met Ser Pro Pro Thr Ala Val Thr Ser Gln Leu Leu Ser Pro Ile
            100                 105                 110

Gly Lys Leu Arg Ala Leu Thr Gly Ala Leu Gly Phe Ile Pro Pro Gln
        115                 120                 125

Val Ser Ser Gln Glu Glu Thr Val Ala Asp Phe Phe Thr Arg His Leu
    130                 135                 140

Gly Ser Glu Val Ala Gln Arg Leu Val Ser Pro Phe Val Ser Gly Val
145                 150                 155                 160

Tyr Ala Gly Asp Val Asp Gln Leu Ser Ala Glu Ala Ala Phe Gly Arg
                165                 170                 175

Val Thr Gln Leu Ala Asp Val Gly Gly Gly Leu Val Ala Gly Ala Ile
            180                 185                 190

Leu Cys Arg Arg Gln Lys Pro Lys Ser Thr Pro Lys Thr Ala Lys Pro
        195                 200                 205

Ser Asp Ile Pro Glu Thr Lys Ser Gly Gln Leu Gly Ser Phe Lys Glu
    210                 215                 220

Gly Leu Gln Gln Leu Pro Ser Ala Ile Val Ser Gln Leu Gly Asp Lys
225                 230                 235                 240

Val Lys Phe Gln Trp Glu Leu Lys Asn Ile Ser Pro His Pro Glu Ser
                245                 250                 255

Gly Tyr Val Ala Thr Phe Ser Thr Pro Glu Gly Glu Gln Thr Val Glu
            260                 265                 270

Ala Lys Thr Val Ile Leu Thr Thr Pro Ala Tyr Val Thr Ala Ser Leu
        275                 280                 285

Val Lys Asp Leu Ser Pro Gln Ala Ser Gln Ala Leu Asn Glu Ile Ser
    290                 295                 300

Tyr Pro Pro Val Ala Cys Val Val Leu Ala Tyr Pro Asp Glu Ala Leu
305                 310                 315                 320
```

```
Arg Phe Pro Leu Lys Gly Phe Gly Asn Leu Asn Pro Arg Ser Gln Gly
                325                 330                 335

Ile Arg Thr Leu Gly Thr Ile Trp Ser Ser Thr Leu Phe Pro Gly Arg
            340                 345                 350

Thr Pro Lys Gly Trp His Leu Leu Thr Asn Phe Ile Gly Gly Ala Thr
        355                 360                 365

Asp Pro Ala Ile Ala Glu Leu Ser Glu Asp Gln Ile Ile Glu Gln Val
    370                 375                 380

His Gln Asp Leu Gln Gln Ala Val Ile Lys Ser Gly Ser Ile Pro Lys
385                 390                 395                 400

Pro Leu Ala Val His Leu Trp Ser Lys Ala Ile Pro Gln Tyr Asn Leu
                405                 410                 415

Gly His Leu Lys Arg Leu Glu Thr Ile Arg Asn His Leu Lys Pro Phe
            420                 425                 430

Ser Gly Leu Phe Leu Ser Ser Asn Tyr Leu Asp Gly Val Ala Leu Gly
        435                 440                 445

Asp Cys Val Arg Arg Gly Glu Glu Ser Ser Gln Ala Val Leu Asp Tyr
    450                 455                 460

Leu Gly
465

<210> SEQ ID NO 6
<211> LENGTH: 1401
<212> TYPE: DNA
<213> ORGANISM: Artificial Sequence
<220> FEATURE:
<223> OTHER INFORMATION: Synthetic: CyPPO8 coding gene

<400> SEQUENCE: 6
atgatagata ctttaattgt gggagcaggg attagtggtt aagtgctgc gtatcgactc     60 gatgagaagc agcgccaagt gctggttgca gaaaagcgcg atcgcgctgg ggaaatatc   120 accagccaac aaagtggcga tttcctctgg aagaaggac cgaacagttt tctcccaca    180 ccagaactcc taaaactagc ggttgatgcg ggcttaagaa atgagttaat ctttgctgat  240
cgcggacttc cccgttatgt ttattgggag gggaaactgc gccctgttcc tatgagtccc  300
cccacagccg tgacatccca gttgctgagt ccaatcggga aactacgggc gttaacgggt  360
gcattaggct ttattccccc gcaagtgtcg agtcaggaag aaacggttgc ggactttttt  420
acccgtcatc tcggttcaga agtagcccaa cggttagtga gtccgtttgt gtctggggtt  480
tatgcagggg atgtggatca actcagtgcg gaagctgcat ttggacgagt acccaactg   540 gcggatgtgg gcgtggact ggtcgcaggt gcgattttat gtcgtcgtca aaagccaaag   600
tcaaccccaa aaacggctaa accgtctgat attccagaaa caaagtctgg acagttaggt  660
tcatttaagg aaggattaca acaattaccc agcgcgatcg tttctcaact gggagacaaa  720
gtaaagtttc aatgggaact gaaaaatatc tcccctcatc cagaatcggg ttacgtcgcg  780
acattttcca caccagaggg agaacaaaca gtcgaagcca aaccgttat cctcaccact    840 cccgcctacg ttaccgcctc tctggtcaaa gatttatcac ctcaagccag tcaagcctta  900
aacgaaattt cctatcccc cgtagcttgt gtggtcttag cctatcccga tgaagccctc  960
cgttttcccc tcaaaggatt tggtaatctt aaccctcgca gtcaaggaat ccgcactctt 1020
ggtacaattt ggagttcaac actctttcca ggacgcacgc cgaaaggttg gcatctctta 1080 accaattta ttggcggtgc aactgatccc gcaattgctg aactcagtga agatcaaatt 1140
```

-continued

```
attgaacaag tccatcaaga cttacaacaa gcggtgatta aatcgggaag tatcccgaaa    1200
cccttagccg ttcatttgtg gtcaaaagcg attccgcaat acaatctcgg acatctgaaa    1260
cggttagaaa ccatccgcaa tcacttaaaa cccttctctg gactctttt atcgagtaac     1320 tatctcgatg gcgttgcgtt gggtgattgt gtgcgccgag gggaagagag tagtcaagcc    1380
gtgttagatt atttgggtta a                                              1401
```

<210> SEQ ID NO 7
<211> LENGTH: 537
<212> TYPE: PRT
<213> ORGANISM: Arabidopsis thaliana
<220> FEATURE:
<221> NAME/KEY: PEPTIDE
<222> LOCATION: (1)..(537)
<223> OTHER INFORMATION: Wild type AtPPO1

<400> SEQUENCE: 7

```
Met Glu Leu Ser Leu Leu Arg Pro Thr Thr Gln Ser Leu Leu Pro Ser
1               5                   10                  15

Phe Ser Lys Pro Asn Leu Arg Leu Asn Val Tyr Lys Pro Leu Arg Leu
                20                  25                  30

Arg Cys Ser Val Ala Gly Gly Pro Thr Val Gly Ser Ser Lys Ile Glu
            35                  40                  45

Gly Gly Gly Gly Thr Thr Ile Thr Thr Asp Cys Val Ile Val Gly Gly
        50                  55                  60

Gly Ile Ser Gly Leu Cys Ile Ala Gln Ala Leu Ala Thr Lys His Pro
65                  70                  75                  80

Asp Ala Ala Pro Asn Leu Ile Val Thr Glu Ala Lys Asp Arg Val Gly
                85                  90                  95

Gly Asn Ile Ile Thr Arg Glu Glu Asn Gly Phe Leu Trp Glu Glu Gly
            100                 105                 110

Pro Asn Ser Phe Gln Pro Ser Asp Pro Met Leu Thr Met Val Val Asp
        115                 120                 125

Ser Gly Leu Lys Asp Asp Leu Val Leu Gly Asp Pro Thr Ala Pro Arg
130                 135                 140

Phe Val Leu Trp Asn Gly Lys Leu Arg Pro Val Pro Ser Lys Leu Thr
145                 150                 155                 160

Asp Leu Pro Phe Phe Asp Leu Met Ser Ile Gly Gly Lys Ile Arg Ala
                165                 170                 175

Gly Phe Gly Ala Leu Gly Ile Arg Pro Ser Pro Pro Gly Arg Glu Glu
            180                 185                 190

Ser Val Glu Glu Phe Val Arg Arg Asn Leu Gly Asp Glu Val Phe Glu
        195                 200                 205

Arg Leu Ile Glu Pro Phe Cys Ser Gly Val Tyr Ala Gly Asp Pro Ser
210                 215                 220

Lys Leu Ser Met Lys Ala Ala Phe Gly Lys Val Trp Lys Leu Glu Gln
225                 230                 235                 240

Asn Gly Gly Ser Ile Ile Gly Gly Thr Phe Lys Ala Ile Gln Glu Arg
                245                 250                 255

Lys Asn Ala Pro Lys Ala Glu Arg Asp Pro Arg Leu Pro Lys Pro Gln
            260                 265                 270

Gly Gln Thr Val Gly Ser Phe Arg Lys Gly Leu Arg Met Leu Pro Glu
        275                 280                 285

Ala Ile Ser Ala Arg Leu Gly Ser Lys Val Lys Leu Ser Trp Lys Leu
290                 295                 300
```

Ser Gly Ile Thr Lys Leu Glu Ser Gly Gly Tyr Asn Leu Thr Tyr Glu
305                 310                 315                 320

Thr Pro Asp Gly Leu Val Ser Val Gln Ser Lys Ser Val Val Met Thr
            325                 330                 335

Val Pro Ser His Val Ala Ser Gly Leu Leu Arg Pro Leu Ser Glu Ser
            340                 345                 350

Ala Ala Asn Ala Leu Ser Lys Leu Tyr Tyr Pro Pro Val Ala Ala Val
        355                 360                 365

Ser Ile Ser Tyr Pro Lys Glu Ala Ile Arg Thr Glu Cys Leu Ile Asp
    370                 375                 380

Gly Glu Leu Lys Gly Phe Gly Gln Leu His Pro Arg Thr Gln Gly Val
385                 390                 395                 400

Glu Thr Leu Gly Thr Ile Tyr Ser Ser Ser Leu Phe Pro Asn Arg Ala
            405                 410                 415

Pro Pro Gly Arg Ile Leu Leu Leu Asn Tyr Ile Gly Gly Ser Thr Asn
            420                 425                 430

Thr Gly Ile Leu Ser Lys Ser Glu Gly Glu Leu Val Glu Ala Val Asp
        435                 440                 445

Arg Asp Leu Arg Lys Met Leu Ile Lys Pro Asn Ser Thr Asp Pro Leu
450                 455                 460

Lys Leu Gly Val Arg Val Trp Pro Gln Ala Ile Pro Gln Phe Leu Val
465                 470                 475                 480

Gly His Phe Asp Ile Leu Asp Thr Ala Lys Ser Ser Leu Thr Ser Ser
            485                 490                 495

Gly Tyr Glu Gly Leu Phe Leu Gly Gly Asn Tyr Val Ala Gly Val Ala
        500                 505                 510

Leu Gly Arg Cys Val Glu Gly Ala Tyr Glu Thr Ala Ile Glu Val Asn
    515                 520                 525

Asn Phe Met Ser Arg Tyr Ala Tyr Lys
530                 535

<210> SEQ ID NO 8
<211> LENGTH: 1614
<212> TYPE: DNA
<213> ORGANISM: Arabidopsis thaliana
<220> FEATURE:
<221> NAME/KEY: gene
<222> LOCATION: (1)..(1614)
<223> OTHER INFORMATION: Synthetic: Wild type AtPPO1

<400> SEQUENCE: 8
atggagttat ctcttctccg tccgacgact caatcgcttc ttccgtcgtt ttcgaagccc      60
aatctccgat taaatgttta taagcctctt agactccgtt gttcagtggc cggtggacca     120
accgtcggat cttcaaaaat cgaaggcgga ggaggcacca ccatcacgac ggattgtgtg     180
attgtcggcg gaggtattag tggtctttgc atcgctcagg cgcttgctac taagcatcct     240
gatgctgctc cgaatttaat tgtgaccgag gctaaggatc gtgttggagg caacattatc     300
actcgtgaag agaatggttt tctctgggaa gaaggtccca atagttttca accgtctgat     360
cctatgctca ctatggtggt agatagtggt ttgaaggatg atttggtgtt gggagatcct     420
actgcgccaa ggtttgtgtt gtggaatggg aaattgaggc cggttccatc gaagctaaca     480
gacttaccgt tctttgattt gatgagtatt ggtgggaaga ttagagctgg ttttggtgca     540
cttggcattc gaccgtcacc tccaggtcgt gaagaatctg tggaggagtt tgtacggcgt     600
aacctcggtg atgaggtttt tgagcgcctg attgaaccgt tttgttcagg tgtttatgct     660

-continued

```
ggtgatcctt caaaactgag catgaaagca gcgtttggga aggtttggaa actagagcaa    720
aatggtggaa gcataatagg tggtacttt  aaggcaattc aggagaggaa aaacgctccc    780
aaggcagaac gagacccgcg cctgccaaaa ccacagggcc aaacagttgg ttctttcagg    840
aagggacttc gaatgttgcc agaagcaata tctgcaagat taggtagcaa agttaagttg    900
tcttggaagc tctcaggtat cactaagctg gagagcggag gatacaactt aacatatgag    960
actccagatg gtttagtttc cgtgcagagc aaaagtgttg taatgacggt gccatctcat   1020
gttgcaagtg gtctcttgcg ccctcttct  gaatctgctg caaatgcact ctcaaaacta   1080
tattacccac cagttgcagc agtatctatc tcgtacccga agaagcaat  ccgaacagaa   1140 tgtttgatag atggtgaact aaagggtttt gggcaattgc atccacgcac gcaaggagtt   1200
gaaacattag gaactatcta cagctcctca ctctttccaa atcgcgcacc gcccggaaga   1260
attttgctgt tgaactacat tggcgggtct acaaacaccg gaattctgtc caagtctgaa   1320
ggtgagttag tggaagcagt tgacagagat ttgaggaaaa tgctaattaa gcctaattcg   1380
accgatccac ttaaattagg agttaggta  tggcctcaag ccattcctca gtttctagtt   1440
ggtcactttg atatccttga cacggctaaa tcatctctaa cgtcttcggg ctacgaaggg   1500
ctatttttgg gtggcaatta cgtcgctggt gtagccttag gccggtgtgt agaaggcgca   1560
tatgaaaccg cgattgaggt caacaacttc atgtcacggt acgcttacaa gtaa         1614
```

<210> SEQ ID NO 9
<211> LENGTH: 537
<212> TYPE: PRT
<213> ORGANISM: Artificial Sequence
<220> FEATURE:
<223> OTHER INFORMATION: Synthetic: Mutant type AtPPO1

<400> SEQUENCE: 9

```
Met Glu Leu Ser Leu Leu Arg Pro Thr Thr Gln Ser Leu Leu Pro Ser
1               5                   10                  15

Phe Ser Lys Pro Asn Leu Arg Leu Asn Val Tyr Lys Pro Leu Arg Leu
            20                  25                  30

Arg Cys Ser Val Ala Gly Gly Pro Thr Val Gly Ser Ser Lys Ile Glu
        35                  40                  45

Gly Gly Gly Gly Thr Thr Ile Thr Thr Asp Cys Val Ile Gly Gly
    50                  55                  60

Gly Ile Ser Gly Leu Cys Ile Ala Gln Ala Leu Ala Thr Lys His Pro
65                  70                  75                  80

Asp Ala Ala Pro Asn Leu Ile Val Thr Glu Ala Lys Asp Arg Val Gly
                85                  90                  95

Gly Asn Ile Ile Thr Arg Glu Glu Asn Gly Phe Leu Trp Glu Glu Gly
            100                 105                 110

Pro Asn Ser Phe Gln Pro Ser Asp Pro Met Leu Thr Met Val Val Asp
        115                 120                 125

Ser Gly Leu Lys Asp Asp Leu Val Leu Gly Asp Pro Thr Ala Pro Arg
    130                 135                 140

Phe Val Leu Trp Asn Gly Lys Leu Arg Pro Val Pro Ser Lys Leu Thr
145                 150                 155                 160

Asp Leu Pro Phe Phe Asp Leu Met Ser Ile Gly Gly Lys Ile Arg Ala
                165                 170                 175

Gly Phe Gly Ala Leu Gly Ile Arg Pro Ser Pro Pro Gly Arg Glu Glu
            180                 185                 190

Ser Val Glu Glu Phe Val Arg Arg Asn Leu Gly Asp Glu Val Phe Glu
```

```
            195                 200                 205
Arg Leu Ile Glu Pro Phe Cys Ser Gly Val Tyr Ala Gly Asp Pro Ser
    210                 215                 220

Lys Leu Ser Met Lys Ala Ala Phe Gly Lys Val Trp Lys Leu Glu Gln
225                 230                 235                 240

Asn Gly Gly Ser Ile Ile Gly Thr Phe Lys Ala Ile Gln Glu Arg
                245                 250                 255

Lys Asn Ala Pro Lys Ala Glu Arg Asp Pro Arg Leu Pro Lys Pro Gln
                260                 265                 270

Gly Gln Thr Val Gly Ser Phe Arg Lys Gly Leu Arg Met Leu Pro Glu
                275                 280                 285

Ala Ile Ser Ala Arg Leu Gly Ser Lys Val Lys Leu Ser Trp Lys Leu
    290                 295                 300

Leu Gly Ile Thr Lys Leu Glu Ser Gly Gly Tyr Asn Leu Thr Tyr Glu
305                 310                 315                 320

Thr Pro Asp Gly Leu Val Ser Val Gln Ser Lys Ser Val Val Met Thr
                325                 330                 335

Val Pro Ser His Val Ala Ser Gly Leu Leu Arg Pro Leu Ser Glu Ser
                340                 345                 350

Ala Ala Asn Ala Leu Ser Lys Leu Tyr Tyr Pro Pro Val Ala Ala Val
                355                 360                 365

Ser Ile Ser Tyr Pro Lys Glu Ala Ile Arg Thr Glu Cys Leu Ile Asp
    370                 375                 380

Gly Glu Leu Lys Gly Phe Gly Gln Leu His Pro Arg Thr Gln Gly Val
385                 390                 395                 400

Glu Thr Leu Gly Thr Ile Tyr Ser Ser Ser Leu Phe Pro Asn Arg Ala
                405                 410                 415

Pro Pro Gly Arg Ile Leu Leu Leu Asn Met Ile Gly Gly Ser Thr Asn
                420                 425                 430

Thr Gly Ile Leu Ser Lys Ser Glu Gly Glu Leu Val Glu Ala Val Asp
                435                 440                 445

Arg Asp Leu Arg Lys Met Leu Ile Lys Pro Asn Ser Thr Asp Pro Leu
    450                 455                 460

Lys Leu Gly Val Arg Val Trp Pro Gln Ala Ile Pro Gln Phe Leu Val
465                 470                 475                 480

Gly His Phe Asp Ile Leu Asp Thr Ala Lys Ser Ser Leu Thr Ser Ser
                485                 490                 495

Gly Tyr Glu Gly Leu Phe Leu Gly Gly Asn Tyr Val Ala Gly Val Ala
                500                 505                 510

Leu Gly Arg Cys Val Glu Gly Ala Tyr Glu Thr Ala Ile Glu Val Asn
                515                 520                 525

Asn Phe Met Ser Arg Tyr Ala Tyr Lys
                530                 535

<210> SEQ ID NO 10
<211> LENGTH: 156
<212> TYPE: DNA
<213> ORGANISM: Artificial Sequence
<220> FEATURE:
<223> OTHER INFORMATION: Synthetic: cTP(chloroplast transit peptide)

<400> SEQUENCE: 10
atggagttat ctcttctccg tccgacgact caatcgcttc ttccgtcgtt ttcgaagccc      60
aatctccgat taaatgttta taagcctctt agactccgtt gttcagtggc cggtggacca     120
```
accgtcggat cttcaaaaat cgaaggcgga ggaggc         156

<210> SEQ ID NO 11
<211> LENGTH: 72
<212> TYPE: DNA
<213> ORGANISM: Artificial Sequence
<220> FEATURE:
<223> OTHER INFORMATION: Synthetic: HA(hemaglutinin) tag

<400> SEQUENCE: 11
atgtatcctt atgatgttcc agattatgct agtcttatgt acccatacga cgtgcctgac    60
tacgcatcat tg                                                        72

<210> SEQ ID NO 12
<211> LENGTH: 30
<212> TYPE: DNA
<213> ORGANISM: Artificial Sequence
<220> FEATURE:
<223> OTHER INFORMATION: Synthetic: CyPPO2_F primer

<400> SEQUENCE: 12
ccccggatcc atggaacttc ttgatactct                                     30

<210> SEQ ID NO 13
<211> LENGTH: 30
<212> TYPE: DNA
<213> ORGANISM: Artificial Sequence
<220> FEATURE:
<223> OTHER INFORMATION: Synthetic: CyPPO2_R primer

<400> SEQUENCE: 13 cccccctcgag gattgacctg gtatcactct                                    30

<210> SEQ ID NO 14
<211> LENGTH: 30
<212> TYPE: DNA
<213> ORGANISM: Artificial Sequence
<220> FEATURE:
<223> OTHER INFORMATION: Synthetic: CyPPO4_F primer

<400> SEQUENCE: 14
ccccggatcc atgacccatg ttttggattc                                     30

<210> SEQ ID NO 15
<211> LENGTH: 35
<212> TYPE: DNA
<213> ORGANISM: Artificial Sequence
<220> FEATURE:
<223> OTHER INFORMATION: Synthetic: CyPPO4_R primer

<400> SEQUENCE: 15 cccccctcgag ctgtcctaaa aatgataaaa tctcg                              35

<210> SEQ ID NO 16
<211> LENGTH: 33
<212> TYPE: DNA
<213> ORGANISM: Artificial Sequence
<220> FEATURE:
<223> OTHER INFORMATION: Synthetic: CyPPO8_F primer

<400> SEQUENCE: 16
ccccggatcc atgatagata ctcttatagt ggg                                 33

<210> SEQ ID NO 17
<211> LENGTH: 30

```
<212> TYPE: DNA
<213> ORGANISM: Artificial Sequence
<220> FEATURE:
<223> OTHER INFORMATION: Synthetic: CyPPO8_R primer

<400> SEQUENCE: 17 cccctcgag tcctaagtaa tctaaaactg                                       30

<210> SEQ ID NO 18
<211> LENGTH: 30
<212> TYPE: DNA
<213> ORGANISM: Artificial Sequence
<220> FEATURE:
<223> OTHER INFORMATION: Synthetic: Forward primer for CyPPO2_Y373M

<400> SEQUENCE: 18
gacctctatg attggtggag ctactgatag                                      30

<210> SEQ ID NO 19
<211> LENGTH: 30
<212> TYPE: DNA
<213> ORGANISM: Artificial Sequence
<220> FEATURE:
<223> OTHER INFORMATION: Synthetic: Reverse primer for CyPPO2_Y373M

<400> SEQUENCE: 19
accaatcata gaggtcaatg tttgccatcc                                      30

<210> SEQ ID NO 20
<211> LENGTH: 30
<212> TYPE: DNA
<213> ORGANISM: Artificial Sequence
<220> FEATURE:
<223> OTHER INFORMATION: Synthetic: Forward primer for CyPPO2_Y373V

<400> SEQUENCE: 20
gacctctgtg attggtggag ctactgatag                                      30

<210> SEQ ID NO 21
<211> LENGTH: 30
<212> TYPE: DNA
<213> ORGANISM: Artificial Sequence
<220> FEATURE:
<223> OTHER INFORMATION: Synthetic: Reverse primer for CyPPO2_Y373V

<400> SEQUENCE: 21
accaatcaca gaggtcaatg tttgccatcc                                      30

<210> SEQ ID NO 22
<211> LENGTH: 30
<212> TYPE: DNA
<213> ORGANISM: Artificial Sequence
<220> FEATURE:
<223> OTHER INFORMATION: Synthetic: Forward primer for CyPPO2_Y373I

<400> SEQUENCE: 22
gacctctatc attggtggag ctactgatag                                      30

<210> SEQ ID NO 23
<211> LENGTH: 30
<212> TYPE: DNA
<213> ORGANISM: Artificial Sequence
<220> FEATURE:
<223> OTHER INFORMATION: Synthetic: Reverse primer for CyPPO2_Y373I

<400> SEQUENCE: 23
```

-continued accaatgata gaggtcaatg tttgccatcc                                           30

<210> SEQ ID NO 24
<211> LENGTH: 30
<212> TYPE: DNA
<213> ORGANISM: Artificial Sequence
<220> FEATURE:
<223> OTHER INFORMATION: Synthetic: Forward primer for CyPPO2_Y373T

<400> SEQUENCE: 24
gacctctaca attggtggag ctactgatag                                           30

<210> SEQ ID NO 25
<211> LENGTH: 30
<212> TYPE: DNA
<213> ORGANISM: Artificial Sequence
<220> FEATURE:
<223> OTHER INFORMATION: Synthetic: Reverse primer for CyPPO2_Y373T

<400> SEQUENCE: 25
accaattgta gaggtcaatg tttgccatcc                                           30

<210> SEQ ID NO 26
<211> LENGTH: 30
<212> TYPE: DNA
<213> ORGANISM: Artificial Sequence
<220> FEATURE:
<223> OTHER INFORMATION: Synthetic: Forward primer for CyPPO2_Y373L

<400> SEQUENCE: 26
gacctctttg attggtggag ctactgatag                                           30

<210> SEQ ID NO 27
<211> LENGTH: 30
<212> TYPE: DNA
<213> ORGANISM: Artificial Sequence
<220> FEATURE:
<223> OTHER INFORMATION: Synthetic: Reverse primer for CyPPO2_Y373L

<400> SEQUENCE: 27
accaatcaaa gaggtcaatg tttgccatcc                                           30

<210> SEQ ID NO 28
<211> LENGTH: 30
<212> TYPE: DNA
<213> ORGANISM: Artificial Sequence
<220> FEATURE:
<223> OTHER INFORMATION: Synthetic: Forward primer for CyPPO2_Y373C

<400> SEQUENCE: 28
gacctcttgt attggtggag ctactgatag                                           30

<210> SEQ ID NO 29
<211> LENGTH: 30
<212> TYPE: DNA
<213> ORGANISM: Artificial Sequence
<220> FEATURE:
<223> OTHER INFORMATION: Synthetic: Reverse primer for CyPPO2_Y373C

<400> SEQUENCE: 29
accaatacaa gaggtcaatg tttgccatcc                                           30

<210> SEQ ID NO 30
<211> LENGTH: 30
<212> TYPE: DNA
<213> ORGANISM: Artificial Sequence

```
<220> FEATURE:
<223> OTHER INFORMATION: Synthetic: Forward primer for CyPPO2_A175C

<400> SEQUENCE: 30
ggtgtgtact gtggagatcc tcaacagctc                                              30

<210> SEQ ID NO 31
<211> LENGTH: 30
<212> TYPE: DNA
<213> ORGANISM: Artificial Sequence
<220> FEATURE:
<223> OTHER INFORMATION: Synthetic: Reverse primer forCyPPO2_ A175C

<400> SEQUENCE: 31
aggatctcca cagtacacac cagaaacaaa                                              30

<210> SEQ ID NO 32
<211> LENGTH: 30
<212> TYPE: DNA
<213> ORGANISM: Artificial Sequence
<220> FEATURE:
<223> OTHER INFORMATION: Synthetic: Forward primer for CyPPO2_A175L

<400> SEQUENCE: 32
ggtgtgtact tgggagatcc tcaacagctc                                              30

<210> SEQ ID NO 33
<211> LENGTH: 30
<212> TYPE: DNA
<213> ORGANISM: Artificial Sequence
<220> FEATURE:
<223> OTHER INFORMATION: Synthetic: Reverse primer for CyPPO2_A175L

<400> SEQUENCE: 33
aggatctccc aagtacacac cagaaacaaa                                              30

<210> SEQ ID NO 34
<211> LENGTH: 30
<212> TYPE: DNA
<213> ORGANISM: Artificial Sequence
<220> FEATURE:
<223> OTHER INFORMATION: Synthetic: Forward primer for CyPPO2_V318M

<400> SEQUENCE: 34
tatccaacaa tggcttcagt tgtgttggca                                              30

<210> SEQ ID NO 35
<211> LENGTH: 30
<212> TYPE: DNA
<213> ORGANISM: Artificial Sequence
<220> FEATURE:
<223> OTHER INFORMATION: Synthetic: Reverse primer for CyPPO2_V318M

<400> SEQUENCE: 35
aactgaagcc attgttggat aagtgaatgc                                              30

<210> SEQ ID NO 36
<211> LENGTH: 30
<212> TYPE: DNA
<213> ORGANISM: Artificial Sequence
<220> FEATURE:
<223> OTHER INFORMATION: Synthetic: Forward primer for CyPPO2_G351A

<400> SEQUENCE: 36
cgctgtctcg ctacgatttg gacatcgagt                                              30
```

<210> SEQ ID NO 37
<211> LENGTH: 30
<212> TYPE: DNA
<213> ORGANISM: Artificial Sequence
<220> FEATURE:
<223> OTHER INFORMATION: Synthetic: Reverse primer for CyPPO2_G351A

<400> SEQUENCE: 37
ccaaatcgta gcgagacagc gaattccctg                                    30

<210> SEQ ID NO 38
<211> LENGTH: 32
<212> TYPE: DNA
<213> ORGANISM: Artificial Sequence
<220> FEATURE:
<223> OTHER INFORMATION: Synthetic: Forward primer for CyPPO2_S63T

<400> SEQUENCE: 38
gcccgaacac tttttcgccg acgccggaat tg                                 32

<210> SEQ ID NO 39
<211> LENGTH: 30
<212> TYPE: DNA
<213> ORGANISM: Artificial Sequence
<220> FEATURE:
<223> OTHER INFORMATION: Synthetic: Reverse primer for CyPPO2_S63T

<400> SEQUENCE: 39
ggcgaaaaag tgttcgggcc ctcctcccag                                    30

<210> SEQ ID NO 40
<211> LENGTH: 34
<212> TYPE: DNA
<213> ORGANISM: Artificial Sequence
<220> FEATURE:
<223> OTHER INFORMATION: Synthetic: Forward primer for CyPPO2_R92A

<400> SEQUENCE: 40
caaattgcct gcttttgtgt attgggaaaa taag                               34

<210> SEQ ID NO 41
<211> LENGTH: 30
<212> TYPE: DNA
<213> ORGANISM: Artificial Sequence
<220> FEATURE:
<223> OTHER INFORMATION: Synthetic: Reverse primer for CyPPO2_R92A

<400> SEQUENCE: 41
atacacaaaa gcaggcaatt tgcgatcggc                                    30

<210> SEQ ID NO 42
<211> LENGTH: 31
<212> TYPE: DNA
<213> ORGANISM: Artificial Sequence
<220> FEATURE:
<223> OTHER INFORMATION: Synthetic: Forward primer for CyPPO2_V173S

<400> SEQUENCE: 42
gtttctggga gttatgccgg cgatccgcaa c                                  31

<210> SEQ ID NO 43
<211> LENGTH: 30
<212> TYPE: DNA
<213> ORGANISM: Artificial Sequence
<220> FEATURE:
<223> OTHER INFORMATION: Synthetic: Reverse primer for CyPPO2_V173S

<400> SEQUENCE: 43
ccggcataac tcccagaaac aaaaggttcc                                    30

<210> SEQ ID NO 44
<211> LENGTH: 31
<212> TYPE: DNA
<213> ORGANISM: Artificial Sequence
<220> FEATURE:
<223> OTHER INFORMATION: Synthetic: Forward primer for CyPPO2_V173C

<400> SEQUENCE: 44
gtttctgggt gttatgccgg cgatccgcaa c                                  31

<210> SEQ ID NO 45
<211> LENGTH: 32
<212> TYPE: DNA
<213> ORGANISM: Artificial Sequence
<220> FEATURE:
<223> OTHER INFORMATION: Synthetic: Reverse primer for CyPPO2_V173C

<400> SEQUENCE: 45
ccggcataac acccagaaac aaaaggttcc ac                                 32

<210> SEQ ID NO 46
<211> LENGTH: 31
<212> TYPE: DNA
<213> ORGANISM: Artificial Sequence
<220> FEATURE:
<223> OTHER INFORMATION: Synthetic: Forward primer for CyPPO2_V173T

<400> SEQUENCE: 46
gtttctggga cttatgccgg cgatccgcaa c                                  31

<210> SEQ ID NO 47
<211> LENGTH: 32
<212> TYPE: DNA
<213> ORGANISM: Artificial Sequence
<220> FEATURE:
<223> OTHER INFORMATION: Synthetic: Reverse primer for CyPPO2_V173T

<400> SEQUENCE: 47
ccggcataag tcccagaaac aaaaggttcc ac                                 32

<210> SEQ ID NO 48
<211> LENGTH: 33
<212> TYPE: DNA
<213> ORGANISM: Artificial Sequence
<220> FEATURE:
<223> OTHER INFORMATION: Synthetic: Forward primer for CyPPO2_L229F

<400> SEQUENCE: 48
actaagccgg gggagttcgg ttcgttcaag cag                                33

<210> SEQ ID NO 49
<211> LENGTH: 33
<212> TYPE: DNA
<213> ORGANISM: Artificial Sequence
<220> FEATURE:
<223> OTHER INFORMATION: Synthetic: Reverse primer for CyPPO2_L229F

<400> SEQUENCE: 49
ctgcttgaac gaaccgaact cccccggctt agt                                33

<210> SEQ ID NO 50

-continued

```
<211> LENGTH: 30
<212> TYPE: DNA
<213> ORGANISM: Artificial Sequence
<220> FEATURE:
<223> OTHER INFORMATION: Synthetic: Forward primer for CyPPO2_L340I

<400> SEQUENCE: 50
ttttggaaat ataattccga gggggcaggg                                        30

<210> SEQ ID NO 51
<211> LENGTH: 34
<212> TYPE: DNA
<213> ORGANISM: Artificial Sequence
<220> FEATURE:
<223> OTHER INFORMATION: Synthetic: Reverse primer for CyPPO2_L340I

<400> SEQUENCE: 51
ctcggaatta tatttccaaa acccactaat ttac                                   34

<210> SEQ ID NO 52
<211> LENGTH: 31
<212> TYPE: DNA
<213> ORGANISM: Artificial Sequence
<220> FEATURE:
<223> OTHER INFORMATION: Synthetic: Forward primer for CyPPO2_I353T

<400> SEQUENCE: 52
tcgggacgac ttggacatcg agtttatttc c                                      31

<210> SEQ ID NO 53
<211> LENGTH: 31
<212> TYPE: DNA
<213> ORGANISM: Artificial Sequence
<220> FEATURE:
<223> OTHER INFORMATION: Synthetic: Reverse primer for CyPPO2_I353T

<400> SEQUENCE: 53
gatgtccaag tcgtcccgag acagcgaatt c                                      31

<210> SEQ ID NO 54
<211> LENGTH: 30
<212> TYPE: DNA
<213> ORGANISM: Artificial Sequence
<220> FEATURE:
<223> OTHER INFORMATION: Synthetic: Forward primer for CyPPO2_I353L

<400> SEQUENCE: 54
ctcgggacgc tttggacatc gagtttattt                                        30

<210> SEQ ID NO 55
<211> LENGTH: 30
<212> TYPE: DNA
<213> ORGANISM: Artificial Sequence
<220> FEATURE:
<223> OTHER INFORMATION: Synthetic: Reverse primer for CyPPO2_I353L

<400> SEQUENCE: 55
atgtccaaag cgtcccgaga cagcgaattc                                        30

<210> SEQ ID NO 56
<211> LENGTH: 33
<212> TYPE: DNA
<213> ORGANISM: Artificial Sequence
<220> FEATURE:
<223> OTHER INFORMATION: Synthetic: Forward primer for CyPPO2_I353V

<400> SEQUENCE: 56
```

```
actaagccgg gggagttcgg ttcgttcaag cag                                    33
```

<210> SEQ ID NO 57
<211> LENGTH: 33
<212> TYPE: DNA
<213> ORGANISM: Artificial Sequence
<220> FEATURE:
<223> OTHER INFORMATION: Synthetic: Reverse primer for CyPPO2_I353V

<400> SEQUENCE: 57

```
ctgcttgaac gaaccgaact cccccggctt agt                                    33
```

<210> SEQ ID NO 58
<211> LENGTH: 31
<212> TYPE: DNA
<213> ORGANISM: Artificial Sequence
<220> FEATURE:
<223> OTHER INFORMATION: Synthetic: Forward primer for CyPPO2_I353C

<400> SEQUENCE: 58

```
tcgggacgtg ttggacatcg agtttatttc c                                      31
```

<210> SEQ ID NO 59
<211> LENGTH: 31
<212> TYPE: DNA
<213> ORGANISM: Artificial Sequence
<220> FEATURE:
<223> OTHER INFORMATION: Synthetic: Reverse primer for CyPPO2_I353C

<400> SEQUENCE: 59

```
gatgtccaac acgtcccgag acagcgaatt c                                      31
```

<210> SEQ ID NO 60
<211> LENGTH: 30
<212> TYPE: DNA
<213> ORGANISM: Artificial Sequence
<220> FEATURE:
<223> OTHER INFORMATION: Synthetic: Forward primer for CyPPO2_V318T

<400> SEQUENCE: 60

```
tatcctacga ctgcctccgt tgtcttagca                                        30
```

<210> SEQ ID NO 61
<211> LENGTH: 30
<212> TYPE: DNA
<213> ORGANISM: Artificial Sequence
<220> FEATURE:
<223> OTHER INFORMATION: Synthetic: Reverse primer for CyPPO2_V318T

<400> SEQUENCE: 61

```
aacggaggca gtcgtaggat aagtaaaagc                                        30
```

<210> SEQ ID NO 62
<211> LENGTH: 33
<212> TYPE: DNA
<213> ORGANISM: Artificial Sequence
<220> FEATURE:
<223> OTHER INFORMATION: Synthetic: Forward primer for CyPPO2_E228A

<400> SEQUENCE: 62

```
aaaactaagc cgggggcgtt gggttcgttc aag                                    33
```

<210> SEQ ID NO 63
<211> LENGTH: 33
<212> TYPE: DNA

```
<213> ORGANISM: Artificial Sequence
<220> FEATURE:
<223> OTHER INFORMATION: Synthetic: Reverse primer for CyPPO2_E228A

<400> SEQUENCE: 63
cttgaacgaa cccaacgccc ccggcttagt ttt                           33

<210> SEQ ID NO 64
<211> LENGTH: 30
<212> TYPE: DNA
<213> ORGANISM: Artificial Sequence
<220> FEATURE:
<223> OTHER INFORMATION: Synthetic: Forward primer for CyPPO2_P91L

<400> SEQUENCE: 64
aaacttctta gattcgtgta ttgggaaaac                               30

<210> SEQ ID NO 65
<211> LENGTH: 30
<212> TYPE: DNA
<213> ORGANISM: Artificial Sequence
<220> FEATURE:
<223> OTHER INFORMATION: Synthetic: Reverse primer for CyPPO2_P91L

<400> SEQUENCE: 65
acgaatctaa gaagttttct atctgcgaat                               30

<210> SEQ ID NO 66
<211> LENGTH: 30
<212> TYPE: DNA
<213> ORGANISM: Artificial Sequence
<220> FEATURE:
<223> OTHER INFORMATION: Synthetic: Forward primer for
      CyPPO2_P316A+V318L

<400> SEQUENCE: 66
gcttttactt atgctacgct tgcctccgtt                               30

<210> SEQ ID NO 67
<211> LENGTH: 30
<212> TYPE: DNA
<213> ORGANISM: Artificial Sequence
<220> FEATURE:
<223> OTHER INFORMATION: Synthetic: Reverse primer for
      CyPPO2_P316A+V318L

<400> SEQUENCE: 67
gacaacggag gcaagcgtag cataagtaaa                               30

<210> SEQ ID NO 68
<211> LENGTH: 30
<212> TYPE: DNA
<213> ORGANISM: Artificial Sequence
<220> FEATURE:
<223> OTHER INFORMATION: Synthetic: Forward primer for
      CyPPO2_P316L+V318L

<400> SEQUENCE: 68
gcttttactt atcttacgct tgcctccgtt                               30

<210> SEQ ID NO 69
<211> LENGTH: 30
<212> TYPE: DNA
<213> ORGANISM: Artificial Sequence
<220> FEATURE:
<223> OTHER INFORMATION: Synthetic: Reverse primer for
      CyPPO2_P316L+V318L
```

```
<400> SEQUENCE: 69
gacaacggag gcaagcgtaa gataagtaaa                                     30

<210> SEQ ID NO 70
<211> LENGTH: 32
<212> TYPE: DNA
<213> ORGANISM: Artificial Sequence
<220> FEATURE:
<223> OTHER INFORMATION: Synthetic: Forward primer for CyPPO2_F337V

<400> SEQUENCE: 70
ttagtgggtg ttggaaattt aattccgagg gg                                  32

<210> SEQ ID NO 71
<211> LENGTH: 33
<212> TYPE: DNA
<213> ORGANISM: Artificial Sequence
<220> FEATURE:
<223> OTHER INFORMATION: Synthetic: Reverse primer for CyPPO2_F337V

<400> SEQUENCE: 71
taaatttcca cacccacta atttaccctt gac                                  33

<210> SEQ ID NO 72
<211> LENGTH: 33
<212> TYPE: DNA
<213> ORGANISM: Artificial Sequence
<220> FEATURE:
<223> OTHER INFORMATION: Synthetic: Forward primer for CyPPO2_T352V

<400> SEQUENCE: 72
tgtctcgggg tgatttggac atcgagttta ttt                                 33

<210> SEQ ID NO 73
<211> LENGTH: 32
<212> TYPE: DNA
<213> ORGANISM: Artificial Sequence
<220> FEATURE:
<223> OTHER INFORMATION: Synthetic: Reverse primer for CyPPO2_T352V

<400> SEQUENCE: 73
gtccaaatca ccccgagaca gcgaattccc tg                                  32

<210> SEQ ID NO 74
<211> LENGTH: 31
<212> TYPE: DNA
<213> ORGANISM: Artificial Sequence
<220> FEATURE:
<223> OTHER INFORMATION: Synthetic: Forward primer for CyPPO2_V173L

<400> SEQUENCE: 74
gtttctgggc tttatgccgg cgatccgcaa c                                   31

<210> SEQ ID NO 75
<211> LENGTH: 31
<212> TYPE: DNA
<213> ORGANISM: Artificial Sequence
<220> FEATURE:
<223> OTHER INFORMATION: Synthetic: Reverse primer for CyPPO2_V173L

<400> SEQUENCE: 75
cggcataaag cccagaaaca aaaggttcca c                                   31

<210> SEQ ID NO 76
```

```
<211> LENGTH: 30
<212> TYPE: DNA
<213> ORGANISM: Artificial Sequence
<220> FEATURE:
<223> OTHER INFORMATION: Synthetic: Forward primer for CyPPO2_A175I

<400> SEQUENCE: 76
gtttctgggg tttatattgg cgatccgcaa                                      30

<210> SEQ ID NO 77
<211> LENGTH: 30
<212> TYPE: DNA
<213> ORGANISM: Artificial Sequence
<220> FEATURE:
<223> OTHER INFORMATION: Synthetic: Reverse primer for CyPPO2_A175I

<400> SEQUENCE: 77
ttgttgcgga tcgccaatat aaacccaga                                       30

<210> SEQ ID NO 78
<211> LENGTH: 34
<212> TYPE: DNA
<213> ORGANISM: Artificial Sequence
<220> FEATURE:
<223> OTHER INFORMATION: Synthetic: Forward primer for CyPPO2_L340V

<400> SEQUENCE: 78
ttttggaaat gttattccaa gaggtcaagg aatc                                 34

<210> SEQ ID NO 79
<211> LENGTH: 32
<212> TYPE: DNA
<213> ORGANISM: Artificial Sequence
<220> FEATURE:
<223> OTHER INFORMATION: Synthetic: Reverse primer for CyPPO2_L340V

<400> SEQUENCE: 79
cttggaataa catttccaaa acccacgagt tt                                   32

<210> SEQ ID NO 80
<211> LENGTH: 30
<212> TYPE: DNA
<213> ORGANISM: Artificial Sequence
<220> FEATURE:
<223> OTHER INFORMATION: Synthetic: Forward primer for CyPPO2_L340T

<400> SEQUENCE: 80
ttttggaaat actattccaa gaggtcaagg                                      30

<210> SEQ ID NO 81
<211> LENGTH: 34
<212> TYPE: DNA
<213> ORGANISM: Artificial Sequence
<220> FEATURE:
<223> OTHER INFORMATION: Synthetic: Reverse primer for CyPPO2_L340T

<400> SEQUENCE: 81
cttggaatag tatttccaaa acccacgagt tttc                                 34

<210> SEQ ID NO 82
<211> LENGTH: 33
<212> TYPE: DNA
<213> ORGANISM: Artificial Sequence
<220> FEATURE:
<223> OTHER INFORMATION: Synthetic: Forward primer for CyPPO2_F169A

<400> SEQUENCE: 82
```
ccagaaacag caggttccac caaccgctgc atc                                    33

<210> SEQ ID NO 83
<211> LENGTH: 31
<212> TYPE: DNA
<213> ORGANISM: Artificial Sequence
<220> FEATURE:
<223> OTHER INFORMATION: Synthetic: Reverse primer for CyPPO2_F169A

<400> SEQUENCE: 83
gtggaacctg ctgtttctgg ggtttatgcc g                                      31

<210> SEQ ID NO 84
<211> LENGTH: 30
<212> TYPE: DNA
<213> ORGANISM: Artificial Sequence
<220> FEATURE:
<223> OTHER INFORMATION: Synthetic: F primer for CyPPO4_Y375M

<400> SEQUENCE: 84
cttacatcta tgattggtgg agctaccgat                                        30

<210> SEQ ID NO 85
<211> LENGTH: 30
<212> TYPE: DNA
<213> ORGANISM: Artificial Sequence
<220> FEATURE:
<223> OTHER INFORMATION: Synthetic: R primer for CyPPO4_Y375M

<400> SEQUENCE: 85
ccaccaatca tagatgtaag aacctgccat                                        30

<210> SEQ ID NO 86
<211> LENGTH: 30
<212> TYPE: DNA
<213> ORGANISM: Artificial Sequence
<220> FEATURE:
<223> OTHER INFORMATION: Synthetic: R primer for CyPPO4_Y375V

<400> SEQUENCE: 86
cttacatctg ttattggtgg agctaccgat                                        30

<210> SEQ ID NO 87
<211> LENGTH: 30
<212> TYPE: DNA
<213> ORGANISM: Artificial Sequence
<220> FEATURE:
<223> OTHER INFORMATION: Synthetic: R primer for CyPPO4_Y375V

<400> SEQUENCE: 87
ccaccaataa cagatgtaag aacctgccat                                        30

<210> SEQ ID NO 88
<211> LENGTH: 30
<212> TYPE: DNA
<213> ORGANISM: Artificial Sequence
<220> FEATURE:
<223> OTHER INFORMATION: Synthetic: F primer for CyPPO4_Y375I

<400> SEQUENCE: 88
cttacatcta tcattggtgg agctaccgat                                        30

<210> SEQ ID NO 89
<211> LENGTH: 30
<212> TYPE: DNA

```
<213> ORGANISM: Artificial Sequence
<220> FEATURE:
<223> OTHER INFORMATION: Synthetic: R primer for CyPPO4_Y375I

<400> SEQUENCE: 89
ccaccaatga tagatgtaag aacctgccat                                          30

<210> SEQ ID NO 90
<211> LENGTH: 30
<212> TYPE: DNA
<213> ORGANISM: Artificial Sequence
<220> FEATURE:
<223> OTHER INFORMATION: Synthetic: F primer for CyPPO4_Y375T

<400> SEQUENCE: 90
cttacatcta ccattggtgg agctaccgat                                          30

<210> SEQ ID NO 91
<211> LENGTH: 30
<212> TYPE: DNA
<213> ORGANISM: Artificial Sequence
<220> FEATURE:
<223> OTHER INFORMATION: Synthetic: R primer for CyPPO4_Y375T

<400> SEQUENCE: 91
ccaccaatgg tagatgtaag aacctgccat                                          30

<210> SEQ ID NO 92
<211> LENGTH: 30
<212> TYPE: DNA
<213> ORGANISM: Artificial Sequence
<220> FEATURE:
<223> OTHER INFORMATION: Synthetic: F primer for CyPPO4_Y375C

<400> SEQUENCE: 92
cttacatctt gtattggtgg agctaccgat                                          30

<210> SEQ ID NO 93
<211> LENGTH: 30
<212> TYPE: DNA
<213> ORGANISM: Artificial Sequence
<220> FEATURE:
<223> OTHER INFORMATION: Synthetic: R primer for CyPPO4_Y375C

<400> SEQUENCE: 93
ccaccaatac aagatgtaag aacctgccat                                          30

<210> SEQ ID NO 94
<211> LENGTH: 30
<212> TYPE: DNA
<213> ORGANISM: Artificial Sequence
<220> FEATURE:
<223> OTHER INFORMATION: Synthetic: F primer for CyPPO4_A176C

<400> SEQUENCE: 94
ggtgtgtatt gtggagatcc acaacagctt                                          30

<210> SEQ ID NO 95
<211> LENGTH: 30
<212> TYPE: DNA
<213> ORGANISM: Artificial Sequence
<220> FEATURE:
<223> OTHER INFORMATION: Synthetic: R primer for CyPPO4_A176C

<400> SEQUENCE: 95
tggatctcca caatacacac cagaaacaaa                                          30
```

<210> SEQ ID NO 96
<211> LENGTH: 30
<212> TYPE: DNA
<213> ORGANISM: Artificial Sequence
<220> FEATURE:
<223> OTHER INFORMATION: Synthetic: F primer for CyPPO4_A176L

<400> SEQUENCE: 96
ggtgtgtatt tgggagatcc acaacagctt                              30

<210> SEQ ID NO 97
<211> LENGTH: 30
<212> TYPE: DNA
<213> ORGANISM: Artificial Sequence
<220> FEATURE:
<223> OTHER INFORMATION: Synthetic: R primer for CyPPO4_A176L

<400> SEQUENCE: 97
tggatctccc aaatacacac cagaaacaaa                              30

<210> SEQ ID NO 98
<211> LENGTH: 33
<212> TYPE: DNA
<213> ORGANISM: Artificial Sequence
<220> FEATURE:
<223> OTHER INFORMATION: Synthetic: F primer for CyPPO4_P318L+V320L

<400> SEQUENCE: 98
attccttatt tgccattggc ttgtgttgtg ctc                          33

<210> SEQ ID NO 99
<211> LENGTH: 34
<212> TYPE: DNA
<213> ORGANISM: Artificial Sequence
<220> FEATURE:
<223> OTHER INFORMATION: Synthetic: R primer for CyPPO4_P318L+V320L

<400> SEQUENCE: 99
aacacaagcc aatggcaaat aaggaatttc tgta                         34

<210> SEQ ID NO 100
<211> LENGTH: 30
<212> TYPE: DNA
<213> ORGANISM: Artificial Sequence
<220> FEATURE:
<223> OTHER INFORMATION: Synthetic: F primer for CyPPO4_V320M

<400> SEQUENCE: 100
tatcctccaa tggcttgtgt tgtgctcgca                              30

<210> SEQ ID NO 101
<211> LENGTH: 30
<212> TYPE: DNA
<213> ORGANISM: Artificial Sequence
<220> FEATURE:
<223> OTHER INFORMATION: Synthetic: R primer for CyPPO4_V320M

<400> SEQUENCE: 101
aacacaagcc attggaggat aaggaatttc                              30

<210> SEQ ID NO 102
<211> LENGTH: 33
<212> TYPE: DNA
<213> ORGANISM: Artificial Sequence
<220> FEATURE:

<223> OTHER INFORMATION: Synthetic: F primer for CyPPO4_P318A+V320L

<400> SEQUENCE: 102
attccttatg ctccattggc ttgtgttgtg ctc                         33

<210> SEQ ID NO 103
<211> LENGTH: 34
<212> TYPE: DNA
<213> ORGANISM: Artificial Sequence
<220> FEATURE:
<223> OTHER INFORMATION: Synthetic: R primer for CyPPO4_P318A+V320L

<400> SEQUENCE: 103
aacacaagcc aatggagcat aaggaatttc tgta                        34

<210> SEQ ID NO 104
<211> LENGTH: 30
<212> TYPE: DNA
<213> ORGANISM: Artificial Sequence
<220> FEATURE:
<223> OTHER INFORMATION: Synthetic: F primer for CyPPO8_F363M

<400> SEQUENCE: 104
ttgacaaata tgattggtgg agctaccgat                             30

<210> SEQ ID NO 105
<211> LENGTH: 30
<212> TYPE: DNA
<213> ORGANISM: Artificial Sequence
<220> FEATURE:
<223> OTHER INFORMATION: Synthetic: R primer for CyPPO8_F363M

<400> SEQUENCE: 105
caccaatcat atttgtcaaa aggtgccatc                             30

<210> SEQ ID NO 106
<211> LENGTH: 30
<212> TYPE: DNA
<213> ORGANISM: Artificial Sequence
<220> FEATURE:
<223> OTHER INFORMATION: Synthetic: F primer for CyPPO8_F363V

<400> SEQUENCE: 106
cttttgacaa atgttattgg tggagctacc                             30

<210> SEQ ID NO 107
<211> LENGTH: 30
<212> TYPE: DNA
<213> ORGANISM: Artificial Sequence
<220> FEATURE:
<223> OTHER INFORMATION: Synthetic: R primer for CyPPO8_F363V

<400> SEQUENCE: 107
agctccacca ataacatttg tcaaaaggtg                             30

<210> SEQ ID NO 108
<211> LENGTH: 30
<212> TYPE: DNA
<213> ORGANISM: Artificial Sequence
<220> FEATURE:
<223> OTHER INFORMATION: Synthetic: F primer for CyPPO8_F363L

<400> SEQUENCE: 108
cttttgacaa atcttattgg tggagctacc                             30

```
<210> SEQ ID NO 109
<211> LENGTH: 30
<212> TYPE: DNA
<213> ORGANISM: Artificial Sequence
<220> FEATURE:
<223> OTHER INFORMATION: Synthetic: R primer for CyPPO8_F363L

<400> SEQUENCE: 109
agctccacca ataagatttg tcaaaaggtg                                30

<210> SEQ ID NO 110
<211> LENGTH: 30
<212> TYPE: DNA
<213> ORGANISM: Artificial Sequence
<220> FEATURE:
<223> OTHER INFORMATION: Synthetic: F primer for CyPPO8_F363C

<400> SEQUENCE: 110
cttttgacaa attgtattgg tggagctacc                                30

<210> SEQ ID NO 111
<211> LENGTH: 30
<212> TYPE: DNA
<213> ORGANISM: Artificial Sequence
<220> FEATURE:
<223> OTHER INFORMATION: Synthetic: R primer for CyPPO8_F363C

<400> SEQUENCE: 111
agctccacca atacaatttg tcaaaaggtg                                30

<210> SEQ ID NO 112
<211> LENGTH: 30
<212> TYPE: DNA
<213> ORGANISM: Artificial Sequence
<220> FEATURE:
<223> OTHER INFORMATION: Synthetic: F primer for CyPPO8_A162C

<400> SEQUENCE: 112
tctggtgtgt attgtggaga tgttgatcaa                                30

<210> SEQ ID NO 113
<211> LENGTH: 30
<212> TYPE: DNA
<213> ORGANISM: Artificial Sequence
<220> FEATURE:
<223> OTHER INFORMATION: Synthetic: R primer for CyPPO8_A162C

<400> SEQUENCE: 113
atcaacatct ccacaataca caccagaaac                                30

<210> SEQ ID NO 114
<211> LENGTH: 30
<212> TYPE: DNA
<213> ORGANISM: Artificial Sequence
<220> FEATURE:
<223> OTHER INFORMATION: Synthetic: F primer for CyPPO8_A162L

<400> SEQUENCE: 114
tctggtgtgt atcttggaga tgttgatcaa                                30

<210> SEQ ID NO 115
<211> LENGTH: 30
<212> TYPE: DNA
<213> ORGANISM: Artificial Sequence
<220> FEATURE:
<223> OTHER INFORMATION: Synthetic: R primer for CyPPO8_A162L
```

<400> SEQUENCE: 115
atcaacatct ccaagataca caccagaaac                                    30

<210> SEQ ID NO 116
<211> LENGTH: 30
<212> TYPE: DNA
<213> ORGANISM: Artificial Sequence
<220> FEATURE:
<223> OTHER INFORMATION: Synthetic: F primer for CyPPO8_P306L+V308L

<400> SEQUENCE: 116
atctcatatc ttccacttgc ttgcgttgtg                                    30

<210> SEQ ID NO 117
<211> LENGTH: 30
<212> TYPE: DNA
<213> ORGANISM: Artificial Sequence
<220> FEATURE:
<223> OTHER INFORMATION: Synthetic: R primer for CyPPO8_P306L+V308L

<400> SEQUENCE: 117
aacgcaagca agtggaagat atgagatttc                                    30

<210> SEQ ID NO 118
<211> LENGTH: 30
<212> TYPE: DNA
<213> ORGANISM: Artificial Sequence
<220> FEATURE:
<223> OTHER INFORMATION: Synthetic: F primer for CyPPO8_V308M

<400> SEQUENCE: 118
tcatatcctc caatggcttg cgttgtgctc                                    30

<210> SEQ ID NO 119
<211> LENGTH: 30
<212> TYPE: DNA
<213> ORGANISM: Artificial Sequence
<220> FEATURE:
<223> OTHER INFORMATION: Synthetic: R primer for CyPPO8_V308M

<400> SEQUENCE: 119
cacaacgcaa gccattggag gatatgagat                                    30

<210> SEQ ID NO 120
<211> LENGTH: 36
<212> TYPE: DNA
<213> ORGANISM: Artificial Sequence
<220> FEATURE:
<223> OTHER INFORMATION: Synthetic: F primer for CyPPO8_P306A+V308L

<400> SEQUENCE: 120
atttcctatg ccccccctagc ttgtgtggtc ttagcc                            36

<210> SEQ ID NO 121
<211> LENGTH: 38
<212> TYPE: DNA
<213> ORGANISM: Artificial Sequence
<220> FEATURE:
<223> OTHER INFORMATION: Synthetic: R primer for CyPPO8_P306A+V308L

<400> SEQUENCE: 121
cacacaagct agggggcat aggaaatttc gtttaagg                            38

<210> SEQ ID NO 122
<211> LENGTH: 31

```
<212> TYPE: DNA
<213> ORGANISM: Artificial Sequence
<220> FEATURE:
<223> OTHER INFORMATION: Synthetic: F primer for CyPPO8_V160S

<400> SEQUENCE: 122
gtgtctgggt cttatgcagg ggatgtggat c                             31

<210> SEQ ID NO 123
<211> LENGTH: 32
<212> TYPE: DNA
<213> ORGANISM: Artificial Sequence
<220> FEATURE:
<223> OTHER INFORMATION: Synthetic: R primer for CyPPO8_V160S

<400> SEQUENCE: 123
cctgcataag acccagacac aaacggactc ac                            32

<210> SEQ ID NO 124
<211> LENGTH: 31
<212> TYPE: DNA
<213> ORGANISM: Artificial Sequence
<220> FEATURE:
<223> OTHER INFORMATION: Synthetic: F primer for CyPPO8_I343T

<400> SEQUENCE: 124
ttggtacaac ttggagttca acactctttc c                             31

<210> SEQ ID NO 125
<211> LENGTH: 31
<212> TYPE: DNA
<213> ORGANISM: Artificial Sequence
<220> FEATURE:
<223> OTHER INFORMATION: Synthetic: R primer for CyPPO8_I343T

<400> SEQUENCE: 125
gaactccaag ttgtaccaag agtgcggatt c                             31

<210> SEQ ID NO 126
<211> LENGTH: 30
<212> TYPE: DNA
<213> ORGANISM: Artificial Sequence
<220> FEATURE:
<223> OTHER INFORMATION: Synthetic: F primer for CyPPO8_F363I

<400> SEQUENCE: 126
cttttgacaa atattattgg tggagctacc                               30

<210> SEQ ID NO 127
<211> LENGTH: 30
<212> TYPE: DNA
<213> ORGANISM: Artificial Sequence
<220> FEATURE:
<223> OTHER INFORMATION: Synthetic: R primer for CyPPO8_F363I

<400> SEQUENCE: 127
agctccacca ataatatttg tcaaaaggtg                               30

<210> SEQ ID NO 128
<211> LENGTH: 30
<212> TYPE: DNA
<213> ORGANISM: Artificial Sequence
<220> FEATURE:
<223> OTHER INFORMATION: Synthetic: F primer for CyPPO8_F363T

<400> SEQUENCE: 128
``` ctttttgacaa atactattgg tggagctacc                                30

<210> SEQ ID NO 129
<211> LENGTH: 30
<212> TYPE: DNA
<213> ORGANISM: Artificial Sequence
<220> FEATURE:
<223> OTHER INFORMATION: Synthetic: R primer for CyPPO8_F363T

<400> SEQUENCE: 129
agctccacca atagtatttg tcaaaaggtg                                30

<210> SEQ ID NO 130
<211> LENGTH: 30
<212> TYPE: DNA
<213> ORGANISM: Artificial Sequence
<220> FEATURE:
<223> OTHER INFORMATION: Synthetic: F primer for CyPPO8_R85A

<400> SEQUENCE: 130
ggacttcccg cttatgttta ttgggagggg                                30

<210> SEQ ID NO 131
<211> LENGTH: 32
<212> TYPE: DNA
<213> ORGANISM: Artificial Sequence
<220> FEATURE:
<223> OTHER INFORMATION: Synthetic: R primer for CyPPO8_R85A

<400> SEQUENCE: 131
caataaacat aagcgggaag tccgcgatca gc                             32

<210> SEQ ID NO 132
<211> LENGTH: 31
<212> TYPE: DNA
<213> ORGANISM: Artificial Sequence
<220> FEATURE:
<223> OTHER INFORMATION: Synthetic: F primer for CyPPO8_I343V

<400> SEQUENCE: 132
cttggtacag tttggagttc aacactcttt c                              31

<210> SEQ ID NO 133
<211> LENGTH: 30
<212> TYPE: DNA
<213> ORGANISM: Artificial Sequence
<220> FEATURE:
<223> OTHER INFORMATION: Synthetic: R primer for CyPPO8_I343V

<400> SEQUENCE: 133
aactccaaac tgtaccaaga gtgcggattc                                30

<210> SEQ ID NO 134
<211> LENGTH: 30
<212> TYPE: DNA
<213> ORGANISM: Artificial Sequence
<220> FEATURE:
<223> OTHER INFORMATION: Synthetic: F primer for CyPPO8_P84L

<400> SEQUENCE: 134
aggtttactt aggtatgttt actgggaggg                                30

<210> SEQ ID NO 135
<211> LENGTH: 30
<212> TYPE: DNA
<213> ORGANISM: Artificial Sequence

```
<220> FEATURE:
<223> OTHER INFORMATION: Synthetic: R primer for CyPPO8_P84L

<400> SEQUENCE: 135
catacctaag taaacctcta tctgcaaaga                                         30

<210> SEQ ID NO 136
<211> LENGTH: 33
<212> TYPE: DNA
<213> ORGANISM: Artificial Sequence
<220> FEATURE:
<223> OTHER INFORMATION: Synthetic: F primer for CyPPO8_R85C

<400> SEQUENCE: 136
gacttccctg ttatgtttat tgggagggga aac                                     33

<210> SEQ ID NO 137
<211> LENGTH: 33
<212> TYPE: DNA
<213> ORGANISM: Artificial Sequence
<220> FEATURE:
<223> OTHER INFORMATION: Synthetic: R primer for CyPPO8_R85C

<400> SEQUENCE: 137
taaacataac agggaagtcc gcgatcagca aag                                     33

<210> SEQ ID NO 138
<211> LENGTH: 32
<212> TYPE: DNA
<213> ORGANISM: Artificial Sequence
<220> FEATURE:
<223> OTHER INFORMATION: Synthetic: F primer for CyPPO8_R85H

<400> SEQUENCE: 138
acttccccat tatgtttatt gggaggggaa ac                                      32

<210> SEQ ID NO 139
<211> LENGTH: 32
<212> TYPE: DNA
<213> ORGANISM: Artificial Sequence
<220> FEATURE:
<223> OTHER INFORMATION: Synthetic: R primer for CyPPO8_R85H

<400> SEQUENCE: 139
caataaacat aatggggaag tccgcgatca gc                                      32

<210> SEQ ID NO 140
<211> LENGTH: 32
<212> TYPE: DNA
<213> ORGANISM: Artificial Sequence
<220> FEATURE:
<223> OTHER INFORMATION: Synthetic: F primer for CyPPO8_R85L

<400> SEQUENCE: 140
acttcccctt tatgtttatt gggaggggaa ac                                      32

<210> SEQ ID NO 141
<211> LENGTH: 32
<212> TYPE: DNA
<213> ORGANISM: Artificial Sequence
<220> FEATURE:
<223> OTHER INFORMATION: Synthetic: R primer for CyPPO8_R85L

<400> SEQUENCE: 141
caataaacat aaaggggaag tccgcgatca gc                                      32
```

<210> SEQ ID NO 142
<211> LENGTH: 33
<212> TYPE: DNA
<213> ORGANISM: Artificial Sequence
<220> FEATURE:
<223> OTHER INFORMATION: Synthetic: F primer for CyPPO8_R85T

<400> SEQUENCE: 142
gacttcccac ttatgtttat tgggagggga aac                                33

<210> SEQ ID NO 143
<211> LENGTH: 34
<212> TYPE: DNA
<213> ORGANISM: Artificial Sequence
<220> FEATURE:
<223> OTHER INFORMATION: Synthetic: R primer for CyPPO8_R85T

<400> SEQUENCE: 143
ataaacataa gtgggaagtc cgcgatcagc aaag                               34

<210> SEQ ID NO 144
<211> LENGTH: 33
<212> TYPE: DNA
<213> ORGANISM: Artificial Sequence
<220> FEATURE:
<223> OTHER INFORMATION: Synthetic: F primer for CyPPO8_R85V

<400> SEQUENCE: 144
gacttcccgt ttatgtttat tgggagggga aac                                33

<210> SEQ ID NO 145
<211> LENGTH: 34
<212> TYPE: DNA
<213> ORGANISM: Artificial Sequence
<220> FEATURE:
<223> OTHER INFORMATION: Synthetic: R primer for CyPPO8_R85V

<400> SEQUENCE: 145
ataaacataa acgggaagtc cgcgatcagc aaag                               34

<210> SEQ ID NO 146
<211> LENGTH: 30
<212> TYPE: DNA
<213> ORGANISM: Artificial Sequence
<220> FEATURE:
<223> OTHER INFORMATION: Synthetic: F primer for CyPPO8_F156A

<400> SEQUENCE: 146
gtgagtccgg ctgtgtctgg ggtttatgca                                    30

<210> SEQ ID NO 147
<211> LENGTH: 30
<212> TYPE: DNA
<213> ORGANISM: Artificial Sequence
<220> FEATURE:
<223> OTHER INFORMATION: Synthetic: R primer for CyPPO8_F156A

<400> SEQUENCE: 147
cccagacaca gccggactca ctaaccgttg                                    30

<210> SEQ ID NO 148
<211> LENGTH: 33
<212> TYPE: DNA
<213> ORGANISM: Artificial Sequence
<220> FEATURE:
<223> OTHER INFORMATION: Synthetic: F primer for CyPPO8_V160C

<400> SEQUENCE: 148
ccgtttgtgt ctgggtgcta tgcaggggat gtg                33

<210> SEQ ID NO 149
<211> LENGTH: 33
<212> TYPE: DNA
<213> ORGANISM: Artificial Sequence
<220> FEATURE:
<223> OTHER INFORMATION: Synthetic: R primer for CyPPO8_V160C

<400> SEQUENCE: 149
cacatcccct gcatagcacc cagacacaaa cgg                33

<210> SEQ ID NO 150
<211> LENGTH: 31
<212> TYPE: DNA
<213> ORGANISM: Artificial Sequence
<220> FEATURE:
<223> OTHER INFORMATION: Synthetic: F primer for CyPPO8_Q179G

<400> SEQUENCE: 150
tccgccagtc cggtaactcg tccaaatgca g                  31

<210> SEQ ID NO 151
<211> LENGTH: 31
<212> TYPE: DNA
<213> ORGANISM: Artificial Sequence
<220> FEATURE:
<223> OTHER INFORMATION: Synthetic: R primer for CyPPO8_Q179G

<400> SEQUENCE: 151
cgagttaccg gactggcgga tgtgggcggt g                  31

<210> SEQ ID NO 152
<211> LENGTH: 36
<212> TYPE: DNA
<213> ORGANISM: Artificial Sequence
<220> FEATURE:
<223> OTHER INFORMATION: Synthetic: F primer for CyPPO8_F327V

<400> SEQUENCE: 152
gttttcccct caaaggagtg ggtaatctta accctc             36

<210> SEQ ID NO 153
<211> LENGTH: 36
<212> TYPE: DNA
<213> ORGANISM: Artificial Sequence
<220> FEATURE:
<223> OTHER INFORMATION: Synthetic: R primer for CyPPO8_F327V

<400> SEQUENCE: 153
gagggttaag attacccact cctttgaggg gaaaac             36

<210> SEQ ID NO 154
<211> LENGTH: 30
<212> TYPE: DNA
<213> ORGANISM: Artificial Sequence
<220> FEATURE:
<223> OTHER INFORMATION: Synthetic: F primer for CyPPO8_L330T

<400> SEQUENCE: 154
tttggtaata ctaaccctcg cagtcaagga                    30

<210> SEQ ID NO 155

```
<210> SEQ ID NO 155
<211> LENGTH: 30
<212> TYPE: DNA
<213> ORGANISM: Artificial Sequence
<220> FEATURE:
<223> OTHER INFORMATION: Synthetic: R primer for CyPPO8_L330T

<400> SEQUENCE: 155
gcgagggtta gtattaccaa atcctttgag                                    30

<210> SEQ ID NO 156
<211> LENGTH: 30
<212> TYPE: DNA
<213> ORGANISM: Artificial Sequence
<220> FEATURE:
<223> OTHER INFORMATION: Synthetic: F primer for CyPPO8_F363M+N362S

<400> SEQUENCE: 156
cttttgacat caatgattgg tggagctacc                                    30

<210> SEQ ID NO 157
<211> LENGTH: 30
<212> TYPE: DNA
<213> ORGANISM: Artificial Sequence
<220> FEATURE:
<223> OTHER INFORMATION: Synthetic: R primer for CyPPO8_F363M+N362S

<400> SEQUENCE: 157
ccaatcattg atgtcaaaag gtgccatcct                                    30

<210> SEQ ID NO 158
<211> LENGTH: 21
<212> TYPE: DNA
<213> ORGANISM: Artificial Sequence
<220> FEATURE:
<223> OTHER INFORMATION: Synthetic: Forward primer for CyPPO8 F363M
     probe

<400> SEQUENCE: 158
gcgttaacgg gtgcattagg c                                             21

<210> SEQ ID NO 159
<211> LENGTH: 20
<212> TYPE: DNA
<213> ORGANISM: Artificial Sequence
<220> FEATURE:
<223> OTHER INFORMATION: Synthetic: Reverse primer for CyPPO8 F363M
     probe

<400> SEQUENCE: 159
tggaaagagt gttgaactcc                                               20

<210> SEQ ID NO 160
<211> LENGTH: 20
<212> TYPE: DNA
<213> ORGANISM: Artificial Sequence
<220> FEATURE:
<223> OTHER INFORMATION: Synthetic: TOPO-cTP_F primer

<400> SEQUENCE: 160
caccatggag ttatctcttc                                               20

<210> SEQ ID NO 161
<211> LENGTH: 20
<212> TYPE: DNA
<213> ORGANISM: Artificial Sequence
<220> FEATURE:
<223> OTHER INFORMATION: Synthetic: TOPO-CyPPO2_R primer
```

```
<400> SEQUENCE: 161
tcagatcgat cgagtatctg                                               20

<210> SEQ ID NO 162
<211> LENGTH: 20
<212> TYPE: DNA
<213> ORGANISM: Artificial Sequence
<220> FEATURE:
<223> OTHER INFORMATION: Synthetic: TOPO-CyPPO8_R primer

<400> SEQUENCE: 162
ttaacccaaa taatctaaca                                               20

<210> SEQ ID NO 163
<211> LENGTH: 20
<212> TYPE: DNA
<213> ORGANISM: Artificial Sequence
<220> FEATURE:
<223> OTHER INFORMATION: Synthetic: Forward primer for bar probe

<400> SEQUENCE: 163
ttccgtaccg agccgcagga                                               20

<210> SEQ ID NO 164
<211> LENGTH: 20
<212> TYPE: DNA
<213> ORGANISM: Artificial Sequence
<220> FEATURE:
<223> OTHER INFORMATION: Synthetic: Reverse primer for bar probe

<400> SEQUENCE: 164
cgttgggcag cccgatgaca                                               20
```

PROTOPORPHYRINOGEN OXIDASE VARIANTS AND METHODS AND COMPOSITIONS FOR CONFERRING AND/OR ENHANCING HERBICIDE TOLERANCE USING THE SAME

TECHNICAL FIELD

Provided are protoporphyrinogen oxidases derived from prokaryotes, or its variants, and technology for conferring and/or enhancing herbicide tolerance of plants and/or algae using the same.

BACKGROUND ART

A porphyrin biosynthetic pathway serves for the synthesis of chlorophyll and heme which play vital roles in plant metabolism, and it takes place in the chloroplast. In this pathway, protoporphyrinogen IX oxidase (hereinafter, referred to as PPO; EC:1.3.3.4) catalyzes the oxidation of protoporphyrinogen IX to protoporphyrin IX. After the oxidation of protoporphyrinogen IX to protoporphyrin IX, protoporphyrin IX binds with magnesium by Mg-chelatase to synthesize chlorophyll, or it binds with iron by Fe-chelatase to synthesize heme.

Therefore, when PPO activity is inhibited, synthesis of chlorophylls and heme is inhibited and the substrate protoporphyrinogen IX leaves the normal porphyrin biosynthetic pathway, resulting in the rapid export of protoporphyrinogen IX from the chloroplast to the cytoplasm, and cytoplasmic protoporphyrin IX accumulation caused by the oxidation. Accumulated protoporphyrin IX generates highly reactive singlet oxygen ($^1O_2$) in the presence of light and oxygen molecules which destroy cell membrane and rapidly leads to plant cell death. Based on this principle, herbicides inhibiting PPO activity have been developed. Until now, there have been 9 families of PPO-inhibiting herbicides, including pyrimidinediones, diphenyl-ethers, phenylpyrazoles, N-phenylphthalimides, thiadiazoles, oxadiazoles, triazolinones, oxazolidinediones, and others herbicides, which are classified according to their chemical structures.

Further, in order to prevent effects of these herbicides on the growth of crops while using the herbicides, there is a need to provide herbicide tolerance for the crops.

Meanwhile, algae are photosynthetic organisms that can convert light energy into chemical energy which can be used to synthesize various useful compounds. For example, algae can fix carbon by photosynthesis and convert carbon dioxide into sugar, starch, lipids, fats, or other biomolecules, thereby removing greenhouse gases from the atmosphere. In addition, large-scale cultivation of algae can produce a variety of substances such as industrial enzymes, therapeutic compounds and proteins, nutrients, commercial materials and fuel materials.

However, in case of large-scale cultivation of algae in a bioreactor or in an open or enclosed pond, contamination may occur by undesired competent organisms, for example, undesired algae, fungi, rotifer, or zooplankton.

Thus, a technology is needed to harvest desired plants and/or algae on a large scale by treating herbicides at a concentration that would inhibit the growth of competent organisms without herbicide tolerance, after conferring herbicide tolerance to desired plants and/or algae.

REFERENCES (Patent document 1) U.S. patent application registration publication U.S. Pat. No. 6,308,458 (2001 Oct. 30)

(Patent document 2) U.S. patent application registration publication U.S. Pat. No. 6,808,904 (2004 Oct. 26)

(Patent document 3) U.S. patent application registration publication U.S. Pat. No. 7,563,950 (2009 Jul. 21)

(Patent document 4) International patent application laid-open publication WO2011/085221 (2011 Jul. 14)

(Non-patent document 1) Li X, Volrath S L., Chilcott C E, Johnson M A, Ward E R, Law M D, Development of protoporphyrinogen oxidase as an efficient selection marker for Agrobacterium tumefaciens-mediated transformation of maize. Plant physiology 133:736-747, 2003

DISCLOSURE

Technical Problem

In this specification, it is found that hemY-type PPO genes derived from prokaryotes and mutants thereof show a broad herbicide tolerance to protoporphyrinogen oxidase (PPO)-inhibiting herbicides, and thereby it is proposed if providing plants and/or algae with the same, herbicide tolerance can be conferred and/or enhanced.

One embodiment provides a polypeptide variant comprising, consisting essentially of, or consisting of:

(1) an amino acid sequence wherein one or more selected from the group consisting of amino acids affecting to the interaction between PPO-inhibiting herbicides and the polypeptide of PPO, SEQ ID NO: 1 (e.g., amino acids positioned on binding sites of the polypeptide of SEQ ID NO: 1 interacting with PPO-inhibiting herbicide) are respectively independently deleted or substituted with an amino acid which is different from original amino acid in the corresponding position, or (2) an amino acid sequence having 95% or higher, 98% or higher, or 99% or higher sequence homology with the amino acid sequence (1).

The one or more selected from the group consisting of amino acids affecting to the interaction between PPO-inhibiting herbicides and the polypeptide of PPO, SEQ ID NO: 1, may be one or more selected from the group consisting of S63, P91, R92, F169, V173, A175, E228, L229, P316, V318, F337, L340, G351, T352, I353, and Y373, of the amino acid sequence of SEQ ID NO: 1.

Another embodiment provides a polypeptide variant comprising, consisting essentially of, or consisting of:

(1) an amino acid sequence wherein one or more selected from the group consisting of amino acids affecting to the interaction between PPO-inhibiting herbicides and the polypeptide of PPO, SEQ ID NO: 3 (e.g., amino acids positioned on binding sites of the polypeptide of SEQ ID NO: 3 interacting with PPO-inhibiting herbicide) are respectively independently deleted or substituted with an amino acid which is different from original amino acid in the corresponding position, or (2) an amino acid sequence having 95% or higher, 98% or higher, or 99% or higher sequence homology with the amino acid sequence (1).

The one or more kinds selected from the group consisting of amino acids affecting to the interaction between PPO-inhibiting herbicides and the polypeptide of PPO, SEQ ID NO: 3, may be one or more selected from the group consisting of N63, S64, S66, P67, P92, R93, F170, S172, G173, V174, Y175, A176, R190, E230, L231, P318, V320, F339, G340, N341, L342, L352, G353, T354, I355, Y375, I424, V458, and R465, of the amino acid sequence of SEQ ID NO: 3.

Other embodiment provides a polypeptide variant comprising, consisting essentially of, or consisting of:

(1) an amino acid sequence wherein one or more kinds selected from the group consisting of amino acids affecting to the interaction between PPO-inhibiting herbicides and the polypeptide of PPO, SEQ ID NO: 5 (e.g., amino acids positioned on binding sites of the polypeptide of SEQ ID NO: 5 interacting with PPO-inhibiting herbicide), are respectively independently deleted or substituted with an amino acid which is different from original amino acid in the corresponding position, or (2) an amino acid sequence having 95% or higher, 98% or higher, or 99% or higher sequence homology with the amino acid sequence (1).

The one or more kinds selected from the group consisting of amino acids affecting to the interaction between PPO-inhibiting herbicides and the polypeptide of PPO, SEQ ID NO: 5, may be one or more selected from the group consisting of P84, R85, F156, V160, A162, Q179, P306, V308, F327, L330, I343, N362, and F363, of the amino acid sequence of SEQ ID NO: 5.

Other embodiment provides a polynucleotide encoding the polypeptide variant, or a polypeptide of SEQ ID NO: 1, 3, or 5.

Other embodiment provides a recombinant vector comprising the polynucleotide.

Other embodiment provides a recombinant (transformed) cell comprising the recombinant vector.

Other embodiment provides a composition for conferring or enhancing herbicide tolerance of plants or algae, comprising one or more selected from the group consisting of:

the polypeptide of SEQ ID NO: 1, the polypeptide of SEQ ID NO: 3, the polypeptide of SEQ ID NO: 5, a variant of the polypeptide, and a polypeptide with an amino acid sequence having 95% or higher, 98% or higher, or 99% or higher sequence homology with the polypeptide or the variant;

a polynucleotide encoding the polypeptide or variant;

a recombinant vector comprising the polynucleotide; and a recombinant (transformed) cell comprising the recombinant vector.

The herbicide may be an herbicide inhibiting protoporphyrinogen oxidase.

As a specific embodiment, the herbicide may be one or more kinds selected from the group consisting of pyrimidinediones, diphenyl-ethers, phenylpyrazoles, N-phenylphthalimides, phenylesters, thiadiazoles, oxadiazoles, triazolinones, oxazolidinediones and other herbicides, but not limited thereto.

As a specific embodiment, the herbicide may be one or more kinds selected from the group consisting of butafenacil, saflufenacil, benzfendizone, tiafenacil, fomesafen, oxyfluorfen, aclonifen, acifluorfen, bifenox, ethoxyfen, lactofen, chlomethoxyfen, chlorintrofen, fluoroglycofen-ethyl, halosafen, pyraflufen-ethyl, fluazolate, flumioxazin, cinidon-ethyl, flumiclorac-pentyl, fluthiacet, thidiazimin, oxadiargyl, oxadiazon, carfentrazone, sulfentrazone, azafenidin, pentoxazone, pyraclonil, flufenpyr-ethyl, profluazol, phenopylate (2,4-dichlorophenyl 1-pyrrolidinecarboxylate), carbamate analogues of phenopylate (for example, O-phenylpyrrolidino- and piperidinocarbamate analoges (refer to "Ujjana B. Nandihalli, Mary V. Duke, Stephen O. Duke, Relationships between molecular properties and biological activities of O-phenyl pyrrolidino- and piperidinocarbamate herbicides, J. Agric. Food Chem., 1992, 40(10) 1993-2000")), agriculturally acceptable salts thereof, and combinations thereof, but not limited thereto.

The plant means a multicellular eukaryote having photosynthetic capability, which may be a monocotyledonous plant or a dicotyledonous plant, and may be an herbaceous plant or a woody plant. The algae mean unicellular organism having photosynthetic capability, which may be a prokaryotic algae or a eukaryotic algae.

In one embodiment, the plants and algae are genetically manipulated in order to further comprise a second herbicide tolerance polypeptide or a gene encoding thereof, and broader range of herbicide tolerance to the second herbicide may be conferred and/or enhanced. The plants and algae are genetically manipulated in order to comprise the second herbicide tolerance polypeptide or a gene encoding thereof may be prepared using a composition for conferring and/or enhancing tolerance to the herbicide wherein the second herbicide tolerance polypeptide or a gene encoding thereof is further comprised. Thus, a composition for conferring and/or enhancing tolerance to the herbicide may further comprise the second herbicide tolerance polypeptide or a gene encoding thereof.

As a specific embodiment, the second herbicide may include cell division-inhibiting herbicides, photosynthesis-inhibiting herbicides, amino acid synthesis-inhibiting herbicides, plastid-inhibiting herbicides, and cell membrane-inhibiting herbicides, but not limited thereto.

As a specific embodiment, the second herbicide may be exemplified by glyphosate, glufosinate, dicamba, 2,4-D (2,4-Dichlorophenoxyacetic acid), isoxaflutole, ALS (acetolactate synthase)-inhibiting herbicide, photosystem II-inhibiting herbicide, phenylurea-based herbicide, bromoxynil-based herbicide, and combinations thereof, but not limited thereto.

As a specific embodiment, the second herbicide may be exemplified by one or more kinds selected from the group consisting of glyphosate herbicide-tolerant EPSPS (glyphosate resistant 5-enolpyruvylshikimate-3-phosphate synthase), GOX (glyphosate oxidase), GAT (glyphosate-N-acetyltransferase) or glyphosate decarboxylase); glufosinate herbicide-tolerant PAT (phosphinothricin-N-acetyltransferase); dicamba herbicide-tolerant DMO (dicamba monooxygenase); 2,4-D herbicide-tolerant 2,4-D monooxygenase or AAD (aryloxyalkanoate dioxygenase); ALS-inhibiting sulfonylurea-based herbicide-tolerant ALS (acetolactate Synthase), AHAS (acetohydroxyacid synthase), or athahasl (acetohydroxyacid synthase large subunit); photosystem II-inhibiting herbicide-tolerant photosystem II protein D1; phenylurea-based herbicide-tolerant cytochrome P450; plastid-inhibiting herbicide-tolerant HPPD (hydroxylphenylpyruvate dioxygenase); bromoxynil herbicide-tolerant nitrilase; and combinations thereof, but not limited thereto.

Further, the gene encoding the second herbicide-tolerant polypeptide may be exemplified by one or more kinds selected from the group consisting of glyphosate herbicide-tolerant cp4 epsps, mepsps, 2mepsps, goxv247, gat4601 or gat4621 gene; glufosinate herbicide-tolerant bar, pat or pat (SYN) gene; dicamba herbicide-tolerant dmo gene; 2,4-D herbicide-tolerant AAD-1, AAD-12 gene; ALS-inhibiting sulfonylurea-based herbicide-tolerant ALS, GM-HRA, S4-HRA, ZM-HRA, Csr1, Csr1-1, Csr1-2, SurA or SurB; photosystem II-inhibiting herbicide-tolerant psbA gene; phenylurea herbicide-tolerant CYP76B1 gene; isoxaflutole herbicide-tolerant HPPDPF W336 gene and bromoxynil herbicide-tolerant bxn gene; and combinations thereof, but not limited thereto.

Other embodiment provides a transformant of a plant and/or algae having herbicide tolerance, which are transformed with the polynucleotide, or a clone or progeny thereof.

Other embodiment provides a method of preparing a transgenic plant or a transgenic algae having herbicide tolerance, comprising a step of transforming a plant and/or algae with the polynucleotide.

Other embodiment provides a method of conferring or enhancing herbicide tolerance of a plant and/or algae, comprising a step of transforming a plant and/or algae with the polynucleotide or a coding gene thereof.

The transformation may be performed on algae, and/or plant cell, protoplast, callus, hypocotyl, seed, cotyledon, shoot, or whole plant.

The transformant may be algae, and/or plant cell, protoplast, callus, hypocotyl, seed, cotyledon, shoot, or whole plant.

Other embodiment provides a method of controlling weeds in a cropland comprising:

a step of providing the cropland with a plant comprising one or more selected from the group consisting of the polypeptide of SEQ ID NO: 1, 3, or 5, or the polypeptide variant, a polynucleotide encoding thereof, a recombinant vector comprising the polynucleotide, and a recombinant cell comprising the recombinant vector; and a step of applying an effective dosage of a protoporphyrinogen oxidase-inhibiting herbicide to the cropland (or to the plant).

As a specific embodiment, the step of applying an effective dosage of protoporphyrinogen oxidase-inhibiting herbicide to the cropland may be performed by applying an effective dosage of two or more protoporphyrinogen oxidase-inhibiting herbicides sequentially or simultaneously.

As other embodiment, the plant may be genetically manipulated in order to further comprise a second herbicide-tolerant polypeptide or a gene encoding the same, and an effective dosage of the protoporphyrinogen oxidase-inhibiting herbicide and the second herbicide may be applied sequentially or simultaneously.

Other embodiment provides a method of removing an undesired aquatic organism from a culture medium, comprising a step of providing a culture medium with algae comprising one or more selected from the group consisting of the polypeptide, the polypeptide variant, a polynucleotide encoding the polypeptide or the polypeptide variant, a recombinant vector comprising the polynucleotide, and a recombinant cell comprising the recombinant vector, and a step of applying an effective dosage of a protoporphyrinogen oxidase-inhibiting herbicide to the culture medium.

Technical Solution

Provided is a technology of conferring and/or enhancing herbicide tolerance of plants or algae.

As used herein, 'conferring and/or enhancing herbicide tolerance of plants or algae' or 'enhancing herbicide tolerance of plants or algae' is interpreted as conferring tolerance on plants or algae which do not have herbicide tolerance, or enhancing tolerance of plants or algae which have herbicide tolerance, or broad meaning of covering both.

As used herein, 'consisting of a sequence,' 'consisting essentially of a sequence,' or 'comprising a sequence' is used in order to mean both cases of comprising described sequence, or necessarily comprising the sequence, and may be interpreted as meaning of comprising a sequence other than described sequence and/or comprising mutation (addition, deletion, and/or substitution of an amino acid or nucleic acid), as long as maintaining an intrinsic activity of protein, polypeptide, or nucleic acid molecule and exhibiting intended function.

In one embodiment, provided are one or more polypeptide variants selected from the group consisting of a polypeptide variant comprising, consisting essentially of, or consisting of an amino acid sequence wherein one or more kinds selected from the group consisting of amino acids affecting to the interaction between PPO-inhibiting herbicides and polypeptide of PPO, SEQ ID NO: 1 (e.g., amino acids positioned on binding sites of SEQ ID NO: 1 interacting with PPO-inhibiting herbicide), are respectively independently deleted or substituted with other amino acid which is different from original amino acid in the corresponding position, or an amino acid sequence having 95% or higher, 98% or higher, or 99% or higher homology thereto;

a polypeptide variant comprising, consisting essentially of, or consisting of an amino acid sequence wherein one or more kinds selected from the group consisting of amino acids affecting to the interaction between PPO-inhibiting herbicides and the polypeptide of PPO, SEQ ID NO: 3 (e.g., amino acids positioned on binding sites of SEQ ID NO: 3 interacting with PPO-inhibiting herbicide), are respectively independently deleted or substituted with other amino acid which is different from original amino acid in the corresponding position, or an amino acid sequence having 95% or higher, 98% or higher, or 99% or higher homology thereto;

a polypeptide variant comprising, consisting essentially of, or consisting of an amino acid sequence wherein one or more kinds selected from the group consisting of amino acids affecting to the interaction between PPO-inhibiting herbicides and the polypeptide of PPO, SEQ ID NO: 5 (e.g., amino acids positioned on binding sites of SEQ ID NO: 5 interacting with PPO-inhibiting herbicide), are respectively independently deleted or substituted with other amino acid which is different from original amino acid in the corresponding position, or an amino acid sequence having 95% or higher, 98% or higher, or 99% or higher homology thereto; and combinations thereof.

In other embodiment, provided is a polynucleotide encoding the polypeptide variant, a recombinant vector comprising the polynucleotide, and a recombinant cell comprising the recombinant vector. The polynucleotide may be designed in order that an optimized codon is comprised in a cell to be transformed among codons encoding each amino acid. The optimized codon may be easily known to a person skilled in the art (for example, refer to "www.genscript.com/codon-opt.html", "sg.idtdna.com/CodonOpt" etc.).

In other embodiment, provided a composition for conferring or enhancing herbicide tolerance of plants or algae, comprising one or more kinds selected from the group consisting of the polypeptide variant, a polynucleotide encoding the polypeptide, a recombinant vector comprising the polynucleotide, a recombinant cell comprising the recombinant vector, and combinations thereof.

In other embodiment, provided is a transformant having herbicide tolerance, which is transformed with the polynucleotide.

In other embodiment, provided is a method of preparing a transgenic plant or a transgenic algae having herbicide tolerance, comprising a step of transforming algae, or plant cell, protoplast, callus, hypocotyl, seed, cotyledon, shoot, or whole plant with the polynucleotide.

In other embodiment, provided is a method of conferring or enhancing herbicide tolerance of plants or algae, comprising a step of transforming algae, or plant cell, protoplast, callus, hypocotyl, seed, cotyledon, shoot, or whole plant with the polynucleotide.

Hereinafter, the present invention will be described in more detail.

The polypeptide of an amino acid sequence of SEQ ID NO: 1, 3, 5, or its variant provided herein is a PPO protein derived from a prokaryote (for example, cyanobacteria), and is an herbicide-tolerant PPO protein having tolerance to PPO-inhibiting herbicides. Specifically, a PPO protein which is derived from *Oscillatoria nigro-viridis* PCC 7112 is provided, and it is designated as CyPPO2, and its amino acid sequence is represented by SEQ ID NO: 1, and a nucleotide sequence of a gene encoding thereof is represented by SEQ ID NO: 2. In addition, a PPO derived from *Lyngbya* sp. PCC 8106 strain is provided, and it is designated as CyPPO4, and its amino acid sequence is represented by SEQ ID NO: 3, and a nucleotide sequence of a gene encoding thereof is represented by SEQ ID NO: 4. In addition, a PPO derived from *Halothece* sp. PCC 7418 strain is provided, and it is designated as CyPPO8, and its amino acid sequence is represented by SEQ ID NO: 5, and a nucleotide sequence of a gene encoding thereof is represented by SEQ ID NO: 6. Herein, the polypeptide and variants of polypeptide described above may be expressed respectively as herbicide-tolerant PPO protein or herbicide-tolerant PPO protein variant having tolerance to PPO-inhibiting herbicides. In addition, as used herein, "herbicide-tolerant PPO or its variant" may be used in order to mean the above herbicide-tolerant PPO protein or herbicide-tolerant PPO protein variant, herbicide-tolerant PPO protein-encoding gene or herbicide-tolerant PPO protein variant-encoding gene, or all of them.

Cyanobacteria-derived PPO proteins can have enhanced tolerance to PPO-inhibiting herbicides and/or by comprising amino acid mutation (variation) in a range of maintaining overall enzyme activity than wild type PPO proteins. Such amino acid mutation may comprise substitution, deletion, addition and/or introduction of one or more kinds of amino acids selected from amino acid residues of interaction sites between PPO proteins and herbicides.

The PPO protein variant will be described in more detail as follows.

One embodiment provides a polypeptide variant comprising, consisting essentially of, or consisting of:

an amino acid sequence wherein one or more kinds selected from the group consisting of amino acids affecting to the interaction between PPO-inhibiting herbicides and the polypeptide of PPO, SEQ ID NO: 1 (CyPPO2) (e.g., amino acids positioned in binding sites to PPO inhibiting herbicides of polypeptide of SEQ ID NO: 1), are respectively independently deleted or substituted with other amino acid, which is different from original amino acid (namely, an amino acid in the corresponding position of the wild type), or an amino acid sequence having 95% or higher, 98% or higher, or 99% or higher homology thereto.

The amino acid residue of polypeptide of SEQ ID NO: 1, which is deleted or substituted with other amino acid that is different from original amino acid (e.g., one or more residues selected from the group consisting of amino acids positioned on binding sites to PPO-inhibiting herbicides of polypeptide of SEQ ID NO: 1), may be one or more selected from the group consisting of S63 (meaning of "S(Ser) at the $63^{rd}$ position"; the expression of the following amino acid residues is interpreted in the same manner), P91, R92, F169, V173, A175, E228, L229, P316, V318, F337, L340, G351, T352, I353, and Y373 among the amino acid sequence of SEQ ID NO: 1.

In one specific embodiment, the variant of polypeptide may comprise, consist essentially of, or consist of:

an amino acid sequence wherein one or more selected from the group consisting of S63, P91, R92, F169, V173, A175, E228, L229, P316, V318, F337, L340, G351, T352, I353, and Y373 of the amino acid sequence of SEQ ID NO: 1 are respectively and independently deleted or substituted with an amino acid which is selected from the group consisting of M(Met), V(Val), I(Ile), T(Thr), L(Leu), C(Cys), A(Ala), S(Ser), F(Phe), P(Pro), W(Trp), N(Asn), Q(Gln), G(Gly), Y(Tyr), D(Asp), E(Glu), R(Arg), H(His), K(Lys), etc. and is different from the amino acid at the corresponding position in the wild type (for example, substituted with an amino acid which is selected from the group consisting of M(Met), V(Val), I(Ile), T(Thr), L(Leu), C(Cys), A(Ala), S(Ser), F(Phe), etc. and is different from the amino acid at the corresponding position in the wild type), or an amino acid sequence having 95% or higher, 98% or higher, or 99% or higher homology thereto.

For example, the variant of polypeptide may comprise, consist essentially of, or consist of:

an amino acid sequence comprising one or more amino acid mutations selected from the group consisting of Y373M (meaning of "the amino acid residue at the $373^{rd}$ position is substituted from Y(Tyr) to M(Met)"; the expression of the following amino acid mutations is interpreted in the same manner), Y373V, Y373I, Y373T, Y373L, Y373C, F169A, A175C, A175L, A175I, P316A, P316L, V318M, V318T, V318L, G351A, S63T, P91L, R92A, V173S, V173C, V173T, V173L, E228A, L229F, F337V, L340T, L340I, L340V, T352V, I353T, I353L, I353V, and I353C, in the amino acid sequence of SEQ ID NO: 1; or an amino acid sequence having 95% or higher, 98% or higher, or 99% or higher homology thereto.

For example, the variant of polypeptide may comprise, consist essentially of, or consist of:

an amino acid sequence comprising one or more amino acid mutations selected from the group consisting of amino acid mutations of Y373M, Y373V, Y373I, Y373T, Y373L, Y373C, F169A, A175C, A175L, A175I, P316A, P316L, V318M, V318T, V318L, G351A, S63T, P91L, R92A, V173S, V173C, V173T, V173L, E228A, L229F, F337V, L340T, L340I, L340V, T352V, I353T, I353L, I353V, I353C, S63T+Y373M (meaning of a mutant or mutation comprising all of substitution of the $63^{rd}$ residue from S to T and substitution of the $373^{rd}$ residue from Y to M; the expression of the following two or more amino acid mutations is interpreted in the same manner), R92A+Y373M, V173S+Y373M, V173S+Y373I, V173S+Y373L, V173S+Y373V, V173C+Y373M, V173C+Y373I, V173T+Y373M, V173T+Y373I, V173L+Y373M, A175L+Y373M, A175L+Y373I, A175C+Y373M, A175C+Y373I, A175I+Y373M, E228A+Y373M, L229F+Y373T, V318M+Y373M, V318M+Y373I, V318M+Y373V, V318T+Y373I, L340I+Y373M, L340I+Y373I, L340V+Y373M, G351A+Y373M, I353T+Y373M, I353T+Y373I, I353T+Y373L, I353L+Y373M, I353V+Y373M, I353C+Y373M, S63T+V173S+Y373M, S36T+V173S+Y373I, S63T+I353T+Y373M, S63T+I353T+Y373I, V173S+V318M+Y373M, V173T+L340I+Y373M, V173S+A175C+Y373M, A175C+V318M+Y373M, A175L+V318M+Y373M, A175C+I353L+Y373M, A175C+I353V+Y373M, P316A+V318L, P316L+V318L, F337V+

Y373M, T352V+Y373M, G351A+T352V+Y373M, and P91L+Y373M, in the amino acid sequence of SEQ ID NO: 1, or an amino acid sequence having 95% or higher, 98% or higher, or 99% or higher homology thereto.

Other embodiment provides a polypeptide variant comprising, consisting essentially of, or consisting of:

an amino acid sequence wherein one or more selected from the group consisting of amino acids affecting to the interaction between PPO-inhibiting herbicides and the polypeptide of PPO, SEQ ID NO: 3 (CyPPO4) (e.g., amino acids positioned on binding sites to PPO-inhibiting herbicides of polypeptide of SEQ ID NO: 3), are respectively and independently deleted or substituted with other amino acid which is different from original amino acid (namely, an amino acid at the corresponding position of the wild type), or an amino acid sequence having 95% or higher, 98% or higher, or 99% or higher homology thereto.

The amino acid residue of polypeptide of SEQ ID NO: 3 which is deleted or substituted with other amino acid that is different from original amino acid (e.g., one or more kinds selected from the group consisting of amino acids positioned on binding sites to PPO-inhibiting herbicides of polypeptide of SEQ ID NO: 3) may be one or more selected from the group consisting of N63, S64, S66, P67, P92, R93, F170, S172, G173, V174, Y175, A176, R190, E230, L231, P318, V320, F339, G340, N341, L342, L352, G353, T354, I355, Y375, I424, V458, and R465, for example, one or more selected from the group consisting of A176, P318, V320, and Y375, of the amino acid sequence of SEQ ID NO: 3.

In one specific embodiment, the variant of polypeptide may comprise, consist essentially of, or consist of:

an amino acid sequence wherein one or more selected from the group consisting of N63, S64, S66, P67, P92, R93, F170, S172, G173, V174, Y175, A176, R190, E230, L231, P318, V320, F339, G340, N341, L342, L352, G353, T354, I355, Y375, I424, V458, and R465, for example, one or more selected from the group consisting of A176, P318, V320, and Y375, of the amino acid sequence of SEQ ID NO: 3 are respectively and independently deleted or substituted with an amino acid which is selected from the group consisting of M(Met), V(Val), I(Ile), T(Thr), L(Leu), C(Cys), A(Ala), S(Ser), F(Phe), P(Pro), W(Trp), N(Asn), Q(Gln), G(Gly), Y(Tyr), D(Asp), E(Glu), R(Arg), H(His), K(Lys), etc. and is different from the amino acid at the corresponding position in the wild type (for example, substituted with an amino acid which is selected from the group consisting of M(Met), V(Val), I(Ile), T(Thr), L(Leu), C(Cys), A(Ala), etc. and is different from the amino acid at the corresponding position in the wild type), or an amino acid sequence having 95% or higher, 98% or higher, or 99% or higher homology thereto.

For example, the variant of polypeptide may comprise, consist essentially of, or consist of:

an amino acid sequence comprising one or more amino acid mutations selected from the group consisting of Y375M, Y375V, Y375I, Y375T, Y375C, A176C, A176L, P318L, V320L, V320M, and P318A, in the amino acid sequence of SEQ ID NO: 3, or an amino acid sequence having 95% or higher, 98% or higher, or 99% or higher homology thereto.

More specifically, the variant of polypeptide may comprise, consist essentially of, or consist of an amino acid sequence comprising amino acid mutation of Y375M, Y375V, Y375I, Y375T, Y375C, A176C, A176L, P318L+ V320L, V320M, or P318A+V320L, in the amino acid sequence of SEQ ID NO: 3 or an amino acid sequence having 95% or higher, 98% or higher, or 99% or higher homology thereto.

Other embodiment provides a polypeptide variant comprising, consisting essentially of, or consisting of:

an amino acid sequence wherein one or more selected from the group consisting of amino acids affecting to the interaction between PPO-inhibiting herbicides and the polypeptide of PPO, SEQ ID NO: 5 (CyPPO8) (e.g., amino acids positioned on binding sites to PPO-inhibiting herbicides of polypeptide of SEQ ID NO: 5), are respectively and independently deleted or substituted with other amino acid which is different from original amino acid, or an amino acid sequence having 95% or higher, 98% or higher, or 99% or higher homology thereto.

The amino acid residue of polypeptide of SEQ ID NO: 5 which is deleted or substituted with other amino acid that is different from original amino acid (e.g., one or more kinds selected from the group consisting of amino acids positioned in binding sites to PPO-inhibiting herbicides of polypeptide of SEQ ID NO: 5) may be one or more selected from the group consisting of P84, R85, F156, V160, A162, Q179, P306, V308, F327, L330, I343, N362, and F363 of the amino acid sequence of SEQ ID NO: 5.

In one specific embodiment, the variant of polypeptide may comprise, consist essentially of, or consist of:

an amino acid sequence wherein one or more selected from the group consisting of P84, R85, F156, V160, A162, Q179, P306, V308, F327, L330, I343, N362, and F363 of the amino acid sequence of SEQ ID NO: 5 are respectively and independently deleted or substituted with an amino acid which is selected from the group consisting of M(Met), V(Val), I(Ile), T(Thr), L(Leu), C(Cys), A(Ala), S(Ser), F(Phe), P(Pro), W(Trp), N(Asn), Q(Gln), G(Gly), Y(Tyr), D(Asp), E(Glu), R(Arg), H(His), K(Lys), etc. and is different from the amino acid at the corresponding position in the wild type (for example, substituted with an amino acid which is selected from the group consisting of M(Met), V(Val), I(Ile), T(Thr), L(Leu), C(Cys), A(Ala), S(Ser), H(His), G(Gly), etc. and is different from the amino acid at the corresponding position in the wild type), or an amino acid sequence having 95% or higher, 98% or higher, or 99% or higher homology thereto.

For example, the variant of polypeptide may comprise, consist essentially of, or consist of:

an amino acid sequence comprising one or more amino acid mutations selected from the group consisting of P84L, R85A, R85C, R85H, R85L, R85T, R85V, F363M, F363V, F363L, F363C, F363I, F363T, A162C, A162L, P306L, P306A, V308L, V308M, N362S, V160S, V160C, I343V, I343T, F156A, Q179G, F327V, and L330T, in the amino acid sequence of SEQ ID NO: 5, or an amino acid sequence having 95% or higher, 98% or higher, or 99% or higher homology thereto.

More specifically, the variant of polypeptide may comprise, consist essentially of, or consist of:

an amino acid sequence comprising one or more amino acid mutations selected from the group consisting of amino acid mutations of P84L, R85A, R85C, R85H, R85L, R85T, R85V, F363M, F363V, F363L, F363C, F363I, F363T, A162C, A162L, P306L, P306A, V308L, V308M, N362S, V160S, V160C, I343V, I343T, F156A, Q179G, F327V, L330T, P84L+F363M, R85A+F363M, R85A+F363I, R85C+F363M, R85H+F363M, R85L+F363M, R85T+ F363M, R85V+F363M, R85A+A162L+F363M, R85A+ A162L+F363I, R85A+A162C+F363M, R85A+A162C+ F363I, R85A+V308M+F363M, V160S+F363M, V160S+

F363I, V160S+V308M+F363I, A162L+F363M, A162C+ F363M, A162C+F363I, A162C+F363L, A162C+V308M+ F363M, A162C+V308L+F363M, A162L+Q179G+F363M, P306A+V308L, P306L+V308L, V308M+F363M, V308M+ F363I, I343T+F363M, I343V+F363M, and N362S+F363M, in the amino acid sequence of SEQ ID NO: 5, or an amino acid sequence having 95% or higher, 98% or higher, or 99% or higher homology thereto.

The polypeptide variant comprising, consisting essentially of, or consisting of an amino acid sequence having sequence homology (for example, 95% or higher, 98% or higher, or 99% or higher sequence homology) described herein may maintain enzyme activity equivalent to that of a polypeptide having an amino acid sequence which is a standard of identification of sequence homology (for example, the PPO protein having amino acid mutation described above), for example, 5% or higher, 10% or higher, 20% or higher, 30% or higher, 40% or higher, 50% or higher, 60% or higher, 70% or higher, 80% or higher, 90% or higher, or 95% or higher enzyme activity to a polypeptide having an amino acid sequence which is a standard in plants (in a whole plant, in a plant cell or cell culture, in a plant tissue, etc.), in algae, and/or in vitro, and having function to confer herbicide tolerance. The sequence homology description is used in order to clarify that the herbicide-tolerance PPO protein variant or polypeptide variant described herein may comprise all sequence mutations in the range of satisfying the above condition (maintain enzyme activity and having function to confer herbicide tolerance).

The names of amino acids used in the description are arranged as follows:

| Amino acid | 3-letter code | 1-letter code |
|---|---|---|
| Alanine | Ala | A |
| Isoleucine | Ile | I |
| Leucine | Leu | L |
| Methionine | Met | M |
| Phenylalanine | Phe | F |
| Proline | Pro | P |
| Tryptophan | Trp | W |
| Valine | Val | V |
| Aspargine | Asn | N |
| Cysteine | Cys | C |
| Glutamine | Gln | Q |
| Glycine | Gly | G |
| Serine | Ser | S |
| Threonine | Thr | T |
| Tyrosine | Tyr | Y |
| Aspartic acid | Asp | D |
| Glutamic acid | Glu | E |
| Arginine | Arg | R |
| Histidine | His | H |
| Lysine | Lys | K |

The polypeptide variant (herbicide-tolerant PPO protein variant) may maintain enzyme activity of PPO protein, and exhibit enhanced herbicide tolerance compared to the wild type.

In addition, the herbicide-tolerant PPO protein variant may comprise further mutation exhibiting biologically equal activity to a polypeptide consisting of SEQ ID NO: 1, SEQ ID NO: 3, SEQ ID NO: 5, or an amino acid sequence having amino acid mutation described above. For example, the additional mutation may be amino acid substitution which does not overall alter molecular activity, and such amino acid substitution is publicly known in the art. In one example, the additional substitution may be substitution of amino acid residues Ala/Ser, Val/Ile, Asp/Glu, Thr/Ser, Ala/Gly, Ala/Thr, Ser/Asn, Ala/Val, Ser/Gly, Thr/Phe, Ala/Pro, Lys/Arg, Asp/Asn, Leu/Ile, Leu/Val, Ala/Glu, or Asp/Gly, but not limited thereto. In some cases, the herbicide-tolerant PPO protein variant may be under modification by one or more kinds selected from the group consisting of phosphorylation, sulfation, acylation, glycosylation, methylation, farnesylation, etc. In addition, the herbicide-tolerant PPO protein variant may comprise a protein variant wherein structural stability to heat, pH, etc. of the protein is increased or protein activity is increased by amino acid variation (mutation) and/or modification.

The term "sequence homology" refers to the degree of similarity to the wild type or reference amino acid sequence or nucleotide sequence, and any protein may be included in the scope of the present invention, as long as it includes amino acid residues having 60% or higher, 65% or higher, 70% or higher, 75% or higher, 80% or higher, 85% or higher, 90% or higher, 95% or higher, 98% or higher, or 99% or higher identity to the amino acid sequence of the herbicide-tolerant PPO protein and retains a biological activity equivalent to the herbicide-tolerant PPO protein variant. Such protein homologues may comprise an active site equivalent to that of a targeted protein. Such homology comparison may be conducted by eye or with the aid of readily available comparison programs. Commercially available computer programs may calculate percent (%) homology between two or more sequences, and homology (%) may be calculated over contiguous sequences. The sequence alignment for comparison may be conducted by methods known in the art, for example, GAP, BESTFIT, BLAST, FASTA and TFASTA.

The herbicide-tolerant PPO protein or its variant may be obtained by extracting from nature and purifying by methods well known in the art. Otherwise, it may be obtained as a recombinant protein using a gene recombination technology. In case of using a gene recombination technology, it may be obtained by a process of collecting herbicide-tolerant PPO protein or its variant from a host cell, after introducing a nucleic acid encoding the herbicide-tolerant PPO protein or its variant into an appropriate expression vector, and transforming a host cell with the vector in order to express a targeted protein. After the protein is expressed in a selected host cell, general biochemical separation techniques, for example, treatment with a protein precipitating agent (salting out), centrifugation, ultrasonic disruption, ultrafiltration, dialysis, chromatography such as molecular sieve chromatography (gel filtration), adsorption chromatography, ion exchange chromatography, affinity chromatography and the like may be used for the isolation and purification thereof, and in order to separate the protein with a high purity, these methods may be used in combination.

The herbicide-tolerant PPO nucleic acid molecule (polynucleotide encoding the PPO protein or its variant) may be isolated or prepared using standard molecular biological techniques, for example, a chemical synthesis or recombination method, or commercially available one may be used.

In a specific embodiment, the PPO proteins were found to exhibit broad herbicide tolerance against representative 9 families of PPO inhibiting herbicides classified according to their chemical structures in a herbicide tolerance test system using PPO-deficient *E. coli* BT3(ΔPPO). It was also found that the proteins may be expressed in tobacco leaves by *Agrobacterium*-mediated transformation, and they may be also expressed in the chloroplast of a plant by using a transit peptide (TP). Further, it was found that the PPO proteins may be also expressed in *Arabidopsis thaliana* ecotype Columbia-0 (*A. thaliana*) by a plant expression vector. Even though the transformed plants are treated with PPO inhibiting herbicides, germination and growth of the plants are observed. Furthermore, inheritance of the above herbicide-tolerant traits to the next generation was confirmed by an inheritance study.

Therefore, the PPO protein and its variants provided herein may be introduced into a plant or an alga, thereby being used for enhancement of the herbicide tolerance of the plant or the alga.

One embodiment provides a composition for conferring and/or enhancing herbicide tolerance of plants and/or algae, comprising one or more selected from the group consisting of:

(1) a polypeptide comprising, consisting essentially of, or consisting of SEQ ID NO: 1, SEQ ID NO: 3, SEQ ID NO: 5, or an amino acid sequence having 95% or higher, 98% or higher, or 99% or higher homology thereto;

(2) the above-described polypeptide variant;

(3) a polynucleotide encoding the polypeptide (1) or the polypeptide variant (2);

(4) a recombinant vector comprising the polynucleotide; and (5) a recombinant cell comprising the recombinant vector.

The herbicide herein refers to an active ingredient that kills, controls, or otherwise adversely modifies the growth of plants or algae. In addition, the herbicide tolerance or herbicide tolerance means that even after treatment of a herbicide which normally kills a normal or wild-type plant or normally inhibits growth thereof, inhibition of the plant growth is weakened or eliminated, compared to that of the normal or wild-type plant, and therefore, the plant continues to grow. The herbicide includes a herbicide inhibiting protoporphyrinogen oxidase (PPO) of a plant or an alga. Such PPO-inhibiting herbicide may be classified into pyrimidinediones, diphenyl-ethers, phenylpyrazoles, N-phenylphthalimides, thiadiazoles, oxadiazoles, triazolinones, oxazolidinediones, and other herbicides according to their chemical structures.

As a specific embodiment, the pyrimidinediones herbicide includes butafenacil, saflufenacil, benzfendizone, and tiafenacil, but is not limited thereto.

The diphenyl-ethers herbicide includes fomesafen, oxyfluorfen, aclonifen, acifluorfen, bifenox, ethoxyfen, lactofen, chlomethoxyfen, chlorintrofen, fluoroglycofen-ethyl and halosafen, but not limited thereto.

The phenylpyrazoles herbicide includes pyraflufen-ethyl and fluazolate, but not limited thereto.

The phenylphthalimides herbicide includes flumioxazin, cinidon-ethyl and flumiclorac-pentyl, but not limited thereto.

The phenylesters herbicide includes phenopylate (2,4-dichlorophenyl 1-pyrrolidinecarboxylate) and carbamate analogues of phenopylate (for example, 0-phenylpyrrolidino- and piperidinocarbamate analoges (refer to "Ujjana B. Nandihalli, Mary V. Duke, Stephen O. Duke, Relationships between molecular properties and biological activities of O-phenyl pyrrolidino- and piperidinocarbamate herbicides, J. Agric. Food Chem., 1992, 40(10) 1993-2000")), etc., but not limited thereto. In one embodiment, the carbamate analogue of phenopylate may be one or more kinds selected from the group consisting of pyrrolidine-1-carboxylic acid phenyl ester (CAS No. 55379-71-0), 1-pyrrolidinecarboxylic acid, 2-chlorophenyl ester (CAS No. 143121-06-6), 4-chlorophenyl pyrrolidine-1-carboxylate (CAS No. 1759-02-0), carbamic acid, diethyl-2,4-dichloro-5-(2-propynyloxy)phenyl ester (9CI) (CAS No. 143121-07-7), 1-pyrrolidinecarboxylic acid, 2,4-dichloro-5-hydroxyphenyl ester (CAS No. 143121-08-8), 2,4-dichloro-5-(methoxycarbonyl) phenyl pyrrolidine-1-carboxylate (CAS No. 133636-94-9), 2,4-dichloro-5-[(propan-2-yloxy)carbonyl]phenyl pyrrolidine-1-carboxylate (CAS No. 133636-96-1), 1-piperidinecarboxylic acid, 2,4-dichloro-5-(2-propynyloxy)phenyl ester (CAS No. 87374-78-5), 2,4-dichloro-5-(prop-2-yn-1-yloxy)phenyl pyrrolidine-1-carboxylate (CAS No. 87365-63-7), 2,4-dichloro-5-(prop-2-yn-1-yloxy)phenyl 4,4-difluoropiperidine-1-carboxylate (CAS No. 138926-22-4), 1-pyrrolidinecarboxylic acid, 3,3-difluoro-2,4-dichloro-5-(2-propyn-1-yloxy)phenyl ester (CAS No. 143121-10-2), 4-chloro-2-fluoro-5-[(propan-2-yloxy)carbonyl]phenyl pyrrolidine-1-carboxylate (CAS No. 133636-98-3), etc.

The thiadiazoles herbicide includes fluthiacet and thidiazimin, but not limited thereto.

The oxadiazoles herbicide includes oxadiargyl and oxadiazon, but not limited thereto.

The triazolinones herbicide includes carfentrazone, sulfentrazone and azafenidin, but not limited thereto.

The oxazolidinediones herbicide includes pentoxazone, but not limited thereto.

The other herbicide includes pyraclonil, flufenpyr-ethyl and profluazol, but not limited thereto.

The herbicide-tolerant PPO gene provided herein may be introduced into a plant or an alga by various methods known in the art, and preferably, by using an expression vector for plant or alga transformation.

In case of plant transformation, an appropriate promoter which may be included in the vector may be any promoter generally used in the art for introduction of the gene into the plant. For example, the promoter may include an SP6 promoter, a T7 promoter, a T3 promoter, a PM promoter, a maize ubiquitin promoter, a cauliflower mosaic virus (CaMV) 35S promoter, a nopaline synthase (nos) promoter, a figwort mosaic virus 35S promoter, a sugarcane bacilliform virus promoter, a commelina yellow mottle virus promoter, a light-inducible promoter from the small subunit of ribulose-1,5-bisphosphate carboxylase (ssRUBISCO), a rice cytosolic triosephosphate isomerase (TPI) promoter, an adenine phosphoribosyltransferae (APRT) promoter of *A. thaliana*, an octopine synthase promoter, and a BCB (blue copper binding protein) promoter, but is not limited thereto.

Further, the vector may include a poly A signal sequence causing polyadenylation of 3'-terminus, and for example, it may include NOS 3'-end derived from a nopaline synthase gene of *Agrobacterium tumefaciens*, an octopine synthase terminator derived from an octopine synthase gene of *Agrobacterium tumefaciens*, 3'-end of protease inhibitor I or II gene of tomato or potato, a CaMV 35S terminator, a rice α-amylase terminator RAmy1 A, and a phaseoline terminator, but is not limited thereto.

In addition, chloroplast-specific promoter, nucleus promoter, constitutive promoter, or inducible promoter may be used for introduction of the gene into the algae as a promoter. The herbicide-tolerant PPO gene or its variant provided herein may be designed in order to operationally link to 5' UTR or 3' UTR, thereby expressing function in nucleus of algae. In addition, the vector may further comprise a transcriptional regulatory sequence which is appropriate to transformation of algae. A recombinant gene conferring herbicide tolerance may be integrated to genome of nucleus or genome of chloroplast in a host alga, but not limited thereto.

In addition, in the vector, a transit peptide required for targeting to chloroplasts may be linked to 5'-end of the PPO gene in order to express the herbicide-tolerant PPO gene in the chloroplasts.

In addition, optionally, the vector may further include a gene encoding selectable marker as a reporter molecule, and example of the selectable marker may include antibiotics (e.g., neomycin, carbenicillin, kanamycin, spectinomycin, hygromycin, bleomycin, chloramphenicol, ampicillin etc.) or herbicide (glyphosate, glufosinate, phosphinothricin, etc.)-tolerant genes, but is not limited thereto.

Further, the recombinant vector for plant expression may include an *Agrobacterium* binary vector, a cointegration vector, or a general vector which has no T-DNA region but is designed to be expressed in the plant. Of them, the binary vector refers to a vector containing two separate vector systems harboring one plasmid responsible for migration consisting of left border (LB) and right border (RB) in Ti (tumor inducible) plasmid, and the other plasmid for target gene-transferring, and the vector may include a promoter region and a polyadenylation signal sequence for expression in plants.

When the binary vector or cointegration vector is used, a strain for transformation of the recombinant vector into the plant is preferably *Agrobacterium* (*Agrobacterium*-mediated transformation). In this regard, *Agrobacterium tumefaciens* or *Agrobacterium rhizogenes* may be used. In addition, when the vector having no T-DNA region is used, electroporation, particle bombardment, polyethylene glycol-mediated uptake, etc. may be used for introduction of the recombinant plasmid into the plant.

The plant transformed with the gene by the above method may be redifferentiated into a plant through callus induction, rhizogenesis, and soil acclimatization using a standard technique known in the art.

The plant subjected to transformation herein is understood by a meaning including a plant cell (containing a suspension-cultured cell), a protoplast, a callus, a hypocotyl, a seed, a cotyledon, a shoot as well as a mature plant.

Further, the scope of the transformant includes a transformant introduced with the gene as well as a clone or progeny thereof ($T_1$ generation, $T_2$ generation, $T_3$ generation, $T_4$ generation, $T_5$ generation, or any subsequent generations). For example, the transformed plant also includes a plant having the inherited herbicide tolerance traits as sexual and asexual progeny of the plant transformed with the gene provided herein. The scope of the present invention also includes all mutants and variants showing the characteristics of the initial transformed plant, together with all hybridization and fusion products of the plant transformed with the gene provided herein. Furthermore, the scope of the present invention also includes a part of the plant, such as a seed, a flower, a stem, a fruit, a leaf, a root, a tuber, and/or a tuberous root, which is originated from a transformed plant which is transformed in advance by the method of the present invention, or a progeny thereof, and is composed of at least a part of the transformed cells.

The plant, to which the present invention is applied, is not particularly limited to, but may be at least one selected from the group consisting of monocotyledonous or dicotyledonous plants. Further, the plant includes herbaceous plants or woody plants. The monocotyledonous plant may include plants belonging to the family Alismataceae, Hydrocharitaceae, Juncaginaceae, Scheuchzeriaceae, Potamogetonaceae, Najadaceae, Zosteraceae, Liliaceae, Haemodoraceae, Agavaceae, Amaryllidaceae, Dioscoreaceae, Pontederiaceae, Iridaceae, Burmanniaceae, Juncaceae, Commelinaceae, Eriocaulaceae, Gramineae (Poaceae), Araceae, Lemnaceae, Sparganiaceae, Typhaceae, Cyperaceae, Musaceae, Zingiberaceae, Cannaceae, Orchidaceae, but not limited thereto.

The dicotyledonous plant may include plants belonging to the family Diapensiaceae, Clethraceae, Pyrolaceae, Ericaceae, Myrsinaceae, Primulaceae, Plumbaginaceae, Ebenaceae, Styracaceae, Symplocaceae, Symplocaceae, Oleaceae, Loganiaceae, Gentianaceae, Menyanthaceae, Apocynaceae, Asclepiadaceae, Rubiaceae, Polemoniaceae, Convolvulaceae, Boraginaceae, Verbenaceae, Labiatae, Solanaceae, Scrophulariaceae, Bignoniaceae, Acanthaceae, Pedaliaceae, Orobanchaceae, Gesneriaceae, Lentibulariaceae, Phrymaceae, Plantaginaceae, Caprifoliaceae, Adoxaceae, Valerianaceae, Dipsacaceae, Campanulaceae, Compositae, Myricaceae, Juglandaceae, Salicaceae, Betulaceae, Fagaceae, Ulmaceae, Moraceae, Urticaceae, Santalaceae, Loranthaceae, Polygonaceae, Phytolaccaceae, Nyctaginaceae, Aizoaceae, Portulacaceae, Caryophyllaceae, Chenopodiaceae, Amaranthaceae, Cactaceae, Magnoliaceae, Illiciaceae, Lauraceae, Cercidiphyllaceae, Ranunculaceae, Berberidaceae, Lardizabalaceae, Menispermaceae, Nymphaeaceae, Ceratophyllaceae, Cabombaceae, Saururaceae, Piperaceae, Chloranthaceae, Aristolochiaceae, Actinidiaceae, Theaceae, Guttiferae, Droseraceae, Papaveraceae, Capparidaceae, Cruciferae, Platanaceae, Hamamelidaceae, Crassulaceae, Saxifragaceae, Eucommiaceae, Pittosporaceae, Rosaceae, Leguminosae, Oxalidaceae, Geraniaceae, Tropaeolaceae, Zygophyllaceae, Linaceae, Euphorbiaceae, Callitrichaceae, Rutaceae, Simaroubaceae, Meliaceae, Polygalaceae, Anacardiaceae, Aceraceae, Sapindaceae, Hippocastanaceae, Sabiaceae, Balsaminaceae, Aquifoliaceae, Celastraceae, Staphyleaceae, Buxaceae, Empetraceae, Rhamnaceae, Vitaceae, Elaeocarpaceae, Tiliaceae, Malvaceae, Sterculiaceae, Thymelaeaceae, Elaeagnaceae, Flacourtiaceae, Violaceae, Passifloraceae, Tamaricaceae, Elatinaceae, Begoniaceae, Cucurbitaceae, Lythraceae, Punicaceae, Onagraceae, Haloragaceae, Alangiaceae, Cornaceae, Araliaceae, and Umbelliferae (Apiaceae), but not limited thereto.

In a specific embodiment, the plant may be one or more kinds selected from the group consisting of food crops such as rice, wheat, barley, corn, soybean, potato, red bean, oat, and sorghum; vegetable crops such as Chinese cabbage, radish, red pepper, strawberry, tomato, watermelon, cucumber, cabbage, oriental melon, pumpkin, welsh onion, onion, and carrot; crops for special use such as ginseng, tobacco, cotton, soilage, forage, sesame, sugar cane, sugar beet, *Perilla* sp., peanut, rapeseed, grass, and castor-oil plant; fruit trees such as apple tree, pear tree, jujube tree, peach tree, kiwi fruit tree, grape tree, citrus fruit tree, persimmon tree, plum tree, apricot tree and banana tree; woody plants such as pine, palm oil, and eucalyptus; flowering crops such as rose, gladiolus, gerbera, carnation, chrysanthemum, lily and tulip; and fodder crops such as ryegrass, red clover, orchardgrass, alfalfa, tall fescue and perennial ryegrass, but is not limited thereto. As a specific embodiment, the plant may be one or more kinds selected from the group consisting of dicotyledonous plants such as *Arabidopsis*, potato, eggplant, tobacco, red pepper, tomato, burdock, crown daisy, lettuce, balloon flower, spinach, chard, sweet potato, celery, carrot, water dropwort, parsley, Chinese cabbage, cabbage, radish, watermelon, oriental melon, cucumber, pumpkin, gourd, strawberry, soybean, mung bean, kidney bean, and pea; and monocotyledonous plants such as rice, wheat, barley, corn, sorghum, etc., but are not limited thereto.

The alga, to which the present invention is applied, is not particularly limited to, but includes Prokaryotic algae or Eukaryotic algae. For example, the alga may be cyanobacteria, green algae, red algae, brown algae, macroalgae, or microalgae.

The cyanobacteria includes Chroococcales phylum (for example, *Aphanocapsa, Aphanothece, Chamaesiphon, Chondrocystis, Chroococcus, Chroogloeocystis, Crocosphaera, Cyanobacterium, Cyanobium, Cyanodictyon, Cyanosarcina, Cyanothece, Dactylococcopsis, Gloeocapsa, Gloeothece, Halothece, Johannesbaptistia, Merismopedia, Microcystis, Radiocystis, Rhabdoderma, Snowella, Synechococcus, Synechocystis, Thermosynechococcus, Woronichinia*), Gloeobacteria phylum, Nostocales phylum (for example, Microchaetaceae, Nostocaceae, Rivulariaceae, Scytonemataceae), Oscillatoriales phylum (for example, *Arthronema, Arthrospira, Blennothrix, Crinalium, Geitlerinema, Halomicronema, Halospirulina, Hydrocoleum, Jaaginema, Katagnymene, Komvophoron, Leptolyngbya, Limnothrix, Lyngbya, Microcoleus, Oscillatoria, Phormidium, Planktothricoides, Planktothrix, Plectonema, Pseudanabaena, Pseudophormidium, Schizothrix, Spirulina, Starria, Symploca, Trichodesmium, Tychonema*), Pleurocapsales phylum (for example, *Chroococcidiopsis, Dermocarpa, Dermocarpella, Myxosarcina, Pleurocapsa, Solentia, Stanieria, Xenococcus*), Prochlorales phylum, or Stigonematales phylum (for example, *Capsosira, Chlorogloeopsis, Fischerella, Hapalosiphon, Mastigocladopsis, Mastigocladus, Nostochopsis, Stigonema, Symphyonema, Symphonemopsis, Umezakia, Westiellopsis*), etc.

As another example of algae, *Chlorophyta, Chlamydomonas, Volvacales, Dunaliella, Scenedesmus, Chlorella,* or *Hematococcm* may be exemplified.

As other example of algae, *Phaeodactylum tricornutum, Amphiprora hyaline, Amphora* spp., *Chaetoceros muelleri, Navicula saprophila, Nitzschia communis, Scenedesmus dimorphus, Scenedesmus obliquus, Tetraselmis suecica, Chlamydomonas reinhardtii, Chlorella vulgaris, Haematococcus pluvialis, Neochloris oleoabundans, Synechococcus elongatus, Botryococcus braunii, Gloeobacter violaceus, Synechocystis, Thermosynechococcus elongatus, Nannochloropsis oculata, Nannochloropsis salina, Nannochloropsis gaditana, Isochrysis galbana, Botryococcus sudeticus, Euglena gracilis, Neochloris oleoabundans, Nitzschia palea, Pleurochrysis carterae, Tetraselmis chuii, Pavlova* spp., *Aphanocapsa* spp., *Synechosystis* spp., *Nannochloris* spp., etc. may be exemplified. However, it is not limited to kinds listed above, and algae belonging to other various genus and family may be comprised.

The plant or alga introduced with the herbicide-tolerant PPO or its variant provided herein may exhibit tolerance against two or more of PPO-inhibiting herbicides.

Therefore, the technology provided herein may be used to control weeds or remove undesired aquatic organisms by using two or more kinds of PPO-inhibiting herbicides sequentially or simultaneously.

One embodiment provides a method of controlling weeds in a cropland, comprising a step of providing the cropland with a plant comprising the herbicide-tolerant PPO protein, its variant, or a gene encoding thereof described above, and a step of applying an effective dosage of protoporphyrinogen oxidase-inhibiting herbicide to the cropland.

Another embodiment provides a method of removing an undesired aquatic organism from a culture medium, comprising a step of providing a culture medium with algae comprising the herbicide-tolerant PPO protein, its variant, or a gene encoding thereof described above, and a step of applying an effective dosage of protoporphyrinogen oxidase-inhibiting herbicide to the culture medium.

In addition, the herbicide-tolerant PPO protein, its variant, or a gene encoding thereof provided herein may be used in combination of a second herbicide-tolerant polypeptide or a gene encoding thereof.

Therefore, the plant or alga introduced with the herbicide-tolerant PPO provided herein may exhibit tolerance against two or more of herbicides which are different from each other in mechanism of action. In the present invention, two or more of different herbicides including the PPO-inhibiting herbicide, which are different from each other in mechanism of action, may be used sequentially or simultaneously, thereby controlling weeds and/or removing undesired aquatic organisms. Hereinafter, the herbicide which is different from the PPO-inhibiting herbicide in the mechanism of action is called "second herbicide".

One embodiment provides a composition for conferring or enhancing herbicide tolerance of plants or algae, comprising the above-described herbicide-tolerant PPO protein, its variant, or a gene encoding thereof; and the second herbicide-tolerant polypeptide or a gene encoding thereof.

Another embodiment provides a transformant having herbicide tolerance of plants or algae, or a clone or progeny thereof, comprising the above-described herbicide-tolerant PPO protein, its variant, or a gene encoding thereof; and the second herbicide-tolerant polypeptide or a gene encoding thereof.

Other embodiment provides a method of preparing plants or algae having herbicide tolerance, comprising a step of transforming algae, or plant cell, protoplast, callus, hypocotyl, seed, cotyledon, shoot, or whole plant with the above-described herbicide-tolerant PPO protein, its variant, or a gene encoding thereof; and the second herbicide-tolerant polypeptide or a gene encoding thereof.

Other embodiment provides a method of controlling weeds in a cropland, comprising a step of providing the cropland with a plant comprising the above-described herbicide-tolerant PPO protein, its variant, or a gene encoding thereof; and the second herbicide-tolerant polypeptide or a gene encoding thereof, and a step of applying an effective dosage of protoporphyrinogen oxidase-inhibiting herbicide to the cropland.

Other embodiment provides a method of removing an undesired aquatic organism from a culture medium, comprising a step of providing a culture medium with algae comprising the herbicide-tolerant PPO protein, its variant, or a gene encoding thereof; and the second herbicide-tolerant polypeptide or a gene encoding thereof, and a step of applying an effective dosage of protoporphyrinogen oxidase-inhibiting herbicide to the culture medium.

For example, the plant or alga further includes the second herbicide-tolerance polypeptide or a gene encoding thereof, thereby having novel and/or enhanced tolerance against the second herbicide.

For example, the second herbicide may include cell division-inhibiting herbicides, photosynthesis-inhibiting herbicides, amino acid synthesis-inhibiting herbicides, plastid-inhibiting herbicides, cell membrane-inhibiting herbicides, and/or any combinations thereof, but is not limited thereto. The second herbicide may be exemplified by glyphosate, glufosinate, dicamba, 2,4-D (2,4-dichlorophenoxyacetic acid), ALS (acetolactate synthase)-inhibiting herbicides (for example, imidazolidinone, sulfonylurea, triazole pyrimidine, sulphonanilide, pyrimidine thiobenzoate, etc.), photosystem II-inhibiting herbicides, phenylurea-based herbicides, plastid-inhibiting herbicides, bromoxynil-based herbicides, and/or any combinations thereof, but is not limited thereto.

For example, the second herbicide-tolerant polypeptide may be exemplified as one or more kinds selected from the group consisting of glyphosate herbicide-tolerant EPSPS (glyphosate tolerant 5-enolpyruvylshikimate-3-phosphate synthase), GOX (glyphosate oxidase), GAT (glyphosate-N-acetyltransferase) or glyphosate decarboxylase; glufosinate herbicide-tolerant PAT (phosphinothricin-N-acetyltransferase); dicamba herbicide-tolerant DMO (dicamba monooxygenase); 2,4-D herbicide-tolerant 2,4-D monooxygenase or AAD (aryloxyalkanoate dioxygenase); ALS-inhibiting sulfonylurea-based herbicide-tolerant ALS (acetolactate synthase), AHAS (acetohydroxyacid synthase), or AtAHASL (acetohydroxyacid synthase large subunit); photosystem II-inhibiting herbicide-tolerant photosystem II protein D1; phenylurea-based herbicide-tolerant cytochrome P450; plastid-inhibiting herbicide-tolerant HPPD (hydroxylphenylpyruvate dioxygenase); bromoxynil herbicide-tolerant nitrilase; and any combinations thereof, but is not limited thereto.

Further, the gene encoding the second herbicide-tolerant polypeptide may be exemplified as one or more kinds selected from the group consisting of glyphosate herbicide-tolerant cp4 epsps, epsps (AG), mepsps, 2mepsps, goxv247, gat4601 or gat4621 gene; glufosinate herbicide-tolerant bar, pat or pat (SYN) gene; dicamba herbicide-tolerant dmo gene; 2,4-D herbicide-tolerant AAD-1 or AAD-12 gene; ALS-inhibiting sulfonylurea-based herbicide-tolerant ALS, GM-HRA, S4-HRA, ZM-HRA, Csr1, Csr1-1, Csr1-2, SurA or SurB; photosystem II-inhibiting herbicide-tolerant psba gene; phenylurea herbicide-tolerant CYP76B1 gene; isoxaflutole herbicide-tolerant HPPDPF W336 gene; bromoxynil herbicide-tolerant bxn gene; and any combinations thereof, but is not limited thereto.

Advantageous Effects

A variant of herbicide-tolerant PPO protein or a gene encoding thereof provided herein is applied to plants or algae, thereby conferring and/or enhancing more excellent herbicide tolerance traits, and the selective control is performed using herbicides, thereby economically controlling weeds or removing aquatic organisms.

DESCRIPTION OF DRAWINGS

The patent or application file contains at least one drawing executed in color. Copies of this patent or patent application publication with color drawing(s) will be provided by the Patent and Trademark Office upon request and payment of the necessary fee.

FIG. 1 is a photograph showing cell growth level in case of treating tiafenacil at a concentration of 0 μM (micromole), 25 μM, 50 μM, 100 μM and 400 μM, after transforming PPO-deficient BT3 *E. coli* (BT3(ΔPPO)) with pACBB empty vector (indicated by V), *A. thaliana* PPO1 gene (indicated by WT), CyPPO2 wild type gene (indicated by Cy2), CyPPO4 wild type gene (indicated by Cy4), or CyPPO8 wild type gene (indicated by Cy8).

FIG. 2 is the map of pET29b vector.

FIG. 3 is the map of pACBB-eGFP vector.

FIG. 4 is the map of pET303-CT-His vector.

FIG. 5 is a photograph showing cell growth level of PPO-deficient BT3 *E. coli* (BT3(ΔPPO)) transformant transformed with CyPPO2 wild type gene (indicated by Cy2 WT), or various CyPPO2 mutant genes, when treated with tiafenacil at a concentration of 0 μM, 5 μM, 25 μM, 50 μM, 100 μM and 200 μM, respectively.

FIG. 6 is a photograph showing cell growth level of BT3(ΔPPO) transformant transformed with Cy2 WT, or various CyPPO2 mutant genes, when treated with saflufenacil at a concentration of 0 μM, 5 μM, 25 μM, 50 μM, 100 μM and 200 μM, respectively.

FIG. 7 is a photograph showing cell growth level of BT3(ΔPPO) transformant transformed with Cy2 WT or various CyPPO2 mutant genes, when treated with flumioxazin at a concentration of 0 μM, 5 μM, 25 μM, 50 μM, 100 μM and 200 μM, respectively.

FIG. 8 is a photograph showing cell growth level of BT3(ΔPPO) transformant transformed with Cy2 WT or various CyPPO2 mutant genes, when treated with fomesafen at a concentration of 0 μM, 5 μM, 25 μM, 50 μM, 100 μM and 200 μM, respectively.

FIG. 9 is a photograph showing cell growth level of BT3(ΔPPO) transformant transformed with Cy2 WT or various CyPPO2 mutant genes, when treated with acifluorfen at a concentration of 0 μM, 5 μM, 25 μM, 50 μM, 100 μM and 200 μM, respectively.

FIG. 10 is a photograph showing cell growth level of BT3(ΔPPO) transformant transformed with Cy2 WT or various CyPPO2 mutant genes, when treated with pyraclonil at a concentration of 0 μM, 5 μM, 25 μM, 50 μM, 100 μM and 200 μM, respectively.

FIG. 11 is a photograph showing cell growth level of BT3(ΔPPO) transformant transformed with Cy2 WT or various CyPPO2 mutant genes, when treated with sulfentrazone at a concentration of 0 μM, 5 μM, 25 μM, 50 μM, 100 μM and 200 μM, respectively.

FIG. 12 is a photograph showing cell growth level of BT3(ΔPPO) transformant transformed with Cy2 WT or various CyPPO2 mutant genes, when treated with pentoxazone at a concentration of 0 μM, 5 μM, 25 μM, 50 μM, 100 μM and 200 μM, respectively.

FIG. 13 is a photograph showing cell growth level of BT3(ΔPPO) transformant transformed with Cy2 WT or various CyPPO2 mutant genes, when treated with pyraflufen-ethyl at a concentration of 0 μM, 5 μM, 25 μM, 50 μM, 100 μM and 200 μM, respectively.

FIG. 14 is a photograph showing cell growth level of BT3(ΔPPO) transformant transformed with CyPPO4 wild type gene (indicated by Cy4 WT) or various CyPPO4 mutant genes, when treated with tiafenacil at a concentration of 0 μM, 5 μM, 25 μM, 50 μM, 100 μM and 200 μM, respectively.

FIG. 15 is a photograph showing cell growth level of BT3(ΔPPO) transformant transformed with Cy4 WT or various CyPPO4 mutant genes, when treated with saflufenacil at a concentration of 0 μM, 5 μM, 100 μM and 200 μM, respectively.

FIG. 16 is a photograph showing cell growth level of BT3(ΔPPO) transformant transformed with Cy4 WT or various CyPPO4 mutant genes, when treated with flumioxazin at a concentration of 0 μM, 5 μM, 100 μM and 200 μM, respectively.

FIG. 17 is a photograph showing cell growth level of BT3(ΔPPO) transformant transformed with CyPPO8 wild type gene (indicated by Cy8 WT) or various CyPPO8 mutant genes, when treated with tiafenacil at a concentration of 0 μM, 5 μM, 25 μM, 50 μM, 100 μM, 200 μM and 400 μM, respectively, wherein the top is a result obtained by using pET303-CT-His vector, and the bottom is a result obtained by using pACBB vector.

FIG. 18 is a photograph showing cell growth level of BT3(ΔPPO) transformant transformed with Cy8 WT or various CyPPO8 mutant genes, when treated with saflufenacil at a concentration of 0 µM, 5 µM, 25 µM, 50 µM, 100 µM and 200 µM, respectively.

FIG. 19 is a photograph showing cell growth level of BT3(ΔPPO) transformant transformed with Cy8 WT or various CyPPO8 mutant genes, when treated with fomesafen at a concentration of 0 µM, 5 µM, 25 µM, 50 µM, 100 µM and 200 µM, respectively.

FIG. 20 is a photograph showing cell growth level of BT3(ΔPPO) transformant transformed with Cy8 WT or various CyPPO8 mutant genes, when treated with acifluorfen at a concentration of 0 µM, 5 µM, 25 µM, 50 µM, 100 µM and 200 µM, respectively.

FIG. 21 is a photograph showing cell growth level of BT3(ΔPPO) transformant transformed with Cy8 WT or various CyPPO8 mutant genes, when treated with flumioxazin at a concentration of 0 µM, 5 µM, 25 µM, 50 µM, 100 µM and 200 µM, respectively.

FIG. 22 is a photograph showing cell growth level of BT3(ΔPPO) transformant transformed with Cy8 WT or various CyPPO8 mutant genes, when treated with sulfentrazone at a concentration of 0 µM, 5 µM, 25 µM, 50 µM, 100 µM and 200 µM, respectively.

FIG. 23 is a photograph showing cell growth level of BT3(ΔPPO) transformant transformed with Cy8 WT or various CyPPO8 mutant genes, when treated with pentoxazone at a concentration of 0 µM, 5 µM, 25 µM, 50 µM, 100 µM and 200 µM, after respectively.

FIG. 24 is a photograph showing cell growth level of BT3(ΔPPO) transformant transformed with Cy8 WT or various CyPPO8 mutant genes, when treated with pyraflufen-ethyl at a concentration of 0 µM, 5 µM, 25 µM, 50 µM, 100 µM and 200 µM, respectively.

FIG. 25 is a photograph showing cell growth level of BT3(ΔPPO) transformant transformed with Cy8 WT or various CyPPO8 mutant genes, when treated with pyraclonil at a concentration of 0 µM, 5 µM, 25 µM, 50 µM, 100 µM and 200 µM, respectively.

FIG. 26 is a schematic diagram showing a recombinant vector for preparing a fusion protein wherein MBP (maltose binding protein) and PPO protein are fused.

FIG. 27 is the map of pMAL-c2X vector.

FIG. 28 shows the result of SDS-PAGE to isolate and purify CyPPO2 wild type protein and CyPPO2-Y373M variant protein.

FIG. 29 shows the result of SDS-PAGE to isolate and purify CyPPO4 wild type protein and CyPPO4-Y375M variant protein.

FIG. 30 shows the result of SDS-PAGE to isolate and purify CyPPO8 wild type protein and CyPPO8-F363M variant protein.

FIG. 31 is a schematic diagram exemplarily showing the structure of binary vector for plant transformation of CyPPO genes.

FIG. 32 shows germination level of seeds of A. thaliana ($T_2$) transformant wherein mutant gene of CyPPO2, CyPPO4 or CyPPO8 is introduced, when germinating the seeds in a medium comprising various concentrations of tiafenacil. Col-O means non-transgenic A. thaliana.

FIG. 33 shows the western blot results showing expression level of CyPPO variant proteins in A. thaliana ($T_2$) transfected with mutant gene of CyPPO2, CyPPO4 or CyPPO8. Col-0 means non-transgenic A. thaliana.

FIG. 34 shows a result observed at the 7 day after spraying 5 µM of tiafenacil to the transformed A. thaliana ($T_3$) wherein gene encoding CyPPO2 Y373M variant or CyPPO8 F363M variant is introduced. Col-O means non-transgenic A. thaliana.

FIG. 35 shows a result observed at the 7 day after spraying 5 µM of saflufenacil to transformed A. thaliana ($T_3$) wherein gene encoding CyPPO2 Y373M variant, CyPPO4 Y375M variant or CyPPO8 F363M variant is introduced. Col-O means non-transgenic A. thaliana.

FIG. 36 shows a result observed at the 7 day after spraying 5 µM of Fomesafen to transformed A. thaliana ($T_3$) wherein gene encoding CyPPO2 Y373M variant or CyPPO8 F363M variant is introduced. Col-O means non-transgenic A. thaliana.

FIG. 37 shows a result observed at the 7 day after spraying 25 µM or 5 µM of tiafenacil or 75 µM of saflufenacil to transformed A. thaliana ($T_3$ or $T_2$) wherein gene encoding Y373I, Y373L, Y373V, Y373C, Y373M, V318M+Y373I, V173S+A175C+Y373M, or A175C+V318M+Y373M variant of CyPPO2 is introduced respectively.

FIG. 38 shows a result observed at the 7 day after spraying 25 µM or 10 µM of tiafenacil or 100 µM concentration of saflufenacil to transformed A. thaliana ($T_3$ or $T_2$) wherein gene encoding F363V, F363L, A162L, or A162C+V308M+F363M variant of CyPPO8 is introduced.

FIG. 39 is the map of pCAMBIA3301 vector.

FIG. 40 shows a result observed at the 7 day after spraying PPO-inhibiting herbicide to wild type Dongjin rice and $T_0$ generation of transformants of Dongjin rice transformed with CyPPO2 Y373M mutant gene or CyPP08 F363M mutant gene, wherein A is an image after 853 g ai/ha tiafenacil treatment, and B is an image after 2,087 g ai/ha saflufenacil treatment.

FIG. 41 shows a result observed at the 7 day image after spraying PPO-inhibiting herbicide to CyPPO2 Y373M $T_2$ transformant line no. 3 and CyPPO8 F363M $T_2$ transformant line no. 3 of Dongjin rice, wherein A is an image after 420 g ai/ha tiafenacil treatment, and B is an image after 840 g ai/ha saflufenacil treatment (1: young leaf→4: old leaf). Dongjin means non transgenic rice (cultivar).

FIG. 42 is the western blot result showing expression of CyPPO2 Y373M variant protein in the leaves of CyPPO2 Y373M transformant of Dongjin rice.

FIG. 43 is the western blot result showing expression of CyPPO8 F363M variant protein in the leaves of CyPPO8 F363M transformant of Dongjin rice.

FIG. 44 is the southern blotting result examining whether CyPPO8 F363M is present in CyPPO8 F363M transformant of Dongjin rice.

FIG. 45 is a photograph showing tolerance level against various herbicides of A. thaliana transformants ($T_3$) wherein Y373I of CyPPO2 and F363V of CyPPO8 mutant genes are respectively introduced.

FIG. 46 is a photograph showing herbicide tolerance level of $T_4$ generation of A. thaliana transformants wherein Y373I of CyPPO2 and F363V of CyPPO8 mutant genes are respectively introduced.

FIG. 47 is a photograph showing herbicide tolerance level of $T_5$ generation of CyPPO2 Y373I-introduced transformant and CyPPO8 F363V-introduced transformant of A. thaliana.

FIG. 48 is the western blot result showing PPO protein expression of $T_4$ generation of CyPPO2 Y373I-introduced transformant and CyPPO8 F363V-introduced transformant of A. thaliana.

FIG. 49 is the western blot result showing PPO protein expression of $T_5$ generation of CyPPO2 Y373I-introduced transformant and CyPPO8 F363V-introduced transformant of A. thaliana.

FIG. 50 is a structural diagram exemplarily showing the structure of vector for soybean transformation.

FIG. 51 is the southern blotting result examining whether mutant gene is present in CyPP02 Y373M transformant and CyPPO8 F363M transformant of soybean.

FIG. 52 is a photograph showing herbicide tolerance level of $T_2$ generation of CyPP02 Y373M transformant and CyPPO8 F363M transformant of soybean. Kwangan means non-transgenic soybean (cultivar)

PPO isolated from *Oscillatoria nigro-viridis* PCC 7112 was designated as CyPPO2, PPO isolated from *Lyngbya* sp. PCC 8106 strain was designated as CyPPO4, and PPO isolated from *Halothece* sp. PCC 7418 strain was designated as CyPPO8.

Further, respective nucleotide sequences of CyPPO2, CyPPO4, and CyPPO8 and amino acid sequences encoded by the corresponding sequences were examined, and represented by SEQ ID NOS: 1 to 6.

TABLE 1

| Strain | Primer | Sequence | SEQ ID NO: |
|---|---|---|---|
| *Oscillatoria nigro-viridis* PCC 7112 | CyPPO2_F | CCCCGGATCCATGGAACTTCTTGATACTCT | 12 |
| | CyPPO2_R | CCCCCTCGAGGATTGACCTGGTATCACTCT | 13 |
| *Lyngbya* sp. PCC 8106 | CyPPO4_F | CCCCGGATCCATGACCCATGTTTTGGATTC | 14 |
| | CyPPO4_R | CCCCCTCGAGCTGTCCTAAAAATGATAAAATCTCG | 15 |
| *Halothece* sp. PCC 7418 | CyPPO8_F | CCCCGGATCCATGATAGATACTCTTATAGTGGG | 16 |
| | CyPPO8_R | CCCCCTCGAGTCCTAAGTAATCTAAAACTG | 17 |

FIG. 53 is the western blot result examining whether CyPPO2 Y373M protein and CyPPO8 F363M protein are expressed in the leaves of CyPPO2 Y373M transformant and CyPPO8 F363M transformant of soybean, respectively.

FIG. 54 is a photograph showing growth image before (upper) and after (bottom) treating tiafenacil to CyPPO8 F363M transformant of rapeseed. Youngsan means non-transgenic rapeseed (cultivar).

FIG. 55 is a photograph showing growth image before (upper) and after (bottom) treating saflufenacil to CyPPO8 F363M transformant of rapeseed. Wild type means non-transgenic rapeseed (cultivar).

FIG. 56 shows the western blot result examining whether CyPPO8 F363M protein is expressed in the leaves of CyPPO8 F363M transformant of rapeseed (upper) and showing the Coomassie stain result (bottom).

MODE FOR INVENTION

Hereinafter, the present invention will be described in detail with reference to Examples. However, these Examples are for illustrative purposes only, and the invention is not intended to be limited by these Examples.

Example 1. Isolation of PPO Gene from Prokaryote

*Oscillatoria nigro-viridis* PCC 7112, *Lyngbya* sp. PCC 8106 strain, and *Halothece* sp. PCC 7418 strain were provided by the Institut Pasteur (France), and PPO genes were isolated from each strain. Each PPO gene was synthesized using codon-optimized sequence information for efficient herbicide resistance screening in BT3 *E. coli*. The synthesized PPO genes were amplified using the primers of Table 1.

One microliter (1 µl) of each template (genomic DNA of each strain), 5 µl of 10× buffer, 1 µl of dNTP mixture (each 10 mM), 1 µl of a forward primer (refer to Table 1; 10 µM), 1 µl of a reverse primer (refer to Table 1; 10 µM), 40 µl of DDW, and 1 µl of Pfu-X (Solgent, 2.5 unit/µl) were mixed to prepare 50 µl of PCR reaction mixture, and amplification was performed under conditions of at 94° C. for 4 minutes, and 25 cycles (at 94° C. for 30 seconds, at 56° C. for 30 seconds and at 72° C. for 1.5 minutes), at 72° C. for 5 minutes.

The herbicide tolerance of CyPPO2, CyPPO4, and CyPPO8 prepared above was tested using PPO-deficient *E. coli* (BT3 (ΔPPO)). BT3 (ΔPPO) strain was provided by Hokkaido University (Japan) and it is an *E. coli* strain which is deficient in hemG-type PPO and has Kanamycin tolerance (refer to "Watanabe et al., Dual targeting of spinach protoporphyrinogen oxidase II to mitochondria and chloroplasts by alternative use of two in-frame inhibition codons, JBC 2001 276(23):20474-20481; Che et al., Molecular Characterization and Subcellular Localization of Protoporphyrinogen Oxidase in Spinach Chloroplasts, Plant Physiol. 2000 September; 124(1):59-70").

BT3 (ΔPPO) was transformed with each CyPPO gene, and cultured on the LB (Luria-Bertani) agar media containing PPO-inhibiting herbicide, thereby examining whether the growth of the transformed *E. coli* was inhibited.

The Specific Test Process was as Follows:

CyPPO2, CyPPO4, and CyPPO8 genes prepared above are cloned in pACBB vector (Plasmid #32551; Addgene; refer to FIG. 3). The cloned plasmids were added to BT3 competent cell respectively, thereby transforming by a heat shock method. The transformed *E. coli* with each CyPPO gene was cultured in LB agar media containing chloramphenicol (34 µg/ml, Duchefa).

Single colony of *E. coli* transformed with each CyPPO gene was cultured in 3 ml of LB broth containing chloramphenicol for overnight (220 rpm, 37° C.), and then the each culture was re-cultured with fresh media until absorbance ($OD_{600}$) became 0.5 to 1. It was diluted with LB broth to absorbance ($OD_{600}$) of 0.5. Again, the diluted solution was serially diluted 5 times by a factor of one tenth. Next, 10 µl of each diluted solution was dropped on the LB agar media containing chloramphenicol (34 µg/ml) and 0~400 µM concentration of tiafenacil. The LB agar media were cultured at 37° C. under light condition, and level of growth inhibition was evaluated after 16 to 20 hours.

For comparison, the same test was conducted using BT3 *E. coli* transformant transformed with pACBB-eGFP vector (Plasmid #32551; Addgene; refer to FIG. 3) and BT3 *E. coli* transformant introduced with *A. thaliana*-derived wild type PPO gene (wild type AtPPO1) (SEQ ID NO: 8).

As shown in FIG. 1, the BT3 *E. coli* transformants of CyPPO2, CyPPO4, and CyPPO8 genes exhibited higher herbicide tolerance compared to *E. coli* transformants of AtPPO1 gene at all the concentrations of herbicide tested.

Example 2. Determination of PPO Amino Acid Residues Interacting with PPO-Inhibiting Herbicides from PPO and PPO-Inhibiting Herbicide Complex In order to confirm the binding structure information of PPO protein and herbicide, tiafenacil was used as a representative example of PPO-inhibiting herbicides.

In order to obtain a water-soluble CyPPO2 protein, 7 hydrophobic amino acid residues which were positioned in the thylakoid membrane binding domain in the amino acid of CyPPO2 (SEQ ID NO: 1) were substituted with hydrophilic residues. The gene encoding the amino acid residues-substituted variant protein of CyPPO2 was cloned to pET29b vector (Catalog Number: 69872-3; EMD Biosciences; refer to FIG. 2), and CyPPO2 protein was expressed using *E. coli* system. The expressed CyPPO2 protein was purified through nickel affinity chromatography and was crystallized. CyPPO2 and tiafenacil complex was obtained by soaking of 3 mM tiafenacil, and used for X-ray diffraction by synchrotron radiation accelerator. X-ray diffraction data of the 2.8 Å resolution of CyPPO2-tiafenacil complex crystals was obtained, and the three-dimensional structure was determined, and the binding position of tiafenacil in CyPPO2 protein was analyzed. As a result of structure analysis of CyPPO2 and tiafenacil complex, amino acids of S63, P91, R92, F169, V173, A175, E228, L229, P316, V318, F337, L340, G351, T352, I353 and Y373 positions of CyPPO2 protein (SEQ ID NO: 1) interacted with tiafenacil.

And also, using the information derived from the structure of CyPPO2-tiafenacil complex, amino acid residues which interact with tiafenacil in CyPPO4 (SEQ ID NO: 3) and CyPPO8 (SEQ ID NO: 5) proteins (NCBI BLAST blast.ncbi.nlm.nih.gov/Blast.cgi?PROGRAM=blastp& PAGE_TYPE=BlastSearch&LINK_LOC=blasthome) were determined by sequence homology analysis as below.

The amino acids of CyPPO4 protein (SEQ ID NO: 3) interacting with tiafenacil are N63, S64, S66, P67, P92, R93, F170, S172, G173, V174, Y175, A176, R190, E230, L231, P318, V320, F339, G340, N341, L342, L352, G353, T354, I355, Y375, I424, V458, and R465. The amino acids of CyPPO8 protein (SEQ ID NO: 5) interacting with tiafenacil are P84, R85, F156, V160, A162, Q179, P306, V308, F327, L330, I343, N362, and F363.

Example 3. Verification of PPO-Inhibiting Herbicide Tolerance by PPO Variants (Test in *E. coli*)

In order to enhance PPO-inhibiting herbicide tolerance of CyPPO2, CyPPO4 and CyPPO8, a mutation(s) at the position interacting with herbicide obtained in the Example 2 was introduced, respectively. BT3 (ΔPPO) was transformed with the mutated CyPPO gene, and cultured under the condition treated with PPO-inhibiting herbicide, thereby examining whether growth of transformed BT3 was inhibited. The wild type of each gene was used as a control.

The method of the experiment was as follows:

CyPPO2 and CyPPO4 cloned in pACBB vector (Plasmid #32551; Addgene; refer to FIG. 3) were mutated using primers of Tables 2 to 3, and CyPPO8 cloned in pACBB vector or pET303-CT-His vector (VT0163; Novagen; refer to FIG. 4) were mutated using primers of Table 4.

Fifty microliters of PCR reaction mixture was prepared by mixing 1 μl of template, 5 μl of 10× buffer, 1 μl of dNTP mixture (each 10 mM), 1 μl of a forward primer (10 μM), 1 μl of a reverse primer (10 μM), 40 μl of DDW, and 1 μl of Pfu-X (Solgent, 2.5 unit/μl), and amplification was performed under conditions of at 94° C. for 4 minutes, and 17~25 cycles (at 94° C. for 30 seconds, at 56~65° C. for 30 seconds and at 72° C. for 3 minutes), at 72° C. for 5 minutes. 0.5 μl of DpnI (New England Biolabs) was treated to each 5 μl of PCR product, and incubated at 37° C. for 30 minutes. Reaction solution was transformed with *E. coli* by heat shock method. Each transformant was cultured in LB agar media containing chloramphenicol or ampicillin. Each mutation was confirmed by plasmid DNA sequencing, and each plasmid was transformed to BT3 (ΔPPO).

TABLE 2

Primer for CyPPO2 mutation

| No. | CyPPO2 mutation | Primer (Forward: top; Reverse: bottom) (5'->3') |
|---|---|---|
| 1 | Y373M | GACCTCTATGATTGGTGGAGCTACTGATAG (SEQ ID NO: 18)<br>ACCAATCATAGAGGTCAATGTTTGCCATCC (SEQ ID NO: 19) |
| 2 | Y373V | GACCTCTGTGATTGGTGGAGCTACTGATAG (SEQ ID NO: 20)<br>ACCAATCACAGAGGTCAATGTTTGCCATCC (SEQ ID NO: 21) |
| 3 | Y373I | GACCTCTATCATTGGTGGAGCTACTGATAG (SEQ ID NO: 22)<br>ACCAATGATAGAGGTCAATGTTTGCCATCC (SEQ ID NO: 23) |
| 4 | Y373T | GACCTCTACAATTGGTGGAGCTACTGATAG (SEQ ID NO: 24)<br>ACCAATTGTAGAGGTCAATGTTTGCCATCC (SEQ ID NO: 25) |
| 5 | Y373L | GACCTCTTTGATTGGTGGAGCTACTGATAG (SEQ ID NO:26)<br>ACCAATCAAAGAGGTCAATGTTTGCCATCC (SEQ ID NO: 27) |
| 6 | Y373C | GACCTCTTGTATTGGTGGAGCTACTGATAG (SEQ ID NO: 28)<br>ACCAATACAAGAGGTCAATGTTTGCCATCC (SEQ ID NO: 29) |
| 7 | A175C | GGTGTGTACTGTGGAGATCCTCAACAGCTC (SEQ ID NO: 30)<br>AGGATCTCCACAGTACACACCAGAAACAAA (SEQ ID NO: 31) |
| 8 | A175L | GGTGTGTACTTGGGAGATCCTCAACAGCTC (SEQ ID NO: 32)<br>AGGATCTCCCAAGTACACACCAGAAACAAA (SEQ ID NO: 33) |

TABLE 2-continued Primer for CyPPO2 mutation

| No. | CyPPO2 mutation | Primer (Forward: top; Reverse: bottom) (5'->3') |
|---|---|---|
| 9 | V318M | TATCCAACAATGGCTTCAGTTGTGTTGGCA (SEQ ID NO: 34)<br>AACTGAAGCCATTGTTGGATAAGTGAATGC (SEQ ID NO: 35) |
| 10 | G351A | CGCTGTCTCGCTACGATTTGGACATCGAGT (SEQ ID NO: 36)<br>CCAAATCGTAGCGAGACAGCGAATTCCCTG (SEQ ID NO: 37) |
| 11 | S63T | GCCCGAACACTTTTTCGCCGACGCCGGAATTG (SEQ ID NO: 38)<br>GGCGAAAAAGTGTTCGGGCCCTCCTCCCAG (SEQ ID NO: 39) |
| 12 | R92A | CAAATTGCCTGCTTTTGTGTATTGGGAAAATAAG (SEQ ID NO: 40)<br>ATACACAAAAGCAGGCAATTTGCGATCGGC (SEQ ID NO: 41) |
| 13 | V173S | GTTTCTGGGAGTTATGCCGGCGATCCGCAAC (SEQ ID NO: 42)<br>CCGGCATAACTCCCAGAAACAAAAGGTTCC (SEQ ID NO: 43) |
| 14 | V173C | GTTTCTGGGTGTTATGCCGGCGATCCGCAAC (SEQ ID NO: 44)<br>CCGGCATAACACCCAGAAACAAAAGGTTCCAC (SEQ ID NO: 45) |
| 15 | V173T | GTTTCTGGGACTTATGCCGGCGATCCGCAAC (SEQ ID NO: 46)<br>CCGGCATAAGTCCCAGAAACAAAAGGTTCCAC (SEQ ID NO: 47) |
| 16 | L229F | ACTAAGCCGGGGGAGTTCGGTTCGTTCAAGCAG (SEQ ID NO: 48)<br>CTGCTTGAACGAACCGAACTCCCCCGGCTTAGT (SEQ ID NO: 49) |
| 17 | L340I | TTTTGGAAATATAATTCCGAGGGGCAGGG (SEQ ID NO: 50)<br>CTCGGAATTATATTTCCAAAACCCACTAATTTAC (SEQ ID NO: 51) |
| 18 | I353T | TCGGGACGACTTGGACATCGAGTTTATTTCC (SEQ ID NO: 52)<br>GATGTCCAAGTCGTCCCGAGACAGCGAATTC (SEQ ID NO: 53) |
| 19 | I353L | CTCGGGACGCTTTGGACATCGAGTTTATTT (SEQ ID NO: 54)<br>ATGTCCAAAGCGTCCCGAGACAGCGAATTC (SEQ ID NO: 55) |
| 20 | I353V | ACTAAGCCGGGGGAGTTCGGTTCGTTCAAGCAG (SEQ ID NO: 56)<br>CTGCTTGAACGAACCGAACTCCCCCGGCTTAGT (SEQ ID NO: 57) |
| 21 | I353C | TCGGGACG TGT TGGACATCGAGTTTATTTCC (SEQ ID NO: 58)<br>GATGTCCA ACA CGTCCCGAGACAGCGAATTC (SEQ ID NO: 59) |
| 22 | V318T | TATCCTACGACTGCCTCCGTTGTCTTAGCA (SEQ ID NO: 60)<br>AACGGAGGCAGTCGTAGGATAAGTAAAAGC (SEQ ID NO: 61) |
| 23 | E228A | AAAACTAAGCCGGGGGCGTTGGGTTCGTTCAAG (SEQ ID NO: 62)<br>CTTGAACGAACCCAACGCCCCCGGCTTAGTTTT (SEQ ID NO: 63) |
| 24 | P91L | AAACTTCTTAGATTCGTGTATTGGGAAAAC (SEQ ID NO: 64)<br>ACGAATCTAAGAAGTTTTCTATCTGCGAAT (SEQ ID NO: 65) |
| 25 | P316A + V318L | GCTTTTACTTATGCTACGCTTGCCTCCGTT (SEQ ID NO: 66)<br>GACAACGGAGGCAAGCGTAGCATAAGTAAA (SEQ ID NO: 67) |
| 26 | P316L + V318L | GCTTTTACTTATCTTACGCTTGCCTCCGTT (SEQ ID NO: 68)<br>GACAACGGAGGCAAGCGTAAGATAAGTAAA (SEQ ID NO: 69) |
| 27 | F337V | TTAGTGGGTGTTGGAAATTTAATTCCGAGGGG (SEQ ID NO: 70)<br>TAAATTTCCAACACCCACTAATTTACCCTTGAC (SEQ ID NO: 71) |
| 28 | T352V | TGTCTCGGGGTGATTTGGACATCGAGTTTATTT (SEQ ID NO: 72)<br>GTCCAAATCACCCCGAGACAGCGAATTCCCTG (SEQ ID NO: 73) |
| 29 | V173L | GTTTCTGGGCTTTATGCCGGCGATCCGCAAC (SEQ ID NO: 74)<br>CGGCATAAAGCCCAGAAACAAAAGGTTCCAC (SEQ ID NO: 75) |
| 30 | A175I | GTTTCTGGGGTTTATATTGGCGATCCGCAA (SEQ ID NO: 76)<br>TTGTTGCGGATCGCCAATATAAACCCCAGA (SEQ ID NO: 77) |
| 31 | L340V | TTTTGGAAATGTTATTCCAAGAGGTCAAGGAATC (SEQ ID NO: 78)<br>CTTGAATAACATTTCCAAAACCCACGAGTTT (SEQ ID NO: 79) |
| 32 | L340T | TTTTGGAAATACTATTCCAAGAGGTCAAGG (SEQ ID NO: 80)<br>CTTGAATAGTATTTCCAAAACCCACGAGTTTTC (SEQ ID NO: 81) |
| 33 | F169A | CCAGAAACAGCAGGTTCCACCAACCGCTGCATC (SEQ ID NO: 82)<br>GTGGAACCTGCTGTTTCTGGGGTTTATGCCG (SEQ ID NO: 83) |

TABLE 3

Primer for CyPPO4 mutation

| No. | CyPPO4 mutation | Primer (Forward: top; Reverse: bottom) (5'->3') |
|---|---|---|
| 1 | Y375M | CTTACATCTATGATTGGTGGAGCTACCGAT (SEQ ID NO: 84)<br>CCACCAATCATAGATGTAAGAACCTGCCAT (SEQ ID NO: 85) |
| 2 | Y375V | CTTACATCTGTTATTGGTGGAGCTACCGAT (SEQ ID NO: 86)<br>CCACCAATAACAGATGTAAGAACCTGCCAT (SEQ ID NO: 87) |
| 3 | Y375I | CTTACATCTATCATTGGTGGAGCTACCGAT (SEQ ID NO: 88)<br>CCACCAATGATAGATGTAAGAACCTGCCAT (SEQ ID NO: 89) |
| 4 | Y375T | CTTACATCTACCATTGGTGGAGCTACCGAT (SEQ ID NO: 90)<br>CCACCAATGGTAGATGTAAGAACCTGCCAT (SEQ ID NO: 91) |
| 5 | Y375C | CTTACATCTTGTATTGGTGGAGCTACCGAT (SEQ ID NO: 92)<br>CCACCAATACAAGATGTAAGAACCTGCCAT (SEQ ID NO: 93) |
| 6 | A176C | GGTGTGTATTGTGGAGATCCACAACAGCTT (SEQ ID NO: 94)<br>TGGATCTCCACAATACACACCAGAAACAAA (SEQ ID NO: 95) |
| 7 | A176L | GGTGTGTATTTGGGAGATCCACAACAGCTT (SEQ ID NO: 96)<br>TGGATCTCCCAAATACACACCAGAAACAAA (SEQ ID NO: 97) |
| 8 | P318L + V320L | ATTCCTTATTTGCCATTGGCTTGTGTTGTGCTC (SEQ ID NO: 98)<br>AACACAAGCCAATGGCAAATAAGGAATTTCTGTA (SEQ ID NO: 99) |
| 9 | V320M | TATCCTCCAATGGCTTGTGTTGTGCTCGCA (SEQ ID NO: 100)<br>AACACAAGCCATTGGAGGATAAGGAATTTC (SEQ ID NO: 101) |
| 10 | P318A + V320L | ATTCCTTATGCTCCATTGGCTTGTGTTGTGCTC (SEQ ID NO: 102)<br>AACACAAGCCAATGGAGCATAAGGAATTTCTGTA (SEQ ID NO: 103) |

TABLE 4

Primer for CyPPO8 mutation

| No. | CyPPO8 mutation | Primer (Forward: top; Reverse: bottom) |
|---|---|---|
| 1 | F363M | TTGACAAATATGATTGGTGGAGCTACCGAT (SEQ ID NO: 104)<br>CACCAATCATATTTGTCAAAAGGTGCCATC (SEQ ID NO: 105) |
| 2 | F363V | CTT TTG ACA AAT GTT ATT GGT GGA GCT ACC (SEQ ID NO: 106)<br>AGC TCC ACC AAT AAC ATT TGT CAA AAG GTG (SEQ ID NO: 107) |
| 3 | F363L | CTT TTG ACA AAT CTT ATT GGT GGA GCT ACC (SEQ ID NO: 108)<br>AGC TCC ACC AAT AAG ATT TGT CAA AAG GTG (SEQ ID NO: 109) |
| 4 | F363C | CTT TTG ACA AAT TGT ATT GGT GGA GCT ACC (SEQ ID NO: 110)<br>AGC TCC ACC AAT ACA ATT TGT CAA AAG GTG (SEQ ID NO: 111) |
| 5 | A162C | TCTGGTGTGTAT TGT GGAGATGTTGATCAA (SEQ ID NO: 112)<br>ATCAACATCTCC ACA ATACACACCAGAAAC (SEQ ID NO: 113) |
| 6 | A162L | TCTGGTGTGTAT CTT GGAGATGTTGATCAA (SEQ ID NO: 114)<br>ATCAACATCTCC AAG ATACACACCAGAAAC (SEQ ID NO: 115) |
| 7 | P306L + V308L | ATCTCATAT CTT CCA CTT GCTTGCGTTGTG (SEQ ID NO: 116)<br>AACGCAAGC AAG TGG AAG ATATGAGATTTC (SEQ ID NO: 117) |
| 8 | V308M | TCATATCCTCCA ATG GCTTGCGTTGTGCTC (SEQ ID NO: 118)<br>CACAACGCAAGC CAT TGGAGGATATGAGAT (SEQ ID NO: 119) |
| 9 | P306A + V308L | ATTTCCTATGCCCCCCTAGCTTGTGTGGTCTTAGCC (SEQ ID NO: 120)<br>CACACAAGCTAGGGGGGCATAGGAAATTTCGTTTAAGG (SEQ ID NO: 121) |
| 10 | V160S | GTGTCTGGGTCTTATGCAGGGGATGTGGATC (SEQ ID NO: 122)<br>CCTGCATAAGACCCAGACACAAACGGACTCAC (SEQ ID NO: 123) |
| 11 | I343T | TTGGTACAACTTGGAGTTCAACACTCTTTCC (SEQ ID NO: 124)<br>GAACTCCAAGTTGTACCAAGAGTGCGGATTC (SEQ ID NO: 125) |
| 12 | F363I | CTT TTG ACA AAT ATT ATT GGT GGA GCT ACC (SEQ ID NO: 126)<br>AGC TCC ACC AAT AAT ATT TGT CAA AAG GTG (SEQ ID NO: 127) |

TABLE 4-continued

Primer for CyPPO8 mutation

| No. | CyPPO8 mutation | Primer (Forward: top; Reverse: bottom) |
|---|---|---|
| 13 | F363T | CTT TTG ACA AAT ACT ATT GGT GGA GCT ACC (SEQ ID NO: 128)<br>AGC TCC ACC AAT AGT ATT TGT CAA AAG GTG (SEQ ID NO: 129) |
| 14 | R85A | GGACTTCCCGCTTATGTTTATTGGGAGGGG (SEQ ID NO: 130)<br>CAATAAACATAAGCGGGAAGTCCGCGATCAGC (SEQ ID NO: 131) |
| 15 | I343V | CTTGGTACAGTTTGGAGTTCAACACTCTTTC (SEQ ID NO: 132)<br>AACTCCAAACTGTACCAAGAGTGCGGATTC (SEQ ID NO: 133) |
| 16 | P84L | AGGTTTACTTAGGTATGTTTACTGGGAGGG (SEQ ID NO: 134)<br>CATACCTAAGTAAACCTCTATCTGAAAGA (SEQ ID NO: 135) |
| 17 | R85C | GACTTCCCTGTTATGTTTATTGGGAGGGGAAAC (SEQ ID NO: 136)<br>TAAACATAACAGGGAAGTCCGCGATCAGCAAAG (SEQ ID NO: 137) |
| 18 | R85H | ACTTCCCCATTATGTTTATTGGGAGGGGAAAC (SEQ ID NO: 138)<br>CAATAAACATAATGGGGAAGTCCGCGATCAGC (SEQ ID NO: 139) |
| 19 | R85L | ACTTCCCCTTTATGTTTATTGGGAGGGGAAAC (SEQ ID NO: 140)<br>CAATAAACATAAAGGGGAAGTCCGCGATCAGC (SEQ ID NO: 141) |
| 20 | R85T | GACTTCCCACTTATGTTTATTGGGAGGGGAAAC (SEQ ID NO: 142)<br>ATAAACATAAGTGGGAAGTCCGCGATCAGCAAAG (SEQ ID NO: 143) |
| 21 | R85V | GACTTCCCGTTTATGTTTATTGGGAGGGGAAAC (SEQ ID NO: 144)<br>ATAAACATAAACGGGAAGTCCGCGATCAGCAAAG (SEQ ID NO: 145) |
| 22 | F156A | GTGAGTCCGGCTGTGTCTGGGGTTTATGCA (SEQ ID NO: 146)<br>CCCAGACACAGCCGGACTCACTAACCGTTG (SEQ ID NO: 147) |
| 23 | V160C | CCGTTTGTGTCTGGGTGCTATGCAGGGGATGTG (SEQ ID NO: 148)<br>CACATCCCCTGCATAGCACCCAGACACAAACGG (SEQ ID NO: 149) |
| 24 | Q179G | TCCGCCAGTCCGGTAACTCGTCCAAATGCAG (SEQ ID NO: 150)<br>CGAGTTACCGGACTGGCGGATGTGGGCGGTG (SEQ ID NO: 151) |
| 25 | F327V | GTTTTCCCCTCAAAGGAGTGGGTAATCTTAACCCTC (SEQ ID NO: 152)<br>GAGGGTTAAGATTACCCACTCCTTTGAGGGGAAAAC (SEQ ID NO: 153) |
| 26 | L330T | TTTGGTAATACTAACCCTCGCAGTCAAGGA (SEQ ID NO: 154)<br>GCGAGGGTTAGTATTACCAAATCCTTTGAG (SEQ ID NO: 155) |
| 27 | F363M + N362S | CTTTTGACATCAATGATTGGTGGAGCTACC (SEQ ID NO: 156)<br>CCAATCATTGATGTCAAAAGGTGCCATCCT (SEQ ID NO: 157) |

Single colony of E. coli transformed with each CyPPO gene was cultured in 3 ml of LB broth containing chloramphenicol for overnight (220 rpm, 37° C.), and then the each culture was re-cultured with fresh media until absorbance ($OD_{600}$) became 0.5 to 1. It was diluted with LB broth to absorbance ($OD_{600}$) of 0.5. Again, the diluted solution was serially diluted 5 times by a factor of one tenth. Next, 10 μl of each diluted solution was dropped on the LB agar media containing chloramphenicol (34 μg/ml) and 0~400 μM concentration of tiafenacil. The LB agar media were cultured at 37° C. under light condition, and level of growth inhibition was evaluated after 16 to 20 hours.

Herbicides used in the test were listed in Table 5:

TABLE 5

| Family | Herbicide |
|---|---|
| Pyrimidinedione-based herbicide | Tiafenacil |
|  | Saflufenacil |
| Diphenyl ether-based herbicide | Fomesafen |
|  | Acifluorfen |
| N-phenylphthalimides-based herbicide | Flumioxazin |
| Triazolinones-based herbicide | Sulfentrazone |

TABLE 5-continued

| Family | Herbicide |
|---|---|
| Oxazolidinediones-based herbicide | Pentoxazone |
| Phenylpyrazoles-based herbicide | Pyraflufen-ethyl |
| Others | Pyraclonil |

The results were shown in Tables 6 to 8 and FIGS. 5 to 25.

TABLE 6

Herbicide tolerance level conferred by CyPPO2 mutation

| CyPPO2 | Tiafenacil | Saflufenacil | Flumioxazin |
|---|---|---|---|
| CyPPO2 (wild type) | − | − | − |
| Y373M + G351A | +++++ | +++++ | +++++ |
| Y373C | ++++ | +++++ | +++++ |
| Y373I | ++++ | +++++ | +++++ |
| Y373L | ++++ | +++++ | +++++ |
| Y373M | ++++ | +++++ | +++++ |
| Y373T | ++++ | +++++ | +++++ |
| Y373V | +++ | +++++ | +++++ |
| A175C | +++ | ++++ | +++++ |
| A175L | ++ | +++++ | ++++ |

TABLE 6-continued

Herbicide tolerance level conferred by CyPPO2 mutation

| CyPPO2 | Tiafenacil | Saflufenacil | Flumioxazin |
|---|---|---|---|
| V318M | ++ | ++++ | +++++ |
| P316A + V318L | + | NT | NT |
| P316L + V318L | + | NT | NT |
| F337V + Y373M | ++ | NT | NT |
| T352V + Y373M | ++++ | NT | NT |
| G351A + T352V + Y373M | +++ | NT | NT |
| P91L + Y373M | ++ | NT | NT |

(NT: Not Tested)

TABLE 7

Herbicide tolerance level conferred by CyPPO4 mutation

| CyPPO4 | Tiafenacil | Saflufenacil | Flumioxazin |
|---|---|---|---|
| CyPPO4 | − | − | − |
| Y375M | +++++ | +++++ | +++++ |
| Y375V | +++++ | +++++ | +++++ |
| Y375I | +++++ | +++++ | +++++ |
| Y375T | +++++ | +++ | +++++ |
| Y375C | +++++ | +++ | NT |
| A176C | +++++ | +++++ | +++++ |
| A176L | +++++ | ++++ | +++++ |
| P318L + V320L | +++++ | ++++ | NT |
| V320M | +++++ | ++++ | NT |
| P318A + V320L | +++++ | ++++ | NT |

(NT: Not Tested)

TABLE 8

Herbicide tolerance level conferred by CyPPO8 mutation

| CyPPO8 | Tiafenacil | Saflufenacil | Fomesafen | Acifluorfen | Flumioxazin | Sulfentrazone | Pentoxazone | Pyraflufen-ethyl | Pyraclonil |
|---|---|---|---|---|---|---|---|---|---|
| CyPPO8 | − | − | − | − | − | − | − | − | − |
| F363C | ++++ | ++++ | ++++ | +++++ | +++ | ++++ | +++++ | +++++ | +++++ |
| F363L | +++ | +++ | + | +++ | ++ | ++ | +++++ | ++++ | ++++ |
| F363M | +++ | +++ | + | +++ | ++ | ++ | +++++ | ++++ | ++++ |
| F363V | +++ | +++ | − | ++ | +++ | ++ | +++++ | ++++ | +++++ |
| A162L | ++ | ++ | +++ | ++++ | ++++ | ++++ | ++++ | ++++ | +++ |
| V308M | ++ | ++ | +++ | +++++ | +++ | ++++ | ++++ | ++++ | ++++ |
| P306A + V308L | + | + | + | ++++ | NT | ++ | +++ | +++ | + |
| P306L + V308L | + | + | ++ | +++++ | NT | ++++ | +++ | ++++ | + |
| A162C | NT | NT | NT | ++ | NT | + | +++ | ++++ | + |
| P84L + F363M | +++ | NT | NT | NT | NT | NT | NT | NT | NT |
| N362S + F363M | +++ | NT | NT | NT | NT | NT | NT | NT | NT |

(NT: Not Tested)

The Tables 6 to 8 show the results of evaluating the herbicide tolerance of wild type and PPO variants. The level of herbicide tolerance of the wild type was represented by "−", and the level of herbicide tolerance was graduated by representing the equal level of tolerance by "−", and if higher, adding "+" to the max "+++++".

FIGS. 5 to 25 show the results of E. coli transformed with the CyPPO genes (wild type and variants), and the concentration of herbicide treatment is described on the top. The most left column is the result of E. coli culture solution OD$_{600}$=0.5, and the next five columns were diluted 5 times by a factor of one tenth.

As shown in Table 6 and FIGS. 5 to 13, CyPPO2 wild type transformant (hereinafter, represented by 'Cy2 WT'; control) showed rapid growth inhibition from 25 μM or 50 μM of pyrimidinedione-based herbicide tiafenacil treatment, but growth inhibition of transformant wherein mutant genes of Y373C, Y373I, Y373L, Y373M, Y373T, Y373V, A175C, A175L, V318M, G351A+Y373M, P316A+V318L, P316L+V318L, Y373M+F337V, Y373M+T352V, Y373M+G351A+T352V, and Y373M+P91L were introduced respectively was not observed even at the maximum concentration (200 μM) (FIG. 5). When another pyrimidinedione-based herbicide saflufenacil was treated, Cy2 WT also showed growth inhibition at 100 μM or the higher concentration, but the transformant wherein mutant genes of Y373C, Y373I, Y373L, Y373M, Y373T, Y373V, A175C, A175L, V318M, and G351A+Y373M were introduced respectively was not observed even at the maximum concentration (200 μM) (FIG. 6). When N-phenylphthalimides-based herbicide flumioxazin was treated, the growth inhibition of Cy2 WT was started from 25 μM of concentration of herbicide treatment, but the growth inhibition of the transformant wherein mutant genes of Y373C, Y373I, Y373L, Y373M, Y373T, Y373V, A175C, A175L, V318M, and G351A+Y373M were introduced respectively was not observed at the maximum concentration (200 μM) (FIG. 7).

As shown in Table 7 and FIGS. 14 to 16, when tiafenacil was treated, CyPPO4 wild type gene was introduced (hereinafter, represented by 'Cy4 WT'; control) showed growth inhibition from 100 μM of the herbicide treated, but the growth inhibition of transformant wherein mutant genes of A176L, A176C, P318L+V320L, P318A+V320L, V320M, Y375I, Y375T, Y375V, Y375M, and Y375C were introduced respectively was not observed at the maximum concentration (200 μM) (FIG. 14). When saflufenacil was treated, Cy4 WT showed growth inhibition from 100 μM of the herbicide treatment, but the growth inhibition of transformant wherein mutant genes of Y375C, Y375I, Y375M, Y375T, Y373V, A176C, A176L, P318L+V320L, P318A+V320L, and V320M were introduced respectively was not observed at the maximum concentration (200 μM) (FIG. 15). When flumioxazin was treated, the growth inhibition of Cy4 WT was observed from 200 μM of concentration of herbicide treatment, but the growth inhibition of the transformant wherein mutant genes of Y375I, Y375M, Y375T, Y373V, A176C, and A176L were introduced respectively was not observed (FIG. 16).

As shown in Table 8 and FIGS. 17 to 25, when tiafenacil or saflufenacil was treated, CyPPO8 wild type gene was introduced (hereinafter, represented by 'Cy8 WT'; control) showed no growth from 5 μM of herbicide treatment concentration, the growth of the transformant wherein mutant genes of F363C, F363L, F363M, F363V, A162L, V308M, P306A+V308L, P306L+V308L, F363M+P84L, and F363M+N362S were introduced respectively was observed even at the minimum concentration of 25 μM or higher (FIGS. 17 and 18). When diphenyl-ether-based herbicide fomesafen was treated, Cy8 WT showed no growth from 25 μM of herbicide treatment concentration, but the growth of the transformant wherein mutant genes of F363C, F363L, F363M, A162L, V308M, P306A+V308L, and P306L+V308L were introduced respectively was observed at the concentration of 25 μM or higher (FIG. 19). When another diphenyl-ether-based herbicide acifluorfen was treated, Cy8 WT showed no growth from 50 μM of herbicide treatment concentration, but the growth of the transformant wherein mutant genes of F363C, F363L, F363M, F363V, A162C, A162L, V308M, P306A+V308L, and P306L+V308L were introduced respectively was observed at the concentration of 50 μM or higher (FIG. 20). When flumioxazin was treated, Cy8 WT showed no growth from 5 μM of herbicide treatment concentration, but the growth of the transformant wherein mutant genes of F363C, F363L, F363M, F363V, A162L, and V308M were introduced respectively was observed at the concentration of 25 μM or higher (FIG. 21). When triazolinones-based herbicide sulfentrazone was treated, Cy8 WT showed growth only by 25 μM of herbicide treatment concentration, but the growth of the transformant wherein mutant genes of F363C, F363L, F363M, F363V, A162C, A162L, V308M, P306A+V308L, and P306L+V308L were introduced respectively was observed at the concentration of 50 μM or higher (FIG. 22). When pentoxazone or pyraflufen-ethyl was treated, Cy8 WT showed no growth from 5 μM of herbicide treatment concentration, but the growth of the transformant wherein mutant genes of F363C, F363L, F363M, F363V, A162C, A162L, V308M, P306A+V308L, and P306L+V308L were introduced respectively was observed at the maximum concentration (200 μM) (FIGS. 23 and 24). When pyraclonil was treated, Cy8 WT showed no growth from 25 μM of herbicide treatment concentration, but the growth of the transformant wherein mutant genes of F363C, F363L, F363M, F363V, A162C, A162L, V308M, P306A+V308L, P306L+V308L were introduced respectively was observed at the maximum concentration (200 μM) (FIG. 25).

Example 4: Measurement of Enzyme Activity and IC$_{50}$ Value by Herbicides of PPO Wild Type and Variants The enzyme activity of variants wherein amino acids of certain position of PPO protein were mutated to increase herbicide tolerance was examined and inhibition assay for the PPO-inhibiting herbicides was conducted. It was confirmed that the PPO protein had low water-solubility, but when the PPO protein was fused with MBP (maltose binding protein) (MBP-PPO), it was water-soluble and stably expressed. Therefore, the wild type and variant proteins which were expressed in the form of fusion protein with MBP were used in the present experiments (refer to FIG. 26).

In order to clone wild type genes and variant genes of CyPPO2, CyPP04, and CyPPO8 (refer to Example 1 and Example 2), those genes were introduced into pMAL-c2X vector (refer to FIG. 27) respectively, and then expressed in BL21-CondonPlus (DE3) E. coli (CodonPlus).

The transformed E. coli were cultured under the following conditions to express introduced PPO genes:
Induction: OD$_{600}$=0.2, addition of IPTG to 0.3 mM final concentration;
Expression temperature: 23° C., 200 rpm shaking culture;
Expression time: 16 hrs;
Culture scale: 200 ml/1,000 ml flask.

Cell lysis and protein extraction were performed by the following process to the cultured cells:
Extraction buffer: Column buffer (50 mM Tris-Cl, pH 8.0, 200 mM NaCl) 5 ml buffer/g cell;
Sonication: SONICS&MATERIALS VCX130 (130 watts);
15 sec ON, 10 sec OFF for 5 min on ice;
Centrifugation under the condition of 4° C. for 20 minutes (20,000×g); and the supernatant obtained by the centrifugation was diluted at the ratio of 1:6 using column buffer.

The following process for purification of PPO protein was performed in a 4° C. cold room. Amylose resin (New England Biolabs) was packed to 1.5×15 cm column (Bio-Rad Econo Columns 1.5×10 cm, glass chromatography column, max. vol), and the obtained protein extracts were loaded to the column at the a flow rate of 0.2 ml/min. The column was washed with 3 column volumes of buffer and the amount of protein in the washing solution was checked. When the protein was no longer detected, the washing was terminated. Then, the MBP-PPO protein was eluted with approximately 2 column volumes of buffer containing 20 mM maltose. The protein concentration of each eluent was determined and the elution was stopped when the protein was no longer detected. Ten microliter of each fraction was investigated for protein quantification and SDS-PAGE analysis. The highly pure fractions of PPO protein variants (for example, CyPPO2-Y373M, CyPPO4-Y375M, CyPPO8-F363M) were taken for the enzyme assay.

The SDS-PAGE analysis of each PPO was shown in FIGS. 28 to 30. Referring to the result shown in FIG. 28, CyPPO2 wild type protein (elution 7, lane 2) and CyPPO2-Y373M (elution 5, lane 7) were taken and used for analysis of enzyme activity.

Referring to the result shown in FIG. 29, as to CyPPO4 wild type protein (elution 3, lane 2) and CyPPO4-Y375M (elution 3, lane 6) were taken and used for analysis of enzyme activity.

Referring to the result shown in FIG. 30, CyPPO8 wild type protein (elution 9, lane 3) and CyPPO8-F363M (elution 4, lane 6) were taken and used for analysis of enzyme activity.

The enzyme activity of the purified wild type protein and variant proteins of CyPPO2, CyPPO4 and CyPPO8 was measured by the following process.

Overall process was performed in dark under nitrogen stream. Since protoporphyrinogen IX, a substrate of PPO protein was not commercially available, it was chemically synthesized in the laboratory. Six micrograms of protoporphyrin IX was dissolved in 20 ml of 20% (v/v) EtOH, and stirred under dark condition for 30 minutes. The obtained protoporphyrin IX solution was put into a 15 ml screw tube in an amount of 800 μl, and flushed with nitrogen gas for 5 minutes. To this, 1 g of sodium amalgam was added and vigorously shaken for 2 minutes. The lid was opened to exhaust hydrogen gas in the tube. Thereafter, the lid was closed and incubated for 3 minutes. The protoporphyrinogen IX solution was filtered using syringe and cellulose membrane filter. To 600 μl of the obtained protoporphyrinogen IX solution, approximately 300 μl of 2M MOPS [3-(N-morpholino)propanesulfonic acid] was added to adjust pH to 8.0. To determine the enzyme activity of PPO protein, a reaction mixture was prepared with the following composition (based on 10 ml): 50 mM Tris-Cl (pH 8.0); 50 mM NaCl; 0.04% (v/v) Tween 20; 40 mM glucose (0.072 g); 5 units glucose oxidase (16.6 mg); and 10 units catalase (1 μl).

Two hundred microliters of a reaction mixture containing a purified PPO protein was placed in 96 well plates and preincubated for 30 min at room temperature to reduce the oxygen concentration by the coupled reaction of glucose oxidase-catalase. The mineral oil was layered and then the reaction was initiated by adding the substrate, protoporphyrinogen IX solution to a final concentration of 50 μM. The reaction proceeded at room temperature for 30 min and the fluorescence of protoporphyrin IX was measured using Microplate reader (Sense, Hidex) (excitation: 405 nm; emission: 633 nm). To calculate the PPO enzyme activity, the protoporphyrinogen IX solution was kept open in the air to oxidize the solution (overnight). To this, 2.7 N HCl was added, and the absorbance at 408 nm was measured. A standard curve was generated using standard protoporphyrin IX, and PPO activity was measured by calibration of protoporphyrin IX using the standard curve of protoporphyrin IX.

The enzyme activity of the obtained PPO wild type and variants was shown in Tables 10 and 11.

Michaelis-Menten constant (Km) and the maximal velocity (Vmax) values of each enzyme were calculated in order to evaluate the kinetic study of CyPPO2 and CyPPO8. The initial reaction velocity was measured where the reaction velocity was proportional to concentration by varying the substrate concentration. The amount of produced protoporphyrin IX which is an enzyme reaction product was measured by time course at room temperature for 20 minutes. Km and Vmax values were calculated with the enzyme kinetics analysis program by Michaelis-Menten equation. The wild type AtPPO1 was used as a control. The result was shown in Table 9:

TABLE 9

Determination of Km and Vmax of CyPPO2 and CyPPO8

|  | CyPPO2 | CyPPO8 | AtPPO1 |
|---|---|---|---|
| Km (μM) | 9.1 ± 0.5 | 7.7 ± 0.2 | 9.6 ± 1.8 |
| Vmax (μM mg protein−1 min−1) | 285 ± 15 | 305 ± 10 | 135 ± 19 |

From the results, Km values of CyPPO2 and CyPPO8 were lower than that of AtPPO1, confirming that the affinity between enzyme and substrate was better, while Vmax values of CyPPO2 and CyPPO8 were more than two times higher than that of AtPPO1. In conclusion, PPO proteins of CyPPO2 and CyPPO8 show better ability as PPO enzyme than the plant-derived AtPPO1.

In addition, the concentration of the PPO-inhibiting herbicides that inhibits the PPO enzyme activity of each PPO wild type and variants by 50% ($IC_{50}$) was measured for each herbicide. The final concentrations of each herbicide were as follows:

Tiafenacil, saflufenacil, fomesafen, butafenacil, flumioxazin and sulfentrazone: 0, 10, 50, 100, 250, 500, 1,000, 2,500, 5,000 nM The $IC_{50}$ value was calculated as the concentration of the herbicide inhibiting the PPO enzyme activity to 50% before adding the herbicide at the above concentration.

The $IC_{50}$ values of different herbicides were shown in the following Tables 10 and 11.

TABLE 10

| No. | Mutation site | Activity (%) | $IC_{50}$ (nM) Tiafenacil | Saflufenacil | Fomesafen | Butafenacil | Flumioxazin | Sulfentrazone |
|---|---|---|---|---|---|---|---|---|
| CyPPO2 | | | | | | | | |
|  | WT | 100 | 25 | 50 | 182 | 13 | 122 | NT |
| 1 | Y373M | 90 | 250 | 5,000 | 395 | 63 | 136 | NT |
| 2 | Y373I | 75 | 639 | 5,000 | 70 | 1516 | 464 | NT |
| 3 | Y373L | 44 | 300 | NT | NT | NT | NT | NT |
| 4 | Y373V | 35 | 525 | NT | NT | NT | NT | NT |
| 5 | Y373C | 39 | 225 | NT | NT | NT | NT | NT |
| 6 | Y373T | 10 | 2500 | NT | NT | NT | NT | NT |
| 7 | A175L | 41 | 230 | NT | NT | NT | NT | NT |
| 8 | S63T + Y373M | 90 | 246 | NT | NT | NT | NT | NT |
| 9 | R92A + Y373M | 50 | 219 | NT | NT | NT | 310 | NT |
| 10 | V173S + Y373M | 80 | 430 | NT | NT | NT | NT | NT |
| 11 | V173S + Y373I | 25 | 610 | NT | NT | NT | NT | NT |
| 12 | V173S + Y373L | 40 | 530 | NT | NT | NT | NT | NT |
| 13 | V173S + Y373V | 10 | 1,000 | NT | NT | NT | NT | NT |
| 14 | V173C + Y373M | 53 | 680 | NT | NT | NT | NT | NT |
| 15 | V173C + Y373I | 28 | 915 | NT | NT | NT | NT | NT |
| 16 | V173T + Y373M | 15 | 543 | NT | NT | NT | NT | NT |
| 17 | V173T + Y373I | 25 | 1,500 | NT | NT | NT | NT | NT |
| 18 | V173L + Y373M | 83 | 290 | NT | NT | NT | NT | NT |

TABLE 10-continued

| No. | Mutation site | Activity (%) | IC$_{50}$ (nM) | | | | | |
|---|---|---|---|---|---|---|---|---|
| | | | Tiafenacil | Saflufenacil | Fomesafen | Butafenacil | Flumioxazin | Sulfentrazone |
| 19 | A175L + Y373M | 62 | 4,500 | 5,000 | 1,720 | 4,000 | 5,000 | 5,000 |
| 20 | A175L + Y373I | 15 | 2,000 | 5,000 | NT | NT | NT | NT |
| 21 | A175C + Y373M | 83 | 3,700 | 5,000 | 770 | 2,500 | 372 | 5,000 |
| 22 | A175C + Y373I | 31 | 2,000 | NT | NT | NT | NT | NT |
| 23 | A175I + Y373M | 52 | 2,500 | NT | NT | NT | NT | NT |
| 24 | E228A + Y373M | 85 | 214 | NT | NT | NT | NT | NT |
| 25 | L229F + Y373T | 10 | 1,800 | NT | NT | NT | NT | NT |
| 26 | V318M + Y373M | 73 | 456 | 5,000 | 523 | 708 | 210 | 3776 |
| 27 | V318M + Y373I | 50 | 2,765 | 5,000 | 145 | 1,232 | 1,021 | 5,000 |
| 28 | V318M + Y373V | 42 | 2,140 | 5,000 | NT | NT | NT | NT |
| 29 | V318T + Y373I | 25 | 1,500 | NT | NT | NT | NT | NT |
| 30 | L340I + Y373M | 80 | 259 | NT | NT | NT | NT | NT |
| 31 | L340I + Y373I | 85 | 584 | NT | NT | NT | NT | NT |
| 32 | L340V + Y373M | 80 | 257 | NT | NT | NT | NT | NT |
| 33 | G351A + Y373M | 23 | 706 | 5,000 | 300 | 36 | NT | NT |
| 34 | I353T + Y373M | 32 | 1,152 | NT | NT | NT | NT | NT |
| 35 | I353T + Y373I | 20 | 1,300 | NT | NT | NT | NT | NT |
| 36 | I353T + Y373L | 10 | 3,000 | NT | NT | NT | NT | NT |
| 37 | I353L + Y373M | 80 | 271 | NT | NT | NT | NT | NT |
| 38 | I353V + Y373M | 63 | 445 | NT | NT | NT | NT | NT |
| 39 | I353C + Y373M | 12 | 550 | NT | NT | NT | NT | NT |
| 40 | S63T + V173S + Y373M | 60 | 430 | NT | NT | NT | NT | NT |
| 41 | S63T + V173S + Y373I | 60 | 427 | NT | NT | NT | NT | NT |
| 42 | S63T + I353T + Y373M | 15 | 278 | NT | NT | NT | NT | NT |
| 43 | S63T + I353T + Y373I | 5 | 1200 | NT | NT | NT | NT | NT |
| 44 | V173S + V318M + Y373M | 5 | 3,000 | NT | NT | NT | NT | NT |
| 45 | V173T + L340I + Y373M | 50 | 518 | NT | NT | NT | NT | NT |
| 46 | V173S + A175C + Y373M | 38 | 5,000 | 5,000 | 758 | 2,591 | 5,000 | 5,000 |
| 47 | A175C + V318M + Y373M | 47 | 3,793 | 5,000 | 2,033 | 1,475 | 419 | 5,000 |
| 48 | A175L + V318M + Y373M | 40 | 3,100 | NT | NT | NT | NT | NT |
| 49 | A175C + I353L + Y373M | 5 | 1,900 | NT | NT | NT | NT | NT |
| 50 | A175C + I353V + Y373M | 69 | 2,310 | NT | NT | NT | NT | NT |

TABLE 10-continued

|  | Mutation site | Activity (%) | IC₅₀ (nM) | | | | | |
|---|---|---|---|---|---|---|---|---|
| No. | | | Tiafenacil | Saflufenacil | Fomesafen | Butafenacil | Flumioxazin | Sulfentrazone |
| 51 | R92A | 66 | 125 | NT | NT | NT | NT | NT |
| 52 | F169A | 72 | 57 | NT | NT | NT | NT | NT |
| 53 | V173C | 68 | 79 | NT | NT | NT | NT | NT |
| 54 | A175C | 86 | 100 | NT | NT | NT | NT | NT |
| 55 | A175L | 68 | 325 | NT | NT | NT | NT | NT |
| 56 | V318M | 76 | 140 | NT | NT | NT | NT | NT |
| 57 | F337V | 20 | 148 | NT | NT | NT | NT | NT |
| 58 | L340T | 18 | 56 | NT | NT | NT | NT | NT |
| 59 | I353T | 40 | 162 | NT | NT | NT | NT | NT |
| CyPPO4 | | | | | | | | |
| | WT | 100 | 22 | 33 | 28 | 10 | NT | NT |
| 1 | Y375M | 95 | 124 | 5,000 | 133 | 39 | NT | NT |

(NT: not tested)

TABLE 11

| CyPPO8 No. | Mutation site | Activity (%) | IC₅₀ (nM) | | | | | |
|---|---|---|---|---|---|---|---|---|
| | | | Tiafenacil | Saflufenacil | Fomesafen | Butafenacil | Flumioxazin | Sulfentrazone |
| | WT | 100 | 4 | 11 | 13 | 2.8 | NT | NT |
| 1 | F363M | 100 | 183 | 5,000 | 163 | 30 | 266 | NT |
| 2 | F363C | 17 | 36 | 500 | 38 | 53 | NT | NT |
| 3 | F363V | 15 | 2,000 | 5,000 | 1,500 | 250 | 2,500 | NT |
| 4 | F363L | 54 | 322 | NT | NT | NT | NT | NT |
| 5 | F363I | 62 | 698 | 5,000 | 133 | NT | 1100 | NT |
| 6 | F363T | 5 | 3,000 | 5,000 | 1,500 | NT | 2,500 | NT |
| 7 | R85A + F363M | 62 | 700 | NT | NT | NT | NT | NT |
| 8 | R85A + F363I | 40 | 2,350 | NT | NT | NT | NT | NT |
| 9 | A162L + F363M | 17 | 5,000 | NT | NT | NT | 5,000 | NT |
| 10 | A162C + F363M | 87 | 2,500 | 5,000 | NT | NT | 1,166 | NT |
| 11 | V160S + F363M | 58 | 500 | NT | NT | NT | NT | NT |
| 12 | V160S + F363I | 26 | 2,280 | NT | NT | NT | NT | NT |
| 13 | V308M + F363M | 81 | 1,017 | 5,000 | NT | NT | 210 | NT |
| 14 | V308M + F363I | 29 | 1,810 | NT | NT | NT | NT | NT |
| 15 | I343T + F363M | 10 | 2,100 | NT | NT | NT | NT | NT |
| 16 | I343V + F363M | 44 | 288 | NT | NT | NT | NT | NT |
| 17 | R85A + V308M + F363M | 39 | 2,347 | 5,000 | NT | NT | NT | NT |
| 18 | V160S + V308M + F363I | 5 | 4,000 | NT | NT | NT | NT | NT |
| 19 | A162C + F363I | 29 | 2,450 | NT | NT | NT | NT | NT |
| 20 | A162C + F363L | 6 | 5,000 | NT | NT | NT | NT | NT |
| 21 | R85A + A162L + F363M | 11 | 5,000 | NT | NT | NT | NT | NT |
| 22 | R85A + A162L + F363I | 15 | 1,061 | NT | NT | NT | NT | NT |
| 23 | R85A + A162C + F363M | 19 | 5,000 | 5,000 | 5,000 | 4,310 | 2,700 | 5,000 |
| 24 | R85A + A162C + F363I | 16 | 5,000 | NT | NT | NT | NT | NT |
| 25 | A162C + V308M + F363M | 45 | 3,580 | 5,000 | 420 | 2500 | 697 | 5,000 |

TABLE 11-continued

| CyPPO8 No. | Mutation site | Activity (%) | IC$_{50}$ (nM) | | | | | |
|---|---|---|---|---|---|---|---|---|
| | | | Tiafenacil | Saflufenacil | Fomesafen | Butafenacil | Flumioxazin | Sulfentrazone |
| 26 | A162C + V308L + F363M | 53 | 2,041 | NT | NT | NT | NT | NT |
| 27 | R85C + F363M | 28 | 2,500 | NT | NT | NT | NT | NT |
| 28 | R85H + F363M | 30 | 622 | NT | NT | NT | NT | NT |
| 29 | R85L + F363M | 19 | 892 | NT | NT | NT | NT | NT |
| 30 | R85T + F363M | 24 | 1,356 | NT | NT | NT | NT | NT |
| 31 | R85V + F363M | 18 | 875 | NT | NT | NT | NT | NT |
| 32 | A162L + Q179G + F363M | 39 | 5,000 | 5,000 | 630 | 4,000 | 5,000 | 5,000 |
| 33 | R85A | 98 | 80 | NT | NT | NT | NT | NT |
| 34 | F156A | 85 | 28 | NT | NT | NT | NT | NT |
| 35 | V160C | 80 | 44 | NT | NT | NT | NT | NT |
| 36 | A162C | 76 | 75 | NT | NT | NT | NT | NT |
| 37 | A162L | 82 | 219 | NT | NT | NT | NT | NT |
| 38 | V308M | 93 | 76 | NT | NT | NT | NT | NT |
| 39 | F327V | 22 | 81 | NT | NT | NT | NT | NT |
| 40 | L330T | 27 | 69 | NT | NT | NT | NT | NT |
| 41 | I343T | 18 | 365 | NT | NT | NT | NT | NT |

(NT: not tested)

As shown in the Tables 10 and 11, it was demonstrated that in case of variants of CyPPO proteins, the IC$_{50}$ values of each herbicide were significantly increased compared to the wild type. Such results show that herbicide tolerance was increased by amino acid mutation at certain positions of PPO protein. Although the present data showed that CyPPO protein variants have reduced enzyme activity compared to the wild type, it might be caused by the different conditions of the protein folding, and/or hydrophobicity of recombinants PPOs compared to the native PPOs. While the native PPOs are hydrophobic and localize to the membranes of chloroplasts in plants, the recombinant PPOs produced in *E. coli* are hydrophilic containing a MBP as a fusion partner. Thus, when PPO variants are properly assembled and expressed to chloroplasts in plants, the enzyme activity would not be affected drastically.

Example 5. Generation of *A. thaliana* Transformants Using CyPPO Variants and PPO-Inhibiting Herbicide Tolerance Test 5-1. Construction of *A. thaliana* Transformant Vectors and Generation of *A. thaliana* Transformants

*A. thaliana* was transformed with a binary vector having ORF of a selectable marker, Bar gene (glufosinate-tolerant gene) and ORF of each amino acid mutation gene of CyPPO2, CyPPO4 or CyPPO8. The transgenic plant was examined for cross-tolerance towards glufosinate and PPO-inhibiting herbicides. The bar gene was also used to examine whether the transgene was stably inherited during generations. NOS promoter and E9 terminator were used for bar gene expression.

In order to express CyPPO2 variants, CyPPO4 variants, and CyPPO8 variants, respectively in a plant, a CaMV35S promoter and NOS terminator were used. In addition, in order to transit protein to chloroplast, transit peptide (TP) of AtPPO1 gene (SEQ ID NO: 8) was inserted in front of 5' of the inserted gene using XbaI and XhoI restriction enzymes. Further, for identification of the expressed protein, hemagglutinin (HA) tag was fused to the 3'-terminal region using BamHI and SacI restriction enzymes. The transit peptide region inserted into the vector was represented by SEQ ID NO: 10, and the inserted HA tag sequence was represented by SEQ ID NO: 11. Encoding genes of CyPPO2 variants, CyPPO4 variants, or CyPPO8 variants were inserted between the transit peptide and HA tag using XhoI and BamHI restriction enzymes. NOS terminator was inserted after HA tag, thereby terminating transcription of PPO gene. A schematic diagram of the plant transformation binary vector is shown in FIG. 31.

Each constructed vector was transformed to *Agrobacterium tumefaciens* GV3101 competent cell by a freeze-thaw method. To prepare *Agrobacterium* GV3101 competent cell, *Agrobacterium* GV3101 strain was cultured in 5 ml LB media under the condition of 30° C. and 200 rpm for 12 hrs. The culture solution was poured to 200 ml LB media, and then cultured under the condition of 30° C. and 200 rpm for 3~4 hrs, and centrifuged at 4° C. for 20 minutes. The cell pellet was washed with sterile distilled water, and then resuspended in 20 ml LB media. Snap frozen 200 ul aliquots with liquid nitrogen were stored in a deep freezer.

Each transformed *Agrobacterium* was cultured in an antibiotic media (LB agar containing spectinomycin) and screened. The screened colony was liquid cultured in LB broth. After *Agrobacterium* cell was harvested from the culture solution, it was resuspended in a 5% (w/v) sucrose, 0.05% (v/v) Silwet L-77 solution (Momentive performance materials company) at an absorbance (OD$_{600}$) of 0.8. By floral dipping method, *A. thaliana* wild type (Col-0 ecotype) was transformed, and then the seed (To) was harvested 1~2 months later.

Bar gene in the binary vector was used for screening of individual transformants. The obtained T$_0$ seeds were sown in ½ MS media (2.25 g/L MS salt, 10 g/L sucrose, 7 g/L Agar) supplemented with 25 µM glufosinate, and the surviving plants were selected after 7 days of sowing, and transplanted into soil and grown, to obtain $T_1$ plants.

In order to examine PPO-inhibiting herbicide tolerance of the transgenic plants, 4-week-old plants were evenly sprayed with 100 ml of 1 uM Tiafenacil solution (0.05% Silwet L-77) per 40×60 cm area (0.24 m²). While wild type *A. thaliana* (Col-0 ecotype) completely died within 7 days after treatment, each transformant showed no damage to PPO-inhibiting herbicide treatment.

The $T_2$ seeds were sown to ½ MS media (2.25 g/L MS salt, 10 g/L sucrose, 7 g/L Agar) supplemented with 25 μM glufosinate, and after 1 week, surviving plants were transplanted into soil.

The *A. thaliana* wild type PPO1 (wild type AtPPO1) was used as a negative control having PPO-inhibiting herbicides sensitivity (GenBank accession no. AX084732 (the nucleotide sequence of the gene was represented by SEQ ID NO: 8, and the amino acid sequence was represented by SEQ ID NO: 7)). Mutant AtPPO1 with amino acid substitutions of Y426M (the 426$^{th}$ amino acid, tyrosine was substituted with methionine) and S305L (the 305$^{th}$ amino acid, serine was substituted with leucine) in the amino acid sequence of the wild type AtPPO1 was used as a positive control (the amino acid sequence was represented by SEQ ID NO: 9) (Li et al. Development of protoporphyrinogen oxidase as an efficient selection marker for *Agrobacterium tumefaciens*-mediated transformation of maize. Plant physiol. 2003 133:736-747).

The CyPPO variants used in generation of *A. thaliana* transformants were listed in Table 12:

TABLE 12

| CyPPO2 mutation | Line No. | CyPPO4 mutation | Line No. | CyPPO8 mutation | Line No. |
|---|---|---|---|---|---|
| Y373M | 32 | Y375M | 14 | F363M | 22 |
|  | 34 |  | 31 |  | 51 |
|  | 38 |  |  |  | 52 |
|  | 39 |  |  | F363V | 1 |
|  | 40 |  |  |  | 18 |
| Y373V | 34 |  |  | F363L | 1 |
| Y373I | 23 |  |  |  | 33 |
|  | 34 |  |  | A162L | 1 |
| Y373L | 23 |  |  |  | 5 |
|  | 43 |  |  | A162C + V308M + F363M | 46 |
| Y373C | 40 |  |  |  | 48 |
| V318M + Y373I | 1 |  |  |  |  |
|  | 3 |  |  |  |  |
| V173S + A175C + Y373M | 3 |  |  |  |  |
|  | 4 |  |  |  |  |
|  | 51 |  |  |  |  |
|  | 72 |  |  |  |  |
|  | 84 |  |  |  |  |
| A175C + V318M + Y373M | 4 |  |  |  |  |
|  | 8 |  |  |  |  |

5-2. Seed Germination

Tiafenacil tolerance of *A. thaliana* was confirmed using $T_2$ seeds which survived under 1 μM tiafenacil spray at $T_1$ generation. The transformants were introduced Y373M mutant of CyPPO2, Y375M mutant of CyPPO4, or F363M mutant of CyPPO8 (CyPPO2 Y373M transformant, CyPPO4 Y375M transformant, and CyPPO8 F363M transformant, respectively). Glufosinate tolerance of the transformant was confirmed by sowing *A. thaliana* seeds in a medium supplemented with glufosinate (50 μM PPT).

The result was shown in FIG. 32.

No. 32, No. 34, and No. 28 of CyPPO2 Y373M transformants germinated, No. 14 and No. 31 of CyPPO4 Y375M transformants, and No. 22. No. 51 and No. 52 of CyPPO8 F363M transformants germinated even in ½ MS media containing 1 μM or higher concentration of tiafenacil. In addition, the wild type *A. thaliana* (Col-0) seeds used as a negative control did not germinate in ½ MS media containing 70 nM tiafenacil, and mutant AtPPO1 transformants (AtPPO1 SLYM) used as a positive control germinated even in ½ MS media containing 1 μM tiafenacil.

5-3. Confirmation of Segregation Ratio of Tolerance Trait in $T_2$ Generation Seeds In order to determine inheritance, segregation ratios were investigated with $T_2$ seeds. The results were shown in Tables 13 to 15.

TABLE 13

CyPPO2 transformants ($T_2$)

| Mutation | Line No. | Segregation ratio |
|---|---|---|
| Y373M | 32 | 2.53:1 |
|  | 34 | 3.21:1 |
|  | 38 | 3.18:1 |
|  | 39 | 3.17:1 |
| Y373V | 34 | 3.13:1 |
| Y373I | 23 | 2.70:1 |
|  | 34 | 3.55:1 |
| Y373L | 5 | 2.7:1 |
|  | 23 | 2.96:1 |
|  | 43 | 3.3:1 |
| Y373C | 40 | 3.32:1 |
| V318M + Y373I | 1 | 2.95:1 |
|  | 3 | 2.95:1 |
| V173S + A175C + Y373M | 3 | 3.27:1 |
|  | 4 | 2.5:1 |
|  | 72 | 3.08:1 |
|  | 84 | 2.95:1 |
|  | 51 | 3.32:1 |
| A175C + V318M + Y373M | 4 | 2.8:1 |
|  | 8 | 2.57:1 |

TABLE 14

CyPPO4 transformants ($T_2$)

| Mutation | Line No. | Segregation ratio |
|---|---|---|
| Y375M | 14 | 2.53:1 |
|  | 31 | 3:1 |

TABLE 15

CyPPO8 transformants ($T_2$)

| Mutation | Line No. | Segregation ratio |
|---|---|---|
| F363M | 22 | 3.08:1 |
|  | 51 | 3.54:1 |
|  | 52 | 3.04:1 |
| F363V | 1 | 2.52:1 |
|  | 18 | 2.57:1 |
| F363L | 1 | 2.54:1 |
|  | 33 | 2.77:1 |
| A162L | 1 | 2.5:1 |
|  | 5 | 3.5:1 |
| A162C + V308M + F363M | 46 | 2.6:1 |
|  | 48 | 2.59:1 |

As shown in Table 13, in case of the CyPPO2 mutant gene inserted transformant, No. 32, No. 34, No. 38, and No. 39 lines of Y373M variant, No. 34 line of Y373V variant, No. 23, and No. 34 lines of Y373I variant, No. 23, and No. 43 lines of Y373L variant, No. 40 line of Y373C variant, No. 1 and No. 3 lines of V318M+Y373I variant, No. 3, No. 4, No. 72, No. 84, and No. 51 lines of V173S+A175C+Y373M variant, and No. 4 and No. 8 lines of A175C+V318M+Y373M variant exhibited approximately 3:1 of tolerance versus susceptible individuals, and thereby it was demonstrated that single copy of transgenes were integrated to *A. thaliana* genome according to Mendel's law.

As shown in Table 14, in case of the CyPPO4 mutant gene inserted transformant, No. 14 and No. 31 lines of Y375M variant exhibited approximately 3:1 of tolerance versus susceptible individuals, and thereby it was demonstrated that single copy of transgenes were integrated to *A. thaliana* genome.

As shown in Table 15, in case of the CyPPO8 mutant gene inserted transformant, No. 22, No. 51 and No. 52 lines of F363M variant, No. 1 and No. 18 lines of F363V variant, No. 1 and No. 33 lines of F363L variant, No. 1 and No. 5 lines of A162L variant, and No. 46 and No. 48 lines of A162C+V308M+F363M exhibited approximately 3:1 of tolerance versus susceptible individuals, and thereby it was demonstrated that single copy of transgenes integrated to the *A. thaliana* genome.

5-4. Investigation of CyPPO Protein Expression in Herbicide-Tolerant *A. thaliana* ($T_2$)

The expression of CyPPO2 Y373M, CyPPO4 Y375M or CyPPO8 F363M in protein level was examined the expression of introduced genes. After approximately 100 mg of *A. thaliana* $T_2$ transformant leaves were pulverized together with liquid nitrogen, the protein was extracted by adding protein extraction buffer (0.05 M Tris-Cl pH 7.5, 0.1 M NaCl, 0.01 M EDTA, 1% Triton X-100, 1 mM DTT). Western blotting was conducted using the extracted protein. After electrophoresis, the proteins were transferred to PVDF (polyvinylidene difluoride) membrane, and then western blotting was conducted using anti-HA antibody (Santacruz) and anti-actin antibody (loading control, comparison of the amount of experimental protein; Abcam).

The result was shown in FIG. 33.

The level of mutant PPO protein expression was similar in CyPPO2 Y373M transformant and CyPPO8 F363M transformant, whereas CyPPO4 Y375M exhibited low level of expression of PPO variant.

The transformant lines were further progressed by one generation ($T_3$ generation), and it confirmed that each line of transformants had tolerance to herbicides (refer to the Example 5-5). This indicates that expression of introduced genes is maintained as progressing the generation and they conferred herbicide tolerance.

5-5. Verification of Herbicide Tolerance of Transformed *A. thaliana*

In order to demonstrate the herbicide tolerance of amino acid variant encoding genes of CyPPO2, CyPPO4 and CyPPO8 in a plant, herbicide tolerance was tested to $T_2$ generation or $T_3$ generation. All spray tests was performed just before bolting, approximately 4 weeks after transplanting. One hundred milliliters of herbicides with solution (0.05% Silwet L-77) per 40×60 cm area (0.24 $m^2$) were sprayed.

The result observed at the 7th day after spraying to CyPPO2 Y373M variant, CyPPO4 Y375M variant, and CyPPO8 F363M variant were shown in FIG. 34 (the result of tiafenacil treatment), FIG. 35 (the result of saflufenacil treatment), and FIG. 36 (the result of fomesafen treatment). The wild type Col-0 (negative control) died, while AtPPO1 SLYM (positive control) and the experimental groups, No. 38, No. 39 and No. 34 lines of CyPPO2 Y373M transformant, and No. 22, No. 51 and No. 52 lines of CyPPO8 F363M transformant exhibited continuous growth all in tiafenacil 5 μM, saflufenacil 5 μM and fomesafen 5 μM. No. 14 line of CyPPO4 Y375M transformant exhibited continuous growth in saflufenacil 5 μM and fomesafen 5 μM.

Tiafenacil 25 μM or saflufenacil 75 μM was treated to $T_3$ transformants of Y373C, Y373I, Y373L, Y373M and Y373V mutant genes of CyPPO2. And tiafenacil 25 μM or saflufenacil 100 μM was sprayed to $T_3$ transformant of F360L, F360V and A162L mutant genes of CyPPO8.

Tiafenacil 5 μM was sprayed to $T_2$ transformant of V318M+Y373I, V173S+A175C+Y373M and A175C+V318M+Y373M mutant genes of CyPPO2. Tiafenacil 10 μM was sprayed to $T_2$ generation of the transformant of A162C+V308M+F363M mutant gene of CyPPO8.

The result of observed at the 7th day after spraying was shown in Table 16 (Injury index) and FIG. 37 (CyPPO2 variant; $T_3$ generation (upper, bottom)/$T_2$ generation (middle)) and FIG. 38 (CyPPO8 variant; $T_3$ generation (upper, middle)/$T_2$ generation (bottom)).

TABLE 16

| | | Injury index | |
|---|---|---|---|
| | Line No. | Tiafenacil | Saflufenacil |
| | Concentration | 5 μM | 5 μM |
| Col-0 (wild type) | | 5 | 5 |
| CyPPO2 | | 5 | NT |
| CyPPO2 variants ($T_3$) | | 25 μM | 75 μM |
| Y373M | 40-4 | 2.5 | NT |
| Y373C | 40-3 | 2 | 1.5 |
| Y373I | 23-2 | 0 | 1 |
| | 34-2 | 0 | 0.75 |
| Y373L | 23-9 | 1.5 | 1.6 |
| | 43-1 | 1.5 | 3 |
| Y373V | 34-10 | 2 | 2 |
| CyPPO2 variants($T_2$) | | 5 μM | 75 μM |
| V318M + Y373I | 1 | 0 | NT |
| | 3 | 0 | NT |
| V173S + A175C + Y373M | 3 | 1.5 | NT |
| | 4 | 2 | NT |
| | 51 | 2 | NT |
| | 72 | 2 | NT |
| | 84 | 3 | NT |
| A175C + V318M + Y373M | 4 | 0 | NT |
| | 8 | 3 | NT |
| CyPPO8 | | 5 | 5 |
| CyPPO8 variants ($T_3$) | | 5 μM | 75 μM |
| F363M | 22 | 0 | NT |
| | 51 | 0 | NT |
| | 52 | 0 | NT |
| | | 25 μM | 100 μM |
| F363L | 33-7 | 1.5 | 2.5 |
| | 1-3 | 2.5 | 1.5 |
| F363V | 1-7 | 0.5 | 0 |
| | 18-1 | 0.5 | 0 |
| A162L | 1-6 | 3.4 | 4 |
| | 5-4 | 3.4 | 3.8 |
| | 5-7 | 3.9 | 3.8 |
| CyPPO8 variants($T_2$) | | 10 μM | 100 μM |
| A162C + V308M + F363M | 46 | 1 | NT |
| | 48 | 1 | NT |
| CyPPO4 variants | | 5 μM | 5 μM |
| Y375M | 14 | 4 | 2 |

NT: Not tested

Injury index of the Table 16 was evaluated by the criteria of the following Table 17 (this was equally applied to injury index provided in the context):

TABLE 17

| Injury index | Symptom |
|---|---|
| 0 | No damage |
| 1 | Dried leaf end |
| 2 | Over 20% and less than 30% of the plant was scorched |

TABLE 17-continued

| Injury index | Symptom |
|---|---|
| 2.5 | Over 30% and less than 50% of the plant was scorched |
| 3 | Over 50% and less than 70% of the plant was scorched |
| 4 | Over 70% of the plant was scorched |
| 5 | The whole plant was dried and died |

As shown in Table 16 and FIG. 37, all transformants of CyPPO2 variants respectively grew continuously in not only 5 μM but also 25 μM of tiafenacil.

As shown in Table 16 and FIG. 38, transformants of each CyPPO8 variant grew continuously in not only 10 μM but also 25 μM of tiafenacil, and grew continuously in saflufenacil 100 μM.

In addition, the tolerance level of transformants ($T_3$) in which CyPPO2 Y373I and CyPPO8 F363V were introduced respectively was confirmed in each 50 μM of herbicides (flumioxazin, sulfentrazone, tiafenacil or saflufenacil). AtPPO1 SLYM was used as the tolerance control group (positive control). Tiafenacil, saflufenacil, flumioxazin, or sulfentrazone were treated at a concentration of 50 μM respectively, and after 7 days, injury index was evaluated. The result was shown in FIG. 45 and Table 18. For reference, the molecular weight (MW) of tiafenacil is 511.87, and the molecular weight of saflufenacil is 500.85, and the molecular weight of flumioxazin is 354.34, and the molecular weight of sulfentrazone is 387.18. Each herbicide at a concentration of 50 μM was evenly sprayed with 100 ml on a 40×60 cm area (0.24 m$^2$). The converted treatment dosages correspond to 106.7 g ai/ha of tiafenacil, 104.4 g ai/ha of saflufenacil, 73.8 g ai/ha of flumioxazin, and 80.7 g ai/ha of sulfentrazone, respectively.

TABLE 18

| | Injury Index | | |
|---|---|---|---|
| | AtPPO1 SLYM | CyPPO8 F363V | CyPPO2 Y373I |
| Tiafenacil | 4 | 2 | 2 |
| Saflufenacil | 0-1 | 0-1 | 0-1 |
| Flumioxazin | 4-5 | 2 | 3 |
| Sulfentrazone | 0-1 | 0-1 | 0-1 |

As shown in FIG. 45 and Table 18, tolerance of mutant gene transformants were similar or higher compared to AtPPO1 SLYM which was known for herbicide tolerance.

While wild type *A. thaliana* died after 0.8 μM tiafenacil treatment, the PPO mutant transformants exhibited continuous growth in 5 μM, 10 μM, or 25 μM tiafenacil treatment.

From this result, the CyPPO variants are expected to give various PPO-inhibition herbicide tolerances to other plants as well as *A. thaliana*.

5-6. Confirmation of Transgene Stability During Generation Passage

This test is to confirm that genes introduced in *A. thaliana* were stably inherited and expressed even if generation progresses.

The CyPPO2 Y373I mutant and CyPPO8 F363V mutant transformants were developed to $T_4$, or $T_5$ generation as follow; $T_3$ lines 23-2, 23-7, 34-2 of CyPPO2 Y373I and 1-7, 18-1, 18-7 of CyPPO8 F363V. The herbicide tolerance was maintained through $T_3$ to $T_5$ generation of each line indicating the stability of transgene during generations.

Figure 46:
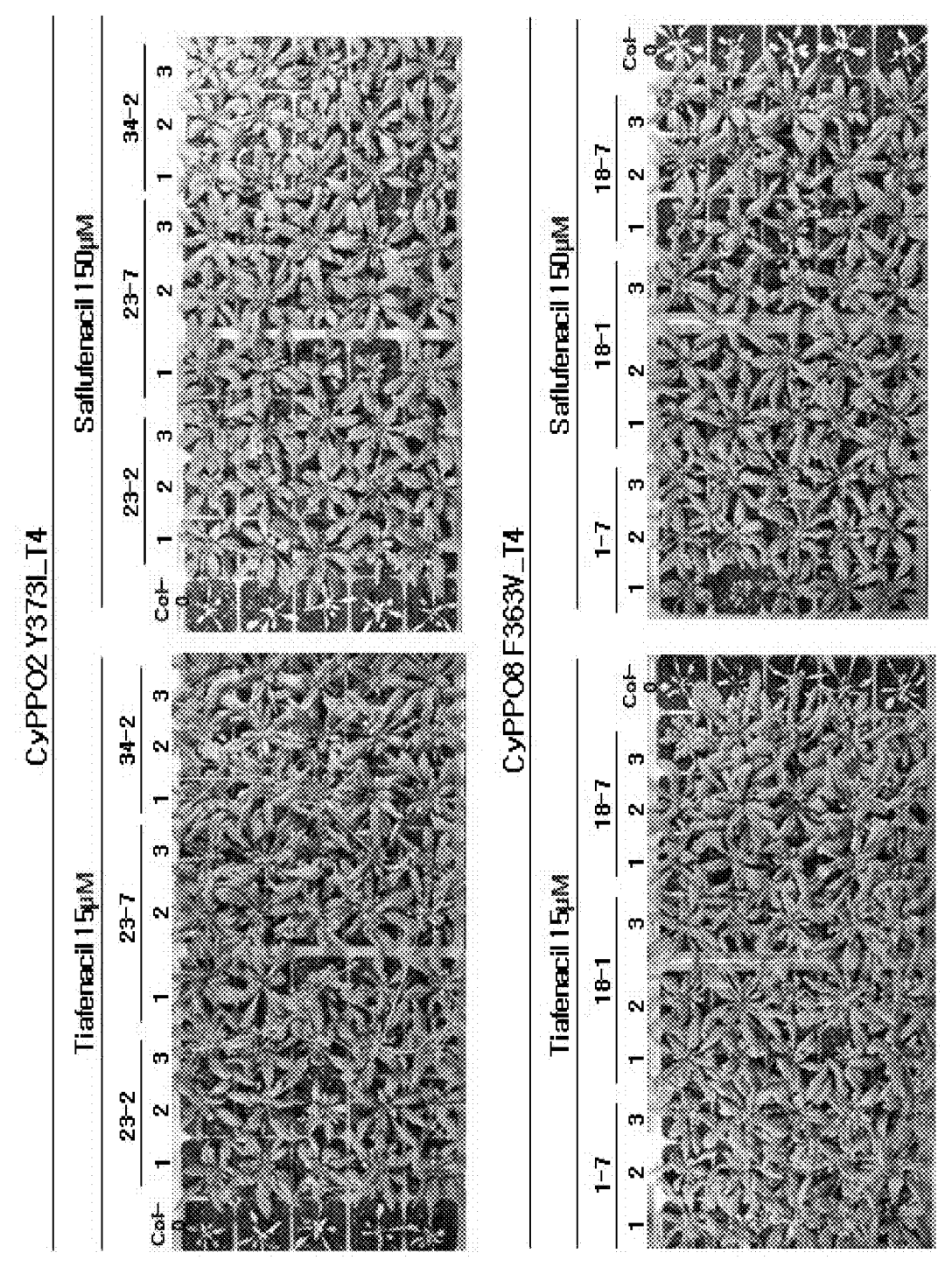

Specifically, 15 μM tiafenacil or 150 μM saflufenacil was treated to $T_4$ or $T_5$ lines, and 7 days after herbicide treatment, damage level was evaluated. The result was shown in FIG. 46 ($T_4$ line) and FIG. 47 ($T_5$ line).

In addition, western blotting was conducted to confirm protein expression. The proteins were extracted from transformants. After grinding seedling using liquid nitrogen, protein extraction buffer (0.05 M Tris-Cl pH 7.5, 0.1 M NaCl, 0.01 M EDTA, 1% Triton X-100, 1 mM DTT) was added and the total protein was extracted. The extracted protein was transferred to PVDF membrane after electrophoresis, western blotting was conducted using anti-HA antibody (Santacruz). The expressed proteins in the transformant were detected. The result was shown in FIG. 48 ($T_4$ line) and FIG. 49 ($T_5$ line).

As shown in FIG. 46 to FIG. 49, herbicide tolerance of all the generations of $T_4$ and $T_5$ was maintained, and PPO protein expression was also confirmed. Specifically, while Col-0 (negative control) completely died when 15 μM tiafenacil or 150 μM saflufenacil was treated, $T_4$ and $T_5$ transformants were maintained without injury (Injury index 0). For reference, when 25 μM tiafenacil or 75 μM saflufenacil was treated in $T_3$ generation, the level of injury index was 0~1.

Example 6. Generation of Rice Transformants Using CyPPO Variants and PPO-Inhibiting Herbicide Tolerance Test 6-1. Construction of Rice Transformation Vector and Generation of Rice Transformants A binary vector having ORF of Bar gene (glufosinate-tolerant gene) and ORF of each amino acid mutant gene of CyPPO2 or CyPPO8 was constructed and used for rice transformation. Each gene were cloned in pCAMBIA3301 vector (refer to FIG. 39). The CaMV 35S promoter for expression of Bar gene and the 35S terminator for transcription termination were used.

In order to express mutant genes of CyPPO2 or CyPPO8 in a plant, the ubiquitin promoter of a corn and the NOS terminator were used. In addition, the transit peptide (TP) of AtPPO1 was fused in the N-terminal region of CyPPO2 or CyPPO8 mutant. Each vector constructed was transformed to *Agrobacterium tumefaciens* LBA4404 competent cell (Takara) by an electric shock method.

The transformed *Agrobacterium* was used to transform Dongjin rice (wild type cultivar). After removing seed husk of Dongjin rice, disinfecting, and dark culturing in N6D media at 32° C. for 5 days, rice seeds were mixed with the transformed *Agrobacterium* solution, and then transplanted on 2N6-AS100 media. It was incubated at 28° C. for 1 day in dark, and then incubated at 23.5° C. for 4 days in dark. Seeds were incubated on N6D cf500 ppt4 media supplemented with appropriate concentration of phosphinothricin (Duchefa) at 28° C. for 10 days under light, and transformed callus was selected among infected seeds. The selected callus was moved on REIII cf500 ppt4 media supplemented with appropriate concentration of phosphinothricin (Duchefa), thereby inducing a plant.

The composition of the used media was listed in Table 19:

TABLE 19

| Media name | Ingredient | Usage |
|---|---|---|
| N6D | N6 powder | 4 g |
| | Sucrose | 30 g |
| | L-Proline | 2.878 g |
| | Casamino acid | 0.3 g |
| | Myo-Inositol | 0.1 g |
| | 2,4-Dichlorophenoxy (dissolve in ethanol) | 2 mg |
| | Phytagel | 4 g |
| | Distilled Water up to | 1 L |
| | | (pH 5.8) |

TABLE 19-continued

| Media name | Ingredient | Usage |
|---|---|---|
| 2N6-AS100 | N6 powder | 4 g |
| | Sucrose | 30 g |
| | D-glucose (Monohydrate) | 10 g |
| | Casamino acid | 0.3 g |
| | 2,4-Dichlorophenoxy (dissolve in ethanol) | 2 mg |
| | Phytagel | 4 g |
| | Acetosyringone (20 mg/ml, dissolve in DMSO) | 1 ml |
| | Distilled Water up to | 1 L (pH 5.2) |
| N6D cf500 ppt4 | N6 powder | 4 g |
| | Sucrose | 30 g |
| | L-proline | 2.878 g |
| | Casamino acid | 0.3 g |
| | Myo-inositol | 0.1 g |
| | 2,4-Dichlorophenoxy (2 mg/ml in ethanol) | 1 ml |
| | Phytagel | 4 g |
| | Cefotaxime sodium | 500 mg |
| | Distilled Water up to | 1 L (pH 5.8) |
| REIII cf500 ppt4 | MS vitamin powder | 4.41 g |
| | Sucrose | 30 g |
| | Sorbitol | 30 g |
| | Casamino acid | 2 g |
| | NAA (1 mg/ml) | 20 µl |
| | Kinetin | 2 mg |
| | Myo-inositol | 0.1 g |
| | Phytagel | 4 g |
| | Cefotaxime sodium | 500 mg |
| | Distilled Water up to | 1 L (pH 5.8) |

6-2. Verification of PPO-Inhibiting Herbicide Tolerance of Transformed Rice

In order to examine the level of herbicide tolerance of transformants of CyPPO2 and CyPPO8 mutant genes in a monocotyledon crop, herbicide tolerance was tested in $T_0$ generation plant of Dongjin rice in which each gene was transformed.

After taking tillers of 5-week-old rice of $T_0$ generation of CyPPO2 Y373M transformant and CyPPO8 F363M transformant, they were allowed to grow, and tiafenacil or saflufenacil were treated, respectively. Two hundreds milliliters of 200 µM tiafenacil (corresponding to 853 g ai/ha) or 500 µM saflufenacil (corresponding to 2,085 g ai/ha) was treated in the area of 40×60 cm. For reference, the recommended treatment dosage of tiafenacil for weed control is approximately 150 g ai/ha, and the recommended treatment dosage of saflufenacil for weed control is under 145 g ai/ha.

$T_2$ transformants of CyPPO2 Y373M and CyPPO8 F363M were used for herbicide treatment at $47^{th}$ day after sowing. One hundred milliliters of 200 µM tiafenacil (corresponding to 420 g ai/ha) and 400 µM saflufenacil (corresponding to 840 g ai/ha) were sprayed respectively in the area of 40×60 cm. The result observed at the $7^{th}$ day after spraying was shown in FIG. 40 (the result showing $T_0$ generation plants of CyPPO2 Y373M transformant line No. 1 and No. 3 and CyPPO8 F363M transformant line No. 2 and No. 3 after tiafenacil or saflufenacil treatment) and FIG. 41 (showing $T_2$ generation plants of CyPPO2 Y373M transformant line #3 and CyPPO8 F363M transformant line #3 after tiafenacil or saflufenacil treatment), respectively. "non-GM" in FIG. 40 indicates non-transformed wild type Dongjin rice, and was used as a negative control.

As shown in FIG. 40 and FIG. 41, severe damages were in the negative control, wild type Dongjin rice, after treatment of tiafenacil or saflufenacil, but no or weak damage was observed in $T_0$ generation plants of CyPPO2 Y373M transformant (represented by "CyPPO2YM") line No. 1 and No. 3 and $T_2$ generation plants of CyPPO2 Y373M transformant #3-1. No damage was observed in $T_0$ generation plants of CyPPO8 F363M transformant (represented by "CyPPO8FM") line #1 and #3 and $T_2$ generation plants of CyPPO8 F363M transformant #3-1 compared to the wild type Dongjin rice after treatment of tiafenacil or saflufenacil.

All CyPPO2 Y373M transformant and CyPPO8 F363M transformant rice plants exhibited tolerance after the treatment of tiafenacil or saflufenacil of higher concentration than the recommended concentration for weed control. This indicated that the genes introduced to rice plants were inherited and expressed stably, showing PPO-inhibiting herbicide tolerance through generations.

6-3. Verification of Protein Expression in Rice Transformants

In order to confirm that mutant protein (CyPPO2 Y373M or CyPPO8 F363M) was expressed in CyPPO2 Y373M transformant and CyPPO8 F363M transformant, the protein was extracted in a leaf from each transformant line, and western blotting was conducted.

For this, 5 ml/g tissue of extraction buffer (50 mM Tris-Cl, pH 7.5, 150 mM NaCl, 1 mM EDTA, 0.5% NP-40) and protease inhibitor (Xpert Protease Inhibitor Cocktail Solution, GenDepot) were added to ground leaf tissue of each transformant. The extracted protein was loaded to SDS-PAGE gel, and transferred to PVDF membrane. The membrane was incubated with CyPPO2 or CyPPO8 peptide-specific primary antibody (GenScript) at the ratio of 1:1000. Protein was detected by HRP-conjugated secondary antibody using ECL reagent and Luminograph (Atto).

The obtained images were shown in FIG. 42 (CyPPO2 Y373M expression) and FIG. 43 (CyPPO8 F363M). CyPPO protein was detected in CyPPO2 Y373M transformant line #1 and #3 and CyPPO8 F363M transformant line #2 and #3.

6-4. Copy Number Analysis of Introduced Genes in Transformed Rice

The genomic DNA was extracted from leaf tissues of CyPPO8 F363M transformant to analyze the copy number of the transgene.

Genomic DNA was extracted as follows. After grinding leaf tissue of the transformed rice using a pestle and a mortar in liquid nitrogen, 5 ml/g tissue of DNA isolation buffer (2% (w/v) CTAB, 1.5 M NaCl, 25 mM EDTA, 0.2% (v/v) beta-mercaptoethanol, 100 mM Tris-Cl (pH 8.0)) was added and vortexed. After heating at 60° C. for over 1 hour, 1 volume of chloroform:isoamyl alcohol (24:1) was added and mixed with inverting. After centrifugation at the condition of 7000×g for 10 minutes at 4° C., supernatant was moved to a new tube, and 2.5 volume of ethanol was mixed. After centrifugation at 5000×g for 5 minutes at 4° C., supernatant was discarded and the pellet was dissolved in TE buffer (LPSS). After adding 20 µg/ml RNase A (Bioneer), it was incubated at 37° C. for 30 minutes. After adding 1 volume of phenol:chloroform (1:1), it was mixed and centrifuged at 10,000×g for 10 minutes at 4° C. Supernatant was moved to a new tube, and then 1 volume of chloroform:isoamyl alcohol (24:1) was added and mixed. After centrifugation at 10,000×g for 10 minutes for 4° C., supernatant was moved to a new tube, and 0.1 volume of NaOAc (pH 5.2) and 2 volume of ethanol were added and mixed. Then, it was centrifuged at 5,000×g for 5 minutes at 4° C., and the pellet was washed with 70% ethanol. After air dry, genomic DNA was dissolved in an appropriate amount of TE buffer.

The 10~40 µg of extracted DNA was digested for overnight using EcoRI (Enzynomics).

Then, after 0.8% (w/v) Agarose gel electrophoresis (50 V), gel was treated as follows:
1) depurination: 0.25 N HCl, 15 minutes shaking
2) denaturation: 0.5 M NaOH, 1.5 M NaCl, 30 minutes shaking
3) neutralization: 0.5 M Tris (pH 7.5), 1.5 M NaCl, 20 minutes shaking Thereafter, DNA fragments were moved to nitrocellulose membrane (GE healthcare) using a capillary transfer method, cross linking was performed using UV Crosslinker (UVC-508; ULTRA LUM Inc.).

Hybridization was performed by the following method: The nitrocellulose membrane was dipped in Easyhybridization solution (Roche), and incubated at 42° C. for 3 hrs. Then, the solution was discarded, substituted with a new DIG Easyhybridization solution, and incubated for overnight at 42° C.

The probe (DIG-labeled CyPPO8-M probe) was labelled by PCR reaction as follows:

| Materials | |
|---|---|
| Template (CyPPO8 plasmid DNA) | 0.5 µl |
| 10X buffer | 3 µl |
| DIG-dNTP | 2 µl |
| forward primer (10 µM) | 3 µl |
| reverse primer (10 µM) | 3 µl |
| DDW | 18 µl |
| e-Taq polymerase (Solgent Inc.) | 0.5 µl |
| total | 30 µl |

TABLE 20

| Conditions for PCR reaction | | |
|---|---|---|
| 94° C. | 3 min | |
| 94° C. | 30 sec | 35 cycles |
| 58° C. | 30 sec | |
| 72° C. | 1 min | |
| 72° C. | 5 min | |

Sequences for Primers

```
Forward primer for CyPPO8 F363M probe:
                               (SEQ ID NO: 158)
GCGTTAACGGGTGCATTAGGC Reverse primer for CyPPO8 F363M probe:
                               (SEQ ID NO: 159)
TGGAAAGAGTGTTGAACTCC
```

After PCR product was electrophoresed in agarose gel, the labelled probe band was extracted.

After hybridization with labelled probe, membrane was washed in low stringency washing buffer (2×SSC, 0.1% SDS) followed by high stringency washing buffer (0.5×SSC, 0.1% SDS). Southern blotting signal was detected as follows:
1) shaking for 30 minutes after adding blocking buffer (Roche) to the membrane
2) shaking for 30 minutes after adding DIG antibody (anti-digoxigenin-AP Fab fragments, Roche)
3) shaking for 15 minutes in washing buffer (Roche)
4) shaking for 3 minutes after adding detection buffer (Roche)
5) After applying CDP-Star, ready-to-use (Roche) on the membrane, developing the blot on x-ray film.

The result was shown in FIG. 44. CyPPO8 F363M #3 line showed one band, which indicates single copy of the gene was inserted in rice genome.

Example 7. Generation of Soybean Transformants Using CyPPO Variants and PPO-Inhibiting Herbicides Tolerance Test 7-1. Generation of Soybean Transformants Vectors to transform soybean plant with CyPPO2 Y373M or CyPPO8 F363M gene were constructed.

The sequence of transit peptide of *A. thaliana* PPO1 was fused to 5' region of CyPPO2 Y373M or CyPPO8 F363M (refer to FIG. 31), and the fused gene was amplified and isolated for vector construction.

PCR reaction mixture (total 50 µl) was prepared by mixing 1 µl of template (the vector which was used for *A. thaliana* transformation), 5 µl of 10× buffer, 1 µl of dNTP mixture (each 10 mM), 1 µl of TOPO-cTP_F primer (10 µM), 1 µl of TOPO-CyPPO2_R or TOPO-CyPPO8_R primer (10 µM), 40 µl of DDW, and 1 µl of Pfu-X (Solgent, 2.5 unit/µl), and amplification was performed under conditions of 1 cycle of 94° C. for 4 minutes, and 25 cycles of 94° C. for 30 seconds, 56° C. for 30 seconds and 72° C. for 1.5 minutes, and 1 cycle of 72° C. for 5 minutes.

Primers used were summarized in Table 21:

TABLE 21

| Primer | Sequence |
|---|---|
| TOPO-cTP_F | CAC CAT GGA GTT ATC TCT TC (SEQ ID NO: 160) |
| TOPO-CyPPO2_R | TCA GAT CGA TCG AGT ATC TG (SEQ ID NO: 161) |
| TOPO-CyPPO8_R | TTA ACC AAA ATA TCT AAC CA (SEQ ID NO: 162) |

Each amplified product was ligated into pENTR-TOPO vector (Invitrogen, refer to FIG. 50) using pENTR Directional TOPO cloning kits (Invitrogen), and the ligation product was transformed to DH5 alpha competent cell (Invitrogen).

Cloned gene in pENTR-TOPO vector was transferred to pB2GW7.0 binary vector to transform plants. Gateway LR Clonase II Enzyme Mix kit (Invitrogen) was used for pB2GW7.0 vector construction. After mixing pENTR/D-TOPO vector in which CyPPO2YM or CyPPO8FM gene was inserted, TE buffer, and LR Clonase II enzyme mix, the mixture was incubated at 25° C. for 1 hr. After Proteinase K solution (Invitrogen) was added to the reaction mixture, it was incubated at 37° C. for 10 minutes, and it was transformed to DH5 alpha competent cell.

*Agrobacterium tumefaciens* EHA105 (Hood et al., New *Agrobacterium* helper plasmids for gene transfer to plants (EHA105). Trans Res. 1993 2:208-218) was electro-transformed with the binary vector constructs above. 'Kwangan' soybean plant was used for transformation. After removing seed coat from soybean seed, hypocotyl was cut and wounded 7-8 times by surgical scalpel (#11 blade). Approximately 50 pieces of explants were mixed with transformed *Agrobacterium* EHA105, and the mixture was sonicated for 20 seconds and then incubated for 30 minutes for inoculation. It was placed on CCM (Co-cultivation media; 0.32 g/L Gamborg B5, 4.26 g/L MES, 30 g/L sucrose, 0.7% agar)

media. Then, it was co-cultured in a growth chamber (25° C., 18 hr light/6 hr dark) for 5 days.

Then it was washed for 10 minutes in liquid ½ SIM (shoot induction media; 3.2 g/L B5 salt, 1.67 mg/L BA, 3 mM MES, 0.8% (w/v) agar, 3% (w/v) sucrose, 250 mg/L cefotaxime, 50 mg/L vancomycin, 100 mg/L ticarcillin, pH 5.6) and was placed on SIM without antibiotics and cultured in a growth chamber (25° C., 18 hr light/6 hr dark) for 2 weeks.

The shoot-induced explants were transplanted on SIM-1 (SIM media supplemented with 10 mg/L DL-phosphinothricin, pH 5.6). The browned shoots were transplanted on SEM (shoot elongation media; 4.4 g/L MS salt, 3 mM MES, 0.5 mg/L GA3, 50 mg/L asparagine, 100 mg/L pyroglutamic acid, 0.1 mg/L IAA, 1 mg/L zeatin, 3% (w/v) sucrose, 0.8% (w/v) agar, 250 mg/L cefotaxime, 50 mg/L vancomycin, 100 mg/L ticarcillin, 5 mg/L DL-phosphinothricin, pH 5.6). The elongated shoots over 4 cm height were transferred on RIM (root induction medium; 4.4 g/L MS salt, 3 mM MES, 3% sucrose, 0.8% agar, 50 mg/L cefotaxime, 50 mg/L vancomycin, 50 mg/L ticarcillin, 25 mg/L asparagine, 25 mg/L pyroglutamic acid, pH 5.6).

When the roots grew sufficiently, the plants were moved to bed soil (Bioplug No. 2, Farmhannong) mixed with vermiculite in 2:1 (v/v). After 10 days, leaves were painted with 100 mg/L DL-phosphinothricin.

7-2. Analysis of Introduced Genes in Soybean Transformants

In order to analyze the copy number of introduced genes in CyPPO2 Y373M transformed soybean $T_0$ plants (line no. 12, 14, 16, 24, 25, 27, 28, 34, and 41) and CyPPO8 F363M transformed soybean $T_1$ plant (line no. 3, 5, 7, 9, 11, 14, 17, 36, and 44), genomic DNA was extracted with 250 mg of leaf tissue of each transformed plant referring to Example 6-4.

The 10~40 μg of genomic DNA was digested with EcoRI (Enzynomics) for overnight, and southern blotting was performed following the method in Example 6-4.

The Bar DNA probe for hybridization was prepared by labelling with DIG (Digoxigenin)-dNTP by PCR reaction. PCR reaction mixture (total 50 μl) was prepared by mixing 0.5 μl of template (the vector which was used for soybean transformation), 5 μl of 10× buffer, 10 μl of DIG-dNTP mixture (dATP, dCTP, dGTP, respectively, 0.5 mM, dTTP 0.32 mM, DIG-11-dUTP 0.18 mM), 0.5 μl of forward primer (100 μM), 0.5 μl of reverse primer (100 μM), 33 μl of DDW, and 0.5 μl of e-Taq (Solgent, 2.5 unit/μl), and amplification was performed under conditions of 1 cycle of 94° C. for 4 minutes, and 35 cycles of 94° C. for 30 seconds, 56° C. for 30 seconds and 72° C. for 30 seconds, and 1 cycle of 72° C. for 5 minutes.

Bar Probe Primer:

```
Forward primer for bar probe:
                              (SEQ ID NO: 163)
5'-TTC CGT ACC GAG CCG CAG GA-3'

Reverse primer for bar probe:
                              (SEQ ID NO: 164)
5'-CGT TGG GCA GCC CGA TGA CA-3'
```

For comparison, the genomic DNA of non-transformed Kwangan soybean (WT) was used as a negative control.

The result was shown in FIG. 51. The number of bands shown on the film in FIG. 51 means the number of inserted genes. In case of non-transformed Kwangan soybean (WT), no band was detected, and it was demonstrated that one copy of CyPPO gene was integrated into the genome of Kwangan soybean in CyPPO2 Y373M transformant lines No. 14, 25, 34, and 41 and in CyPPO8 F363M transformant lines No. 3, 5, 7, 11, 14, and 17.

Hereinafter, using the single copy inserted transformant lines, herbicide tolerance was evaluated and CyPPO protein expression was tested.

7-3. Verification of Herbicide Tolerance of Transformed Soybeans

In order to examine the level of herbicide tolerance of CyPPO2 Y373M or CyPPO8 F363M transformed soybean plants, herbicide was applied to soybean transformants ($T_2$ generation).

Twenty micromolar of tiafenacil (corresponding to 42 g ai/ha) or 150 μM (corresponding to 315 g ai/ha) or 300 μM (corresponding to 630 g ai/ha) of saflufenacil was sprayed respectively to the soybean of V2~3 stage. The 100 ml herbicide of the concentration above was evenly sprayed on the area of 40×60 cm, and after 5 days, herbicide tolerance was evaluated. Non-transformed soybean (represented by Kwangan soybean) was used as a control.

FIG. 52 shows the result. While non-transformed Kwangan soybean died at each herbicide treatment with injury index 9, the injury index of CyPPO2 Y373M or CyPPO8 F363M transformants was 1~3 when treated with 20 μM tiafenacil. And the injury index of CyPPO2 Y373M transformants was 0 when treated with 150 μM saflufenacil and that of CyPPO8 F363M transformants was 0 when treated with 300 μM saflufenacil. The injury index was determined by the following criteria:

TABLE 22

| Injury Index | Damage description by herbicide treatment |
|---|---|
| 0 | No damage |
| 1 | Very week level, very small part of leaves was damaged or chlorosis was observed. |
| 2 | Weak damage symptom with a little severe chlorosis, no effect on the whole growth condition |
| 3 | No effect on the primary leaf and growing point, a little severe damage was observed in the secondary leaf tissue |
| 4 | The whole plant shape was little changed. There was no effect on stem, but chlorosis and necrosis were observed in the secondary growing point and leaf tissues. Considered that re-growth is possible within one week. |
| 5 | The whole plant shape was definitely changed. Chlorosis and necrosis were observed in many leaves and growing point. The primary growing point was not damaged, and stem had green color. Considered that re-growth is possible within one week. |
| 6 | Strong damage on the growth of a newly growing small leaf was observed. Considered that the plant could survive by the growth in the different growing point. Chlorosis and necrosis were observed in most of leaves, and stem had green color. Considered that re-growth is possible, but damage symptoms were severely observed. |
| 7 | Chlorosis was exhibited in most of growing points. Re-growth in one of growing point could be possible, and two leaves had green color partially. Partial chlorosis, necrosis, and green color. The rest part of plants including stem exhibited necrosis. |
| 8 | All the growing points were necrosed, and plants are likely to die. One leaf had green color partially. |
| 9 | Plant necrosed. |

The result shows that while the wild type Kwangan soybean died with herbicide treatment at each concentration, the transformants exhibited weak damage with tiafenacil treatment and hardly exhibited damage with saflufenacil treatment. As a reference, $IC_{50}$ value for tiafenacil or saflufenacil of CyPPO2 Y373M was 250 nM or 5,000 nM, respectively, and $IC_{50}$ value for tiafenacil or saflufenacil of CyPPO8 F363M was 183 nM or 5,000 nM, respectively (Tables 10 to 11).

7-4. Verification of Protein Expression in Transformed Soybeans

The expression of CyPPO2 Y373M protein or CyPPO8 F363M protein in transformed plants was examined.

In order to examine protein expression, the total protein was extracted in each transformant ($T_1$) and western blot analysis was conducted. After triturating the leaf tissue of each transformant with liquid nitrogen, protein extraction buffer (0.8% SDS, 4% glycerol, 2% beta-mercaptoethanol, 0.0008% bromophenol blue, 0.125M Tris-Cl, pH 7.4) was added and the total protein was extracted.

The extracted protein was electrophoresed in SDS-PAGE gel and transferred to PVDF membrane. The membrane was labeled with antibody specific to each inserted protein (CyPPO2-specific antibody for CyPPO2 Y373M transformant, CyPPO8-specific antibody for CyPPO8 F363M transformant; GenScript).

The result demonstrated that CyPPO2 Y373M protein or CyPPO8 F363M protein was expressed in all transformant individuals (FIG. 53). It indicates that herbicide tolerance of the transformants was conferred by the expression of CyPPO2 Y373M protein or CyPPO8 F363M protein.

Example 8. Generation of Rapeseed Transformants Using CyPPO Variants and PPO-Inhibiting Herbicides Tolerance Test 8-1. Generation of Rapeseed Transformants The vector, in which CyPPO8 F363M gene was inserted, constructed in the Example 5-1 was used to generate rapeseed transformants.

The seeds of rapeseed were sterilized with 70% (v/v) ethanol for 4 minutes and then with 1.3% (v/v) sodium hypochlorite acid for 30 minutes. After washing 5 times with sterile water, moisture was removed on a sterile filter paper, and the seeds were transplanted to MSO media (4.43 g/L MS salt, 30 g/L sucrose, 3 g/L phytagel, pH 5.8), and cultured for 5 days in a culture room at 25±1° C. under the light condition (16 h light/8 h dark, 25,000 Lux).

After *Agrobacterium* was transformed with the vector inserted with CyPPO8 F363M gene, it was inoculated in LB media supplemented with spectinomycin (100 mg/L) and rifampicin (50 mg/L), and cultured for over 16 hrs in a shaking incubator at 28° C. Cotyledons and hypocotyls of a rapeseed plant were cut and co-cultured with the *Agrobacterium* for 3 days (dark condition, 25±1° C.). The inoculated plant tissues were transferred to a selection media (4.43 g/L MS salt, 20 g/L sucrose, 0.2 mg/L NAA, 8 µM TDZ, 0.01 mg/L GA3, 50 µM silver thiosulfate, 10 mg/L PPT, 500 mg/L carbenicillin, 4 g/L phytagel, pH 5.8) and cultured in a growth chamber (25±1° C., 16 h light/8 h dark).

The inoculated plant tissues were subcultured every two weeks and then redifferentiated shoots from callus were transferred to root induction media (4.43 g/L MS salt, 30 g/L sucrose, 3 g/L phytagel, activated charcoal 3 g/L, pH 5.8), thereby inducing roots. Root-induced small plants were transferred to pots, and then transformants were confirmed using excised leaves.

8-2. Verification of Herbicide Tolerance of Transformants

After seeds of the rapeseed transformants ($T_1$) and Youngsan rapeseed (wild type rapeseed, control) were sterilized with 50% (v/v) sodium hypochlorite for 30 minutes, they were washed 5 times with sterile water. Transformants were sown in a selection media (½ MS, 50 nM tiafenacil, pH 5.8) and the wild type rapeseeds were sown in ½ MS media. Individuals survived after 7 days were transplanted to pots and cultured in a growth chamber (25±1° C., 16 h light/8 h dark). After 35 days of transplantation, 10 µM tiafenacil and 10 µM saflufenacil were treated respectively by 100 mL (0.05% Silwet L-77) per a tray (40×60 cm, 0.24 $m^2$) in which the pot placed.

The results of 7 days after treatment of the herbicide were shown in FIG. 54 (tiafenacil treatment) and FIG. 55 (saflufenacil treatment). In FIG. 54 and FIG. 55, "Youngsan" represented the wild type Youngsan rapeseed. The injury level was shown in Table 23 by evaluating with injury index 0-5 (no damage-death; refer to Table. 17):

TABLE 23

| | 10 µM Tiafenacil | 10 µM Saflufenacil |
|---|---|---|
| WT (Youngsan) | 4 | 4 |
| CyPPO8 F363M 2-4 | 2 | NT |
| CyPPO8 F363M 2-7 | 2 | NT |
| CyPPO8 F363M 2-8 | 1 | NT |
| CyPPO8 F363M 2-6 | NT | 0 |
| CyPPO8 F363M 2-9 | NT | 0 |
| CyPPO8 F363M 2-10 | NT | 0 |

(NT: Not tested)

While Youngsan (wild type rapeseed, control) exhibited injury level 4, CyPPO8 F363M-2 lines exhibited tolerance injury level 1-2 to 10 µM tiafenacil (FIG. 54). In addition, after 10 µM saflufenacil treatment, CyPPO8 F363M-2 lines exhibited no damage (FIG. 55).

8-3. Verification of Protein Expression of Transformed Rapeseed

The expression of inserted genes in CyPPO8 F363M rapeseed transformants was confirmed. Among CyPPO8 F363M lines, 5 individuals (2-1, 2-2, 2-6, 2-9, and 2-10) confirmed to have herbicide tolerance were selected for western blotting.

After approximately 200 mg of leaves of each rapeseed transformant was ground using liquid nitrogen and a pestle, 0.8 mL phenol (Tris-buffered, pH 8.0) and 0.8 mL dense SDS buffer (30% (w/v) sucrose, 2% (w/v) SDS, 0.1 M Tris-Cl, pH 8.0, 5% (v/v) beta-mercaptoethanol) were added and mixed by vortexing for 30 seconds, and centrifugation was conducted at 10,000×g for 3 minutes. Supernatant was transferred to a new tube, and 5-volume of methanol (4° C., 0.1 M ammonium acetate) was added and mixed, and then left at −20° C. for 30 minutes. Proteins were precipitated by centrifugation at 10,000×g for 5 minutes, and washed with 1 mL methanol (4° C., 0.1 M ammonium acetate) twice and 80% acetone (4° C.) twice, and dried. The dried proteins were dissolved with 2% (w/v) SDS buffer (50 mM Tris-Cl, pH 6.8, 1 mM DTT).

Since the CyPPO8 F363M vector was constructed with HA tag (refer to Example 5-1), western blotting was conducted with HA antibody (Santa Cruz) to confirm the CyPPO8 F363M protein expression.

The western blot result was shown in the top of FIG. 56. It was demonstrated that the CyPPO8 protein was expressed in all individuals except Youngsan (wild type rapeseed, control). Such result indicated that herbicide tolerance was conferred by protein expression of introduced genes.

Additionally, the Coomassie blue staining result of the PVDF membrane was shown in the bottom of FIG. 56. It was demonstrated that the amount of protein of each sample was almost equal.

The invention claimed is:

1. A polynucleotide encoding a polypeptide, wherein the polypeptide is:

(1) a polypeptide which is modified from SEQ ID NO: 5 by mutation of:
F363M, F363V, F363L, F363C, F363I, or F363T,
A162C or A162L,
R85A,
V160C or V160S,
V308M,
F156A,
F327V,
L330T, or
I343T;

(2) a polypeptide which is modified from SEQ ID NO: 5 by a combination of (i) F363M, F363V, F363L, F363C, F363I, or F363T, and (ii) at least one mutation selected from the group consisting of:
P84L,
R85A, R85C, R85H, R85L, R85T, or R85V,
A162C or A162L,
P306L or P306A,
V308L or V308M,
N362S,
V160S or V160C,
I343V or I343T
F156A,
Q179G,
F327V, and
L330T; or (3) a polypeptide comprising an amino acid sequence having 95% or higher identity to the polypeptide (1) or (2), and wherein the polypeptide confers or enhances herbicide tolerance of a plant or algae, and the herbicide is at least one an herbicide inhibiting protoporphyrinogen oxidase selected from the group consisting of tiafenacil, saflufenacil, fomesafen, butafenacil, flumioxazin, sulfentrazone, acifluorfen, pentoxazone, and pyraflufen-ethylyraclonil.

2. The polynucleotide of claim 1, wherein the polypeptide is modified from SEQ ID NO: 5 by a mutation of:
F363M, F363V, F363L, F363C, F363I, F363T, A162C, A162L, R85A, V160C, V160S, V308M, F156A, F327V, L330T, I343T, P84L+F363M, R85A+F363M, R85A+F363I, R85C+F363M, R85H+F363M, R85L+F363M, R85T+F363M, R85V+F363M, R85A+A162L+F363M, R85A+A162L+F363I, R85A+A162C+F363M, R85A+A162C+F363I, R85A+V308M+F363M, V160S+F363M, V160S+F363I, V160S+V308M+F363I, A162L+F363M, A162C+F363M, A162C+F363I, A162C+F363L, A162C+V308M+F363M, A162C+V308L+F363M, A162L+Q179G+F363M, P306A+V308L, V308M+F363M, V308M+F363I, I343T+F363M, I343V+F363M, N362S+F363M, V308M+F363V, R85A+F363V, R85A+F363I, A162C+F363V, A162L+F363V, A162L+F363L, A162L+F363V, V160S+F363L, V160S+F363V, V160C+F363M, V160C+F363I, V160C+F363L, V160C+F363V, V308M+F363L, R85A+V160S+F363V, R85A+V160S+F363M, V160C+V308M+F363M, V160C+V308M+F363V, V160C+A162C+F363V, V160C+A162L+F363M, V160C+A162L+F363V, A162C+V308M+F363I, A162C+V308M+F363L, A162C+V308M+F363V, A162L+V308M+F363M, V160C+A162C+V308M+F363M, V160C+A162C+V308M+F363V, V160C+A162L+V308M+F363M, or R85A+V160S+A162C+F363M.

3. The polynucleotide of claim 1, wherein the polypeptide is modified from SEQ ID NO: 5 by a mutation of:
(1) F363M, F363V, F363L, or F363I, or
(2) a combination of (i) F363M, F363V, F363L, or F363I and (ii) at least one mutation selected from the group consisting of:
R85A,
V160S or V160C,
A162L or A162C, and
V308M.

4. A recombinant vector comprising the polynucleotide of claim 1.

5. The recombinant vector according to claim 4, wherein the polypeptide is modified from SEQ ID NO: 5 by a mutation of:
F363M, F363V, F363L, F363C, F363I, F363T, A162C, A162L, R85A, V160C, V160S, V308M, F156A, F327V, L330T, I343T, P84L+F363M, R85A+F363M, R85A+F363I, R85C+F363M, R85H+F363M, R85L+F363M, R85T+F363M, R85V+F363M, R85A+A162L+F363M, R85A+A162L+F363I, R85A+A162C+F363M, R85A+A162C+F363I, R85A+V308M+F363M, V160S+F363M, V160S+F363I, V160S+V308M+F363I, A162L+F363M, A162C+F363M, A162C+F363I, A162C+F363L, A162C+V308M+F363M, A162C+V308L+F363M, A162L+Q179G+F363M, P306A+V308L, V308M+F363M, V308M+F363I, I343T+F363M, I343V+F363M, N362S+F363M, V308M+F363V, R85A+F363V, R85A+F363L, A162C+F363V, A162L+F363I, A162L+F363L, A162L+F363V, V160S+F363L, V160S+F363V, V160C+F363M, V160C+F363I, V160C+F363L, V160C+F363V, V308M+F363L, R85A+V160S+F363V, R85A+V160S+F363M, V160C+V308M+F363M, V160C+V308M+F363V, V160C+A162C+F363V, V160C+A162L+F363M, V160C+A162L+F363V, A162C+V308M+F363I, A162C+V308M+F363L, A162C+V308M+F363V, A162L+V308M+F363M, V160C+A162C+V308M+F363M, V160C+A162C+V308M+F363V, V160C+A162L+V308M+F363M, or R85A+V160S+A162C+F363M.

6. A transformed cell comprising the recombinant vector of claim 4.

7. A composition for conferring or enhancing herbicide tolerance of a plant or algae, comprising the polynucleotide of claim 1, a recombinant vector comprising the polynucleotide, or a transformed cell comprising the recombinant vector, wherein the herbicide is at least one herbicide inhibiting protoporphyrinogen oxidase selected from the group consisting of tiafenacil, saflufenacil, fomesafen, butafenacil, flumioxazin, sulfentrazone, acifluorfen, pentoxazone, and pyraflufen-ethylyraclonil.

8. The composition of claim 7, wherein the plant or algae further comprise a gene encoding a second herbicide-tolerant polypeptide, and tolerance to the second herbicide is conferred or enhanced.

9. The composition of claim 8, wherein the second herbicide is selected from the group consisting of glyphosate, glufosinate, dicamba, 2,4-D(2,4-Dichlorophenoxyacetic acid), isoxaflutole, ALS (acetolactate synthase)-inhibiting herbicide, photosystem II-inhibiting herbicide, phenylurea-based herbicide, bromoxynil-based herbicide, and combinations thereof.

10. The composition of claim 8, wherein the gene encoding the second herbicide-tolerant polypeptide is one or more selected from the group consisting of:
glyphosate herbicide-tolerant cp4 epsps, mepsps, 2mepsps, goxv247, gat4601 or gat4621 gene;
glufosinate herbicide-tolerant BAR or PAT gene;
dicamba herbicide-tolerant dmo gene;
2,4-D(2,4-dichlorophenoxyacetic acid) herbicide-tolerant AAD-1 or AAD-12 gene;
isoxaflutole herbicide-tolerant HPPDPF W336 gene;
sulfonylurea herbicide-tolerant ALS, Csr1, Csr1-1, Csr1-2, GM-HRA, S4-HRA, Zm-HRA, SurA or SurB gene;
photosystem II-inhibiting herbicide-tolerant psbA gene;
phenylurea herbicide-tolerant CYP76B1 gene;
bromoxynil herbicide-tolerant bxn gene; and
combinations thereof.

11. A transformant of a plant or algae having herbicide tolerance, or a clone or progeny thereof, comprising the polynucleotide of claim 1, wherein the herbicide is at least one herbicide inhibiting protoporphyrinogen oxidase selected from the group consisting of tiafenacil, saflufenacil, fomesafen, butafenacil, flumioxazin, sulfentrazone, acifluorfen, pentoxazone, and pyraflufen-ethylyraclonil.

12. The transformant, clone, or progeny thereof of claim 11, wherein the transformant is a plant cell, protoplast, callus, hypocotyl, seed, cotyledon, shoot, or whole plant.

13. A method of preparing a transgenic plant or algae having herbicide tolerance, the method comprising transforming algae, a plant cell, protoplast, callus, hypocotyl, seed, cotyledon, shoot, or whole plant, with the polynucleotide of claim 1, wherein the herbicide is at least one herbicide inhibiting protoporphyrinogen oxidase selected from the group consisting of tiafenacil, saflufenacil, fomesafen, butafenacil, flumioxazin, sulfentrazone, acifluorfen, pentoxazone, and pyraflufen-ethylyraclonil.

14. A method of conferring or enhancing herbicide tolerance of a plant or algae, the method comprising transforming algae, a plant cell, protoplast, callus, hypocotyl, seed, cotyledon, shoot, or whole plant, with the polynucleotide of claim 1, wherein the herbicide is at least one herbicide inhibiting protoporphyrinogen oxidase selected from the group consisting of tiafenacil, saflufenacil, fomesafen, butafenacil, flumioxazin, sulfentrazone, acifluorfen, pentoxazone, and pyraflufen-ethylyraclonil.

* * * * *